United States Patent
Boyle et al.

(10) Patent No.: US 7,504,416 B2
(45) Date of Patent: Mar. 17, 2009

(54) 4-SUBSTITUTED QUINOLINES AS ANTITUMOR AGENTS

(75) Inventors: Francis Thomas Boyle, Cheshire (GB); Keith Hopkinson Gibson, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/826,507

(22) Filed: Jul. 16, 2007

(65) Prior Publication Data

US 2008/0027054 A1    Jan. 31, 2008

Related U.S. Application Data

(62) Division of application No. 10/415,813, filed as application No. PCT/GB01/04733 on Oct. 25, 2001, now Pat. No. 7,253,184.

(30) Foreign Application Priority Data

Nov. 2, 2000 (GB) .................................. 0026745.0
Nov. 2, 2000 (GB) .................................. 0026747.6

(51) Int. Cl.
*A61K 31/4706* (2006.01)
*C07D 215/42* (2006.01)

(52) U.S. Cl. ....................... 514/312; 546/153; 514/313
(58) Field of Classification Search ................ 546/153, 546/159; 514/312, 313
See application file for complete search history.

(56) References Cited

U.S. PATENT DOCUMENTS

| 3,376,195 A | 4/1968 | Allais et al. |
|---|---|---|
| 3,936,461 A | 2/1976 | Schwender et al. |
| 4,421,920 A | 12/1983 | Baudouin |
| 5,409,930 A | 4/1995 | Spada et al. |
| 5,650,415 A | 7/1997 | Tang et al. |
| 5,656,643 A | 8/1997 | Spada et al. |
| RE36,256 E | 7/1999 | Spada et al. |
| 6,002,008 A | 12/1999 | Wissner et al. |
| 6,630,489 B1 | 10/2003 | Crawley |

FOREIGN PATENT DOCUMENTS

| EP | 0 326 330 |   | 8/1989 |
|---|---|---|---|
| FR | 2 077 455 |   | 10/1971 |
| WO | 93/03030 |   | 2/1993 |
| WO | 96/09294 | A | 3/1996 |
| WO | 97/03069 |   | 1/1997 |
| WO | 97/17329 |   | 5/1997 |
| WO | 98/02434 |   | 1/1998 |
| WO | 98/13350 |   | 4/1998 |
| WO | 98/43960 | A | 10/1998 |
| WO | 99/01421 |   | 1/1999 |
| WO | 99/01426 |   | 1/1999 |
| WO | 99/35146 |   | 7/1999 |
| WO | 00/18740 |   | 4/2000 |
| WO | 00/18761 | A | 4/2000 |
| WO | WO 00/18740 | * | 4/2000 |
| WO | 00/68199 | A | 11/2000 |
| WO | 00/68200 |   | 11/2000 |
| WO | 00/68201 | A | 11/2000 |

* cited by examiner

*Primary Examiner*—Rei-Tsang Shiao
*Assistant Examiner*—Janet L Coppins
(74) *Attorney, Agent, or Firm*—Morgan, Lewis & Bockius LLP

(57) ABSTRACT

The invention concerns compounds of formula (I), wherein each of $R^1$, $R^2$, $R^3$, $R^4$, $R^5$, $R^6$, $R^8$, $R^9$, $R^{10}$ m, n, p, X, Y and Z have any meanings defined in the description, processes for their preparation, pharmaceutical compositions containing them and their use in the manufacture of a medicament for use as an anti-proliferative agent in the treatment of solid tumor disease.

2 Claims, No Drawings

4-SUBSTITUTED QUINOLINES AS ANTITUMOR AGENTS

This is a divisional of application Ser. No. 10/415,813, filed May 2, 2003, now U.S. Pat. No. 7,253,184, which is the US National Stage of PCT/GB01/04733, filed Oct. 25, 2001, which claimed priority of GB 0026745.0, and GB 0026747.6, both filed Nov. 2, 2000.

The present invention relates to certain novel quinoline derivatives as well as to their use as pharmaceuticals, in particular as inhibitors of specific kinase enzymes, such as MEK enzymes. Further aspects of the invention include pharmaceutical compositions and methods of treatment of proliferative disease such as cancer using said compounds.

Cancer is a disease in which cells grow and divide in an uncontrolled fashion. This uncontrolled growth arises from abnormalities in signal transduction pathways that are used by normal cells to regulate cell growth and division in response to various signalling molecules. Normal cells do not proliferate unless stimulated to do so by specific signal molecules located outside the cell derived from nearby cells or tissues. Growth factors bind to the cell membrane via specific receptors which have intrinsic enzyme activity. These receptors relay the growth signal to the cell nucleus via a series of signalling proteins. In cancer, a number of defects in signal pathways are apparent. For example, cancer cells may produce their own growth factors which bind to their cognate receptors, resulting in an autocrine loop, or receptors may be mutated or overexpressed leading to an increased, continuous signal to proliferate. In addition, negative regulators of cell growth may be lost.

Oncogenes are cancer related genes which often encode abnormal versions of signal pathway components, such as receptor tyrosine kinases, serine-threonine kinases, or downstream signaling molecules such as the ras genes, which code for closely related small guanine nucleotide binding proteins which hydrolyse bound guanosine triphosphate (GTP) to guanosine diphosphate (GDP). Ras proteins are active in promoting cell growth and transformation when they are bound to GTP and inactive when they are bound to GDP. Transforming mutants of p21ras are defective in their GTPase activity and hence remain in the active GTP bound state. The ras oncogene is known to play an integral role in certain cancers, and has been found to contribute to the formation of over 20% of all cases of human cancer.

When activated by ligand, cell surface receptors which are coupled to the mitogenic response, such as growth factor receptors, initiate a chain of reactions which leads to the activation of guanine nucleotide exchange activity on ras. When in its active GTP-bound state, a number of proteins interact directly with ras at the plasma membrane resulting in signal transmission through several distinct pathways. The best characterised effector protein is the product of the raf proto-oncogene. The interaction of raf and ras is a key regulatory step in the control of cell proliferation. Ras-mediated activation of the raf serine-threonine kinase in turn activates the dual-specificity MEK (MEK1 and MEK2), which is the immediate upstream activator of mitogen activated protein kinase (MAPKs known as extracellular signal regulated protein kinases or ERK1 and ERK2). To date, no substrates of MEK other than MAPK have been identified, though recent reports indicate that MEK may also be activated by other upstream signal proteins such as MEK kinase or MEKK1 and PKC. Activated MAPK translocates and accumulates in the nucleus, where it can phosphorylate and activate transcription factors such as Elk-1 and Sap1a, leading to the enhanced expression of genes such as that for c-fos.

The ras-dependent raf-MEK-MAPK cascade is one of the key signalling pathways responsible for transmitting and amplifying mitogenic signals from cell surface to the nucleus resulting in changes in gene expression and cell fate. This ubiquitous pathway appears essential for normal cell proliferation and constitutive activation of this pathway is sufficient to induce cellular transformation. Transforming mutants of p21ras are constitutively active, resulting in raf, MEK and MAPK activity and cell transformation. Inhibition of MEK activity using either antisense raf, a dominant negative MEK mutant or the selective inhibitor PD098059 have been shown to block the growth and morphological transformation of ras-transformed fibroblasts.

The mechanism of activation of raf, MEK and MAPK is through phosphorylation on specific serine, threonine or tyrosine residues. Activated raf and other kinases phosphorylate MEK1 on S218 and S222 and MEK2 on S222 and S226. This results in MEK activation and subsequent phosphorylation and activation of ERK1 on T190 and Y192 and ERK2 on Ti 83 and Y185 by the dual specificity MEKs. Whilst MEK can be activated by a number of protein kinases, and active MAPKs phosphorylate and activate a number of substrate proteins including transcription factors and other protein kinases, MEKs appear specific and sole activators of MAPKs and could act as a focal point for cross-cascade regulation. MEK1 and MEK2 isoforms show unusual specificity and also contain a proline-rich insert between catalytic subdomains IX and X which is not present in any of the other known MEK family members. These differences between MEK and other protein kinases, together with the known role of MEK in proliferative signalling suggest that it may be possible to discover and employ selective MEK inhibitors as therapeutic agents for use in proliferative disease.

WO 98/43960 discloses a range of 3-cyano quinoline compounds and their use in the treatment of cancer. Certain of the compounds are demonstrated as being inhibitors of Epidermal Growth Factor Receptor Kinase, and to inhibit cancer cell growth. Other quinoline derivatives which inhibit the effect of growth factors such as VEGF are described in WO98/13350.

Copending but unpublished patent application nos PCT/GB00/01697, PCT/GB00/01707 and PCT/GB00/01698 describe a series of quinoline compounds which are inhibitors of the kinase activity of MEK and as a result, can produce therapeutically useful effects in the treatment of proliferative disease and in particular cancer. The applicants have found that further such compounds and in particular those which have a substituent at the 4-position on the quinolines which includes 3 rings interposed with heteroatoms or chains including heteroatoms, have particularly good activity.

According to a first feature of the present invention there is provided a compound of formula (I)

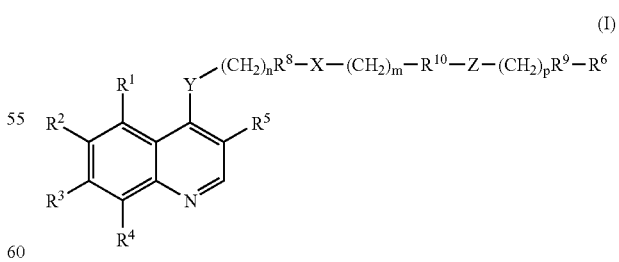

or a pharmaceutically acceptable salt, pro-drug or solvate thereof wherein:

n is 0 or 1;

Y is selected from —NH—, —O—, —S—, or —NR$^7$— where R$^7$ is alkyl of 1-6 carbon atoms;

$R^5$ is cyano, fluoro, chloro or bromo;

$R^8$ is a divalent cycloalkyl of 3 to 7 carbon atoms, which may be optionally further substituted with one or more alkyl of 1 to 6 carbon atom groups; or is a divalent pyridinyl, pyrimidinyl, or phenyl ring, wherein the pyridinyl, pyrimidinyl, or phenyl ring may be optionally further substituted with one or more groups selected from halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, and benzoylamino;

X is selected from —NH—, —O—, —S—, —CH$_2$— or —NR$^{7'}$— where $R^{7'}$ is alkyl of 1-6 carbon atoms;

m and p are independently selected from 0, 1, 2 or 3;

$R^{10}$ is an optionally substituted arylene, optionally substituted $C_{3-10}$cycloalkylene ring or optionally substituted divalent heterocyclic ring or an N-oxide of any nitrogen containing ring, -Z- is a direct bond or a group of sub-formula (i)

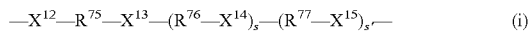

where $X^{12}$, $X^{13}$ each $X^{14}$ and each $X^{15}$ are independently selected from —O—, —C(O)—, —C(O)O—, —S—, —SO—, —SO$_2$—, —NR$^{78}$C(O)—, —NR$^{78}$C(O)O—, —C(O)NR$^{79}$—, —C(O)ONR$^{79}$—, —SO$_2$NR$^{80}$—, —NR$^{81}$SO$_2$— or —NR$^{82}$— (wherein $R^{78}$, $R^{79}$, $R^{80}$, $R^{81}$ and $R^{82}$ each independently represents hydrogen, $C_{1-3}$alkyl optionally substituted by hydroxy, or $C_{1-3}$alkoxy$C_{2-3}$alkyl) and each $X^{13}$, $X^{14}$ and $X^{15}$ may additionally be a direct bond;

s and s' are independently selected from 0, 1, 2 or 3;

$R^{75}$, $R^{76}$ and $R^{77}$ are independently selected from $C_{1-6}$alkylene, $C_{2-6}$alkenylene or $C_{2-6}$alkynylene optionally substituted by halo and hydroxy or $R^{75}$, $R^{76}$ and $R^{77}$ can each independently be direct bonds;

$R^9$ is an optionally substituted divalent heterocyclic group, $C_{1-5}$alkylene, or divalent $C_{3-7}$cycloalkyl;

$R^6$ is hydrogen, amino or a group of sub-formula (ii)

$$—X^{16}R^{83}—(X^{17}R^{84})_t—X^{18}R^{85} \qquad (ii)$$

where $X^{16}$, $X^{18}$ and each $X^{17}$ are each independently selected from a direct bond, —O—, —C(O)—, —S—, —SO—, —SO$_2$—, —NR$^{86}$C(O)—, —NR$^{86}$C(O)O—, —C(O)NR$^{87}$—, —C(O)ONR$^{87}$—, —SO$_2$NR$^{88}$—, —NR$^{89}$SO$_2$— or NR$^{90}$ (wherein $R^{86}$, $R^{87}$, $R^{88}$, $R^{89}$ and $R^{90}$ each independently represents hydrogen, $C_{1-3}$alkyl or $C_{1-3}$alkoxy$C_{2-3}$alkyl), $R^{83}$ and each $R^{84}$ are independently selected from $C_{1-6}$alkylene, $C_{2-6}$alkenylene or $C_{2-6}$alkynylene;

$R^{85}$ is selected from hydrogen, $C_{1-6}$alkyl, $C_{2-6}$alkenyl or $C_{2-6}$alkynyl, t is 0, 1, 2 or 3;

$R^1$, $R^2$, $R^3$, $R^4$ are independently selected from hydrogen, hydroxy, halogeno, cyano, nitro, trifluoromethyl, $C_{1-3}$alkyl, —NR$^{11}$R$^{12}$— (wherein $R^{11}$ and $R^{12}$, which may be the same or different each represents hydrogen, or $C_{1-3}$alkyl), 5-6-membered saturated heterocyclic group with 1-2 heteroatoms, selected independently from O, S and N, or a group $R^{13}$—X$^1$—(CH$_2$)$_x$ wherein x is 0 or an integer of from 1 to 3, $X^1$ represents a direct bond, —O—, —CH$_2$—, —OC(O)—, —C(O)—, —S—, —SO—, —SO$_2$—, —NR$^{14}$C(O)—, —NR$^{14}$C(O)O—, C(O)NR$^{15}$—, —C(O)ONR$^{15}$—, —SO$_2$NR$^{16}$, —NR$^{17}$SO$_2$— or —NR$^{18}$— (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl), and $R^{13}$ is hydrogen, optionally substituted hydrocarbyl, or optionally substituted heterocyclyl, provided that:

i) where the group of sub-formula (ii) is $C_{1-6}$alkyl or $R^6$ is hydrogen and $R^9$ is a divalent heterocycyl, Z is other than a direct bond, or the group -Z(CH$_2$)$_p$— is other than $C_2$ alkylene, or the group of sub-formula (i) is other than —S—;

ii) the group $R^9$—$R^6$ cannot together be $C_{1-5}$ alkyl, $C_{2-6}$ alkenyl, $C_{2-6}$alkynyl or (C$_{1-5}$ alkylene)OH unless a) in the group of sub-formula (i), $R^{75}$ or $R^{76}$ is the group —C($R^A R^B$)— where $R^A$ and $R^B$ are each independently selected from $C_{1-3}$ alkyl, $C_{2-3}$ alkenyl, $C_{2-3}$ alynyl and halo;

b) in the group of sub-formula (i), where the terminal group $X^{12}$, $X^{13}$ or $X^{14}$ linked to —(CH$_2$)$_p$— or —$R^9$, is selected from —CONR$^{79}$—; —C(O)ONR$^{79}$; —SO$_2$NR$^{80}$ and —NR$^{78}$C(O); then $R^{78}$, $R^{79}$, and $R^{80}$ are other than hydrogen but when $X^{13}$ is —C(O)NR$^{79}$ then $R^{10}$ cannot be pyridyl;

c) the group of sub-formula (i) is selected from —C(O)—NR$^{82}$—O— and —O—CH$_2$—C(O)NR$^{82}$—CH$_2$—C(O)O—, where $R^{82}$ is other than hydrogen;

d) the group —$R^{10}$-Z-(CH$_2$)$_p R^9$—$R^6$ is selected from

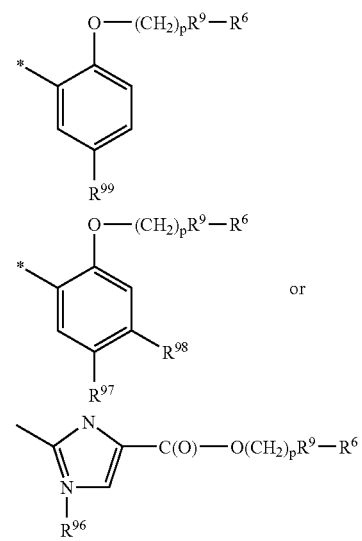

where $R^{99}$ is selected from —NC(O)CH$_3$, —NC$_2$H$_5$ or —OCH$_3$;

$R^{97}$ and $R^{98}$ are each independently selected from hydrogen and fluoro, provided that at least one of $R^{97}$ and $R^{98}$ is fluoro;

* denotes the point of attachment; and p, $R^9$ and $R^6$ are as hereinbefore defined;

e) the group
X—(CH$_2$)$_m$—R$^{10}$-Z-(CH$_2$)$_p$—R$^9$—R$^6$ is

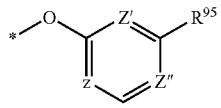

where * denotes the point of attachment to R$^8$;
R$^{95}$ is selected from —C(O)NR$^{94}$R$^{93}$ and C$_{1-6}$ alkoxyl, where R93 and R94 each independently represents hydrogen or C$_{1-3}$ alkyl;
Z, Z', Z'' each independently represent —CH— or nitrogen and provided that at least one of Z, Z', Z'' is nitrogen;
iii) where the group of sub-formula (i) comprises the group —X$^{12}$—R$^{75}$—X$^{13}$—(R$^{76}$—X$^{14}$)$_s$—(R$^{77}$—X$^{15}$)$_{s'}$— where X$^{12}$ is selected from —O—, —NR$^{82}$—, or —NR$^{78}$C(O)—;
X$^{13}$ is selected from —C(O)NR$^{79}$, a direct bond or —NR$^{82}$—;
R$^{76}$, X$^{14}$, R$^{77}$, X$^{15}$, s and s' are as hereinbefore defined; then R$^{75}$ is C(R$^A$R$^B$) where R$^A$ and R$^B$ are each independently selected from C$_{1-3}$ alkyl, C$_{2-3}$ alkenyl, C$_{2-3}$ alkynyl and halo; unless
(i) R$^9$ is piperazinyl linked through the nitrogen atoms or pyridyl;
(ii) R$^{75}$ is 1-3 alkyl substituted by hydroxy; or
(ii) R$^{79}$ is other than hydrogen; or
iv) where the group of sub-formula (i) is selected from —(CH$_2$)$_2$C(O)— or —O—(CH$_2$)$_2$ and R$^9$ is a divalent heterocyclic group, then R$^6$ is other than hydrogen.

According to another aspect of the first feature of the present invention there is provided a compound of formula (I')

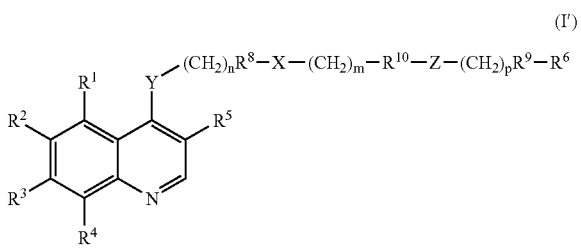

or a pharmaceutically acceptable salt thereof
wherein:
n is 0-1;
Y is selected from —NH—, —O—, —S—, or —NR$^7$— where R$^7$ is alkyl of 1-6 carbon atoms;
R$^5$ is cyano, fluoro, chloro or bromo;
R$^8$ is a divalent cycloalkyl of 3 to 7 carbon atoms, which may be optionally further substituted with one or more alkyl of 1 to 6 carbon atom groups; or is a divalent pyridinyl, pyimidinyl, or phenyl ring, wherein the pyridinyl, pyrimidinyl, or phenyl ring may be optionally further substituted with one or more groups selected from halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, and benzoylamino;

X is selected from —NH—, —O—, —S—, —CH$_2$— or —NR$^{7'}$— where R$^{7'}$ is alkyl of 1-6 carbon atoms;
m and p are independently selected from 0, 1, 2 or 3
R$^{10}$ is an optionally substituted arylene, optionally substituted C$_{3-10}$cycloalkylene ring or optionally substituted divalent heterocyclic ring or an N-oxide of any nitrogen containing ring, -Z- is a direct bond or a group, of sub-formula (i)

—X$^{12}$—R$^{75}$—X$^{13}$—R$^{76}$—X$^{14}$—(R$^{77}$—X$^{15}$)$_s$—  (i)

where X$^{12}$, X$^{13}$, X$^{14}$ and each X$^{15}$ are independently selected from —O—, —C(O)—, —S—, —SO—, —SO$_2$—, —NR$^{78}$C(O)—, —NR$^{78}$C(O)O—, —CONR$^{79}$—, —C(O)ONR$^{79}$—, —SO$_2$NR$^{80}$—, —NR$^{81}$SO$_2$— or —NR$^{82}$— (wherein R$^{78}$, R$^{79}$, R$^{80}$, R$^{81}$ and R$^{82}$ each independently represents hydrogen, C$_{1-3}$alkyl or C$_{1-3}$alkoxyC$_{2-3}$alkyl) and X$^{15}$ may additionally be a bond;
s is 0, 1, 2 or 3;
R$^{75}$, R$^{76}$ and R$^{77}$ are independently selected from C$_{1-6}$alkylene, C$_{2-6}$alkenylene or C$_{2-6}$alkynylene
and R$^9$ is an optionally substituted divalent heterocyclic group,
R$^6$ is a group of sub-formula (ii)

—X$^{16}$R$^{83}$—(X$^{17}$R$^{84}$)$_t$—X$^{18}$R$^{85}$  (ii)

where X$^{16}$, X$^{18}$ and each X$^{17}$ are each independently selected from a direct bond, —O—, —C(O)—, —S—, —SO—, —SO$_2$—, —NR$^{86}$C(O)—, —NR$^{86}$C(O)O—, —CONR$^{87}$—, —C(O)ONR$^{87}$—, —SO$_2$NR$^{88}$—, —NR$^{89}$SO$_2$— or —NR$^{90}$— (wherein R$^{86}$, R$^{87}$, R$^{88}$, R$^{89}$ and R$^{90}$ each independently represents hydrogen, C$_{1-3}$alkyl or C$_{1-3}$alkoxyC$_{2-3}$alkyl),
R$^{83}$ and each R$^{84}$ are independently selected from C$_{1-6}$alkylene, C$_{2-6}$alkenylene or C$_{2-6}$alkynylene,
R$^{85}$ is hydrogen, C$_{1-6}$alkyl, C$_{2-6}$alkenyl or C$_{2-6}$alkynyl,
t is 0, 1, 2 or 3,
provided that where the group of sub-formula (ii) is C$_{1-6}$alkyl, Z is other than a direct bond, and
R$^1$, R$^2$, R$^3$, R$^4$ are independently selected from hydrogen, hydroxy, halogeno, cyano, nitro, C$_{1-3}$alkyl, —NR$^{11}$R$^{12}$— (wherein R$^{11}$ and R$^{12}$, which may be the same or different each represents hydrogen, or C$_{1-3}$alkyl), or a group R$^{13}$—X$^1$—(CH$_2$), wherein x is 0 or an integer of from 1 to 3, X$^1$ represents a direct bond, —O—, —CH$_2$—, —OC(O)—, —C(O)—, —S—, —SO—, —SO$_2$—, —NR$^{14}$C(O)—, —NR$^{14}$C(O)O—, —C(O)NR$^{15}$—, —C(O)ONR$^{15}$—, SO$_2$NR$^{16}$—, —NR$^{17}$SO$_2$— or —NR$^{18}$— (wherein R$^{14}$, R$^{15}$, R$^{16}$, R$^{17}$ and R$^{18}$ each independently represents hydrogen, C$_{1-3}$alkyl or C$_{1-3}$alkoxyC$_{2-3}$alkyl)), and R$^{13}$ is hydrogen, optionally substituted hydrocarbyl, or optionally substituted heterocyclyl.

According to a second feature of the present invention there is provided a compound of formula (IA)

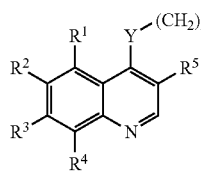

(IA)

or a pharmaceutically acceptable salt, pro-drug or solvate thereof wherein:

n is 0 or 1;

Y is selected from —NH—, —O—, —S—, or —NR$^7$— where R$^7$ is alkyl of 1-6 carbon atoms;

R$^5$ is cyano, fluoro, chloro or bromo;

R$^8$ is a divalent cycloalkyl of 3 to 7 carbon atoms, which may be optionally further substituted with one or more alkyl of 1 to 6 carbon atom groups; or is a divalent pyridinyl, pyrimidinyl, or phenyl ring, wherein the pyridinyl, pyrimidinyl, or phenyl ring may be optionally further substituted with one or more groups selected from halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkyanoylamino of 3-8 carbon atoms, and benzoylamino;

X is selected from —NH—, —O—, —S—, —CH$_2$— or —NR$^{7'}$— where R$^{7'}$ is alkyl of 1-6 carbon atoms;

m, p and q are independently selected from 0, 1, 2 or 3

R$^{10}$ is an optionally substituted arylene, optionally substituted C$_{3-10}$cycloalkylene ring or optionally substituted divalent heterocyclic ring or an N-oxide of any nitrogen containing ring, -Z- is a group of sub-formula (i)

—X$^{12}$—R$^{75}$—X$^{13}$—(R$^{76}$—X$^{14}$)$_s$—(R$^{77}$—X$^{15}$)$_{s'}$—  (i)

where X$^{12}$, X$^{13}$, each X$^{14}$ and each X$^{15}$ are independently selected from —O—, —C(O)—, —C(O)O—, —S—, —SO—, —SO$_2$—, —NR$^{78}$C(O)—, —NR$^{78}$C(O)O—, —CONR$^{79}$—, —C(O)ONR$^{79}$—, —SO$_2$NR$^{80}$—, —NR$^{81}$SO$_2$— or —NR$^{82}$— (wherein R$^{78}$, R$^{79}$, R$^{80}$, R$^{81}$ and R$^{82}$ each independently represents hydrogen, C$_{1-3}$alkyl optionally substituted by hydroxy, or C$_{1-3}$alkoxyC$_{2-3}$alkyl) and each X$^{13}$, X$^{14}$ and X$^{15}$ may additionally be a direct bond;

s and s' are independently selected from 0, 1, 2 or 3;

R$^{75}$ is group —C(R$^A$R$^B$)— where R$^A$ and R$^B$ are each independently selected from C$_{1-3}$ alkyl, C$_{2-3}$ alkenyl, C$_{2-3}$ alkynyl and halo;

R$^{76}$ and R$^{77}$ are independently selected from C$_{1-6}$alkylene, C$_{2-6}$alkenylene or C$_{2-6}$alkynylene optionally substituted by halo and hydroxy or R$^{76}$ or R$^{77}$ can each independently be a direct bond;

R$^9$ is an optionally substituted divalent heterocyclic group, C$_{1-5}$alkylene, or divalent C$_{3-7}$cycloalkyl;

R$^{106}$ is hydrogen, hydroxy, amino or a group of sub-formula (ii)

—X$^{16}$R$^{83}$—(X$^{17}$R$^{84}$)$_t$—X$^{18}$R$^{85}$  (ii)

where X$^{16}$, X$^{18}$ and each X$^{17}$ are each independently selected from a direct bond, —O—, —C(O)—, —S—, —SO—, —SO$_2$—, —NR$^{86}$C(O)—, —NR$^{86}$C(O)O—, —C(O)NR$^{87}$—, —C(O)ONR$^{87}$—, —SO$_2$NR$^{88}$—, —NR$^{89}$SO$_2$— or —NR$^{90}$— (wherein R$^{86}$, R$^{87}$, R$^{88}$, R$^{89}$ and R$^{90}$ each independently represents hydrogen, C$_{1-3}$alkyl or C$_{1-3}$alkoxyC$_{2-3}$alkyl);

R$^{83}$ and each R$^{84}$ are independently selected from C$_{1-6}$alkylene, C$_{2-6}$alkenylene or C$_{2-6}$-alkynylene;

R$^{85}$ is hydrogen, C$_{1-6}$alkyl, C$_{2-6}$alkenyl or C$_{2-6}$alkynyl, t is 0, 1, 2 or 3; and R$^1$, R$^2$, R$^3$, R$^4$ are independently selected from hydrogen, hydroxy, halogeno, cyano, nitro, trifluoromethyl, C$_{1-3}$alkyl, —NR$^{11}$R$^{12}$— (wherein R$^{11}$ and R$^{12}$, which may be the same or different each represents hydrogen, or C$_{1-3}$alkyl), 5-6-membered saturated heterocyclic group with 1-2 heteroatoms, selected independently from O, S and N, or a group R$^{13}$—X$^1$—(CH$_2$)$_x$ wherein x is 0 or an integer of from 1 to 3, X$^1$ represents a direct bond, —O—, —CH$_2$—, —OC(O)—, —C(O)—, —S—, —SO—, —SO$_2$—, —NR$^{14}$C(O)—, —NR$^{14}$C(O)O—, —C(O)NR$^{15}$—, —C(O)ONR$^{15}$—, —SO$_2$NR$^{16}$—, —NR$^{17}$SO$_2$— or —NR$^{18}$— (wherein R$^{14}$, R$^{15}$, R$^{16}$, R$^{17}$ and R$^{18}$ each independently represents hydrogen, C$_{1-3}$alkyl or C$_{1-3}$alkoxyC$_{2-3}$alkyl)), and R$^{13}$ is hydrogen, optionally substituted hydrocarbyl, or optionally substituted heterocyclyl.

According to a third feature of the present invention there is provided a compound of formula (IB)

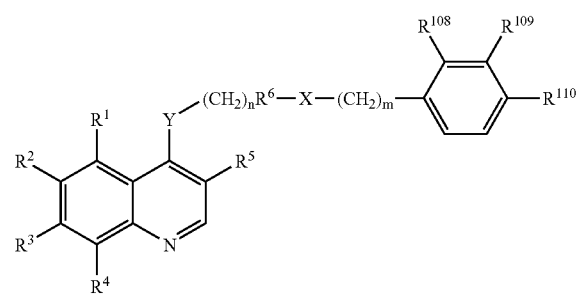

(IB)

or a pharmaceutically acceptable salt, prodrug or solvate thereof wherein:

n is 0 or 1;

Y is selected from —NH—, —O—, —S—, or —NR$^7$— where R$^7$ is alkyl of 1-6 carbon atoms;

R$^5$ is cyano, fluoro, chloro or bromo;

R$^6$ is a divalent cycloalkyl of 3 to 7 carbon atoms, which may be optionally further substituted with one or more alkyl of 1 to 6 carbon atom groups; or is a divalent pyridinyl, pyimidinyl, or phenyl ring, wherein the pyridinyl, pyrimidinyl or phenyl ring may be optionally further substituted with one or more groups selected from halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, and benzoylamino;

X is selected from —NH—, —O—, —S—, —CH$_2$— or NR$^{107'}$— where R$^{107'}$ is alkyl of 1-6 carbon atoms;

m is 0, 1, 2 or 3

R$^{108}$ and R$^{109}$ together with the carbon atoms to which they are attached form a fused 5 or 6 membered heteroaryl or heterocyclic ring;

R$^{110}$ is hydrogen or a group X'R$^{110'}$ where X' is NH—, —O—, —S—, —NR$^{107''}$— where R$^{107''}$ is alkyl of 1-6 carbon atoms and R$^{110'}$ is an optionally substituted alkyl;

R$^1$, R$^2$, R$^3$, R$^4$ are independently selected from hydrogen, hydroxy, halogeno, cyano, nitro, trifluoromethyl, C$_{1-3}$alkyl, —NR$^{11}$R$^{12}$— (wherein R$^{11}$ and R$^{12}$, which may be the same or different each represents hydrogen, or C$_{1-3}$alkyl), 5-6-membered saturated heterocyclic group with 1-2 heteroatoms, selected independently from O, S and N, or a group R$^{13}$—X$^1$—(CH$_2$)$_x$ wherein x is 0 or an integer of from 1 to 3, X$^1$ represents a direct bond, —O—, —CH$_2$—, —OC(O)—, —C(O)—, —S—, —SO—, —SO$_2$—, —NR$^{14}$C(O)—, —NR$^{14}$C(O)O—, —C(O) NR$^{15}$—, —C(O)ONR$^{15}$—, —SO$_2$NR$^{16}$—, —NR$^{17}$SO$_2$— or —NR$^{18}$— (wherein R$^{14}$, R$^{15}$, R$^{16}$, R$^{17}$ and R$^{18}$ each independently represents hydrogen, C$_{1-3}$alkyl or C$_{1-3}$alkoxyC$_{2-3}$alkyl), and R$^{13}$ is hydrogen, optionally substituted hydrocarbyl, or optionally substituted heterocyclyl;

provided that:
i) when R$^{108}$ and R$^{109}$ together with the phenyl group form benzofuran, where the heteroatom containing ring is substituted with one or more groups independently selected from C$_{1-6}$ alkyl, halo, hydroxyl, halo, —NR$^{119}$R$^{120}$, C(O)NR$^{119}$R$^{120}$ wherein R$^{119}$ and R$^{120}$, which may be the same or different, each represent hydrogen or C$_{1-4}$ alkyl or C$_{1-4}$ cycloalkyl; or
ii) when R$^{108}$ and R$^{109}$ together with the phenyl group form benzodihydrofuran or benzoxazole, the heteratom containing ring is substituted with one or more groups independently selected from halo, hydroxyl, halo, —NR$^{119}$R$^{120}$, —C(O)NR$^{119}$R$^{120}$ wherein R$^{119}$ and R$^{120}$, which may be the same or different, each represent hydrogen or C$_{1-4}$ alkyl or C$_{1-4}$ cycloalkyl.

In the compounds of formula (IB), R$^{108}$ and R$^{109}$ together with the phenyl to which they are attached preferably from a group selected from benzofuran, indole and quinoline. The indole and quinoline are optionally substituted with one or more groups independently selected from C$_{1-6}$ alkyl, halo, hydroxyl, halo, —NR$^{119}$R$^{120}$, C(O)NR$^{119}$R$^{120}$ wherein R$^{119}$ and R$^{120}$ which may be the same or different each represent hydrogen or C$_{1-4}$ alkyl or C$_{1-4}$ cycloalkyl. Preferably the substituent on the benzofuran or indole is —C(O)NR$^{119}$R$^{120}$ wherein R$^{119}$ and R$^{120}$ which may be the same or different each represent hydrogen or C$_{1-4}$ alkyl or C$_{1-4}$ cycloalkyl. More preferably in the group of formula —C(O)NR$^{119}$R$^{120}$, R$^{119}$ is hydrogen and R$^{120}$ is selected from —CH$_3$, —C(CH$_3$)$_2$ and cyclopropyl.

In this specification the term 'alkyl' when used either alone or as a suffix includes straight chained, branched structures. Unless otherwise stated, these groups may contain up to 10, preferably up to 6 and more preferably up to 4 carbon atoms.

Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as "alkoxy" comprise alkyl groups as is understood in the art.

The term "halo" or "halogeno" includes fluoro, chloro, bromo and iodo. References to aryl groups include aromatic carbocyclic groups such as phenyl and naphthyl. The term "heterocyclyl" or "heterocyclic" includes aromatic or non-aromatic rings, for example containing from 4 to 20, suitably from 5 to 8 ring atoms, at least one of which, and preferably from 1-4 of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl. Examples of non-aromatic heterocyclyl groups include morpholino, piperidino, azetidine, tetrahydrofuryl, tetrahydropyridyl. In the case of bicyclic rings, these may comprise an aromatic and non-aromatic portion.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. The moiety may be saturated or unsaturated. For example, these may be alkyl, alkenyl, alkynyl, aryl, aralkyl, cycloalkyl, cycloalkenyl or cycloalkynyl, or combinations thereof.

Examples of such combinations are alkyl, alkenyl or alkynyl substituted with aryl, aralkyl, cycloalkyl, cycloalkenyl or cycloalkynyl, or an aryl, heterocyclyl, alkoxy, aralkyl, cycloalkyl, cycloalkenyl or cycloalkynyl substituted with alkyl, alkenyl, alkynyl or alkoxy, but others may be envisaged.

In particular hydrocarbyl groups include alkyl, alkenyl, alkynyl, aryl, aralkyl, cycloalkyl, cycloalkenyl or cycloalkynyl.

The term "interposed" used in relation to heteroatoms in hydrocarbyl chains means that the chains include a heteroatom such as sulphur, oxygen or nitrogen either at an intermediate position along their length or at an end of the chain.

The term "interposed" used in relation to heterocyclic rings in hydrocarbyl chains means that the chains include a heterocyclic ring either at an intermediate position along their length or at an end of the chain.

Suitable pharmaceutically acceptable salts of compounds of formula (I), or (IA) or (MB) include acid addition salts such as methanesulfonate, fumarate, hydrochloride, hydrobromide, citrate, maleate and salts formed with phosphoric and sulphuric acid. A preferred pharmaceutically acceptable salt is a hydrochloride salt.

Thus, the alkyl portion of the alkyl, alkoxy, alkanoyloxy, alkoxymethyl, alkanoyloxymethyl, alkylsuphinyl, alkylsulphonyl, alkylsulfonamido, carboalkoxy, carboalkyl, alcanoylamidno aminoalkyl, alkylaminoalkyl, N,N-dicycloalkylaminoalkyl, hydroxyalkyl, and alkoxyalkyl substituents include both straight chain as well as branched carbon chains. The cycloalkyl portions of N-cycloalkyl-N-alkylaminoalkyl and N,N-dicycloalkylaminoalkyl substituents include both simple carbocycles as well as carbocycles containing alkyl substituents. The alkenyl portion of the alkenyl, alkenoyloxymethyl, alkenyloxy, alkenylsulfonamido, substituents include both straight chain as well as branched carbon chains and one or more sites of unsaturation. The alkynyl portion of the alkynyl, alkynoyloxymethyl alkynylsulfonamido, alkynyloxy, substituents include both straight chain as well as branched carbon chains and one or more sites of unsaturation. Carboxy is defined as a —$CO_2H$ radical. Carboalkoxy of 2-7 carbon atoms is defined as a —$CO_2R''$ radical, where R'' is an alkyl radical of 1-6 carbon atoms. Carboalkyl is defined as a —COR'' radical, where R'' is an alkyl radical of 1-6 carbon atoms. Alkanoyloxy is defined as a —OCOR'' radical, where R'' is an alkyl radical of 1-6 carbon atoms. Alkanoyloxymethyl is defined as R''$CO_2CH_2$— radical, where R'' is an alkyl radical of 1-6 carbon atoms. Alkoxymethyl is defined at R''$OCH_2$— radical, where R'' is an alkyl radical of 1-6 carbon atoms. Alkylsulphinyl is defined as R''SO— radical, where R'' is an alkyl radical of 1-6 carbon atoms. Alkylsulphonyl is defined as R''$SO_2$ radical, where R'' is alkyl radical of 1-6 carbon atoms. Alkylsulfonamido, alkenylsulfonamido, alkynylsulfonamido are defined as R''$SO_2$NH— radical, where R'' is an alkyl radical of 1-6 carbon atoms, an alkenyl radical of 2-6 carbon atoms, or an alkynyl radical of 2-6 carbon atoms, respectively. N-alkylcarbamoyl is defined as R''NHCO— radical, where R'' is an alkyl radical of 1-6 carbon atoms. N,N-dialkylcarbamoyl is defined as R''R'NCO— radical, where R'' is an alkyl radical of 1-6 carbon atoms, R' is an alkyl radical of 1-6 carbon atoms and R', and R'' may be the same or different. When X is substituted, it is preferred that it is mono-, di-, or tri-substituted, with monosubstituted being most preferred. It is preferred that of the substituents, $R_1$, $R_2$, $R_3$ and $R_4$ at least one is hydrogen and it is most preferred that two or three be hydrogen. An azacycloalkyl-N-alkyl substituent refers to a monocyclic heterocycle that contains a nitrogen atom on which is substituted a straight or branched chain alkyl radical. A morpholino-N-alkyl substituent is a morpholine ring substituted on the nitrogen atom with a straight or branch chain alkyl radical. A pipeazino-N-alkyl substituent is a piperazine ring substituted on one of the nitrogen atoms with a straight or branch chain alkyl radical. A N-alkyl-piperidino-N-alkyl substituent is a piperidine ring substituted on one of the nitrogen atoms with a straight or branched chain alkyl group and on the other nitrogen atom with a straight or branch chain alkyl radical.

When any group contains an alkyl portion, the alkyl portion contains preferably 1-6 carbon atoms, more preferably 1-4 carbon atoms, particularly methyl, ethyl, n-propyl, iso-propyl, n-butyl, iso-butyl, sec-butyl or tert-butyl. When any group contains an alkenyl or alkynyl portion, the alkenyl or alkynyl portion contains preferably 2-6 carbon atoms, more preferably 2-4 carbon atoms.

The compounds of this invention may contain an asymmetric carbon; in such cases, the compounds of this invention cover the racemate and the individual R and S entantiomers, and in the case were more than one asymmetric carbon exists, the individual diastereomers, their racemates and individual entantiomers.

Preferably $R^1$, $R^2$, $R^3$ and $R^4$ are each independently selected from hydrogen, hydroxy, halogeno, cyano, nitro, trifluoromethyl, $C_{1-3}$alkyl, —$NR^{11}R^{12}$ (wherein $R^{11}$ and $R^{12}$, which may be the same or different, each represents hydrogen or $C_{1-3}$alkyl), a 5 or 6 membered saturated heterocyclic group with one or two heteroatoms, selected independently from O, S and N, or a group $R^{13}$—$X^1$—$(CH_2)_x$ wherein x is 0 to 3, $X^1$ represents —O—, —$CH_2$—, —OCO—, carbonyl, —S—, —SO—, —$SO_2$—, —$NR^{14}C(O)$—, —$C(O)NR^{15}$—, —$SO_2NR^{16}$—, —$NR^{17}SO_2$— or —$NR^{18}$— (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl) and $R^{13}$ is selected from one of the following sixteen groups:

1) $C_{1-5}$alkyl which may be unsubstituted or which may be substituted with one or more groups selected from hydroxy, fluoro, chloro, cyano and amino;
2) $C_{1-5}$alkyl$X^2COR^{19}$ (wherein $X^2$ represents —O— or —$NR^{20}$— (wherein $R^{20}$ represents hydrogen, $C_{1-3}$alkyl or $C_{1-3}$alkoxy$C_{2-3}$alkyl) and $R^{19}$ represents —$NR^{21}R^{22}$— or —$OR^{23}$— (wherein $R^{21}$, $R^{22}$ and $R^{23}$ which may be the same or different each represents hydrogen, $C_{1-3}$alkyl or $C_{1-3}$alkoxy$C_{2-3}$alkyl));
3) $C_{1-5}$alkyl$X^3R^{24}$ (wherein $X^3$ represents —O—, —S—, —SO—, —$SO_2$—, —OCO—, —CO—O—, —$NR^{25}CO$—, —$CONR^{26}$—, —$SO_2NR^{27}$—, —$NR^{28}SO_2$— or —$NR^{29}$— and $C_{1-5}$alkyl optionally substituted by hydroxy (wherein $R^{25}$, $R^{26}$, $R^{27}$, $R^{28}$ and $R^{29}$ each independently represents hydrogen, $C_{1-3}$alkyl optionally substituted by hydroxy or $C_{1-3}$alkoxy$C_{2-3}$alkyl) and $R^{24}$ represents hydrogen, amino optionally substituted by $C_{1-5}$alkoxycarbonyl, $C_{1-5}$alkyl, $C_{3-6}$cycloalkyl, phenyl or a 5 or 6 membered saturated heterocyclic group with one or two heteroatoms, selected independently from O, S and N, which $C_{1-5}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);
4) $C_{1-5}$alkyl$X^4C_{1-5}$alkyl$X^5R^{30}$ (wherein $X^4$ and $X^5$ which may be the same or different are each —O—, —S—, —SO—, —$SO_2$—, —$NR^{31}CO$—, —$CONR^{32}$—, —$SO_2NR^{33}$—, —$NR^{34}SO_2$— or —$NR^{35}$— (wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl) and $R^{30}$ represents hydrogen, $C_{1-4}$alkanoyl or $C_{1-3}$alkyl optionally substituted by hydroxy);
5) $C_{1-5}$alkyl$R^{36}$ (wherein $R^{36}$ is $C_{3-6}$cycloalkyl or a 4, 5 or 6 membered saturated heterocyclic group with one or two heteroatoms, selected independently from O, S and N, which $C_{3-6}$cycloalkyl and heterocyclic group may bear one or two substituents selected from oxo, hydroxy, halogeno, $C_{1-4}$alkyl, $C_{1-4}$hydroxyalkyl, $C_{1-4}$alkoxy, $C_{2-5}$alkenyl, hydroxy$C_{2-5}$alkenyl, $C_{2-5}$alkynyl, $C_{1-5}$alkanoyl, $C_{1-5}$alkoxycarbonyl, $C_{1-3}$alkanoyl$C_{1-3}$alkyl, $C_{1-3}$alkoxy$C_{1-3}$alkyl, $C_{1-5}$alkylthio, $C_{1-5}$alkylsulphanyl, $C_{1-5}$alkylsulphonyl, aryl, hydroxy$C_{1-5}$alkoxy, nitro, amino, amino$C_{1-5}$alkyl, guanidino, N—$C_{1-5}$alkylamino, N,N-di-$C_{1-5}$alkylamino, carboxy, cyano, cyano$C_{1-5}$alkyl, —$CONR^zR^{z'}$— and —$NR^{z''}CO$— (wherein $R^z$, $R^{z'}$ and $R^{z''}$ each independently represent hydrogen, $C_{1-5}$alkyl or $C_{1-3}$alkoxy$C_{1-3}$alkyl);
6) $(CH_2)_qX^6R^{37}$ (wherein q is an integer from 0 to 5, $X^6$ represents a direct bond, —O—, —S—, —SO—, —$SO_2$—, —$NR^{38}CO$—, —$CONR^{39}$—, CO—O—, —$SO_2NR^{40}$—, —$NR^{41}SO_2$— or —$NR^{42}$— (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{37}$ is $C_{1-5}$alkoxy, a phenyl group, a benzyl group, a pyridone group or a 5 or 6 membered aromatic heterocyclic group with 1 to 3 heteroatoms selected from O, N and S, which phenyl, benzyl, pyridone or aromatic heterocyclic group may carry up to 5 substituents selected from hydroxy, halogeno, nitro, amino, N—$C_{1-5}$alkylamino, N,N-di-$C_{1-5}$alkylamino, guanidino, $C_{1-4}$alkyl, $C_{1-4}$alkoxy, $C_{1-4}$hydroxyalkyl, $C_{1-4}$hydroxyalkoxy, $C_{1-4}$aminoalkyl, $C_{1-4}$alkylamino, carboxy, cyano, cyano$C_{1-5}$alkyl, $C_{2-5}$alkenyl, hydroxy$C_{2-5}$alkenyl, $C_{2-5}$alkynyl, $C_{1-5}$alkanoyl, $C_{1-5}$alkoxycarbonyl, $C_{1-3}$alkanoyl$C_{1-3}$alkyl, $C_{1-3}$alkoxy$C_{1-3}$alkyl, $C_{1-5}$alkylthio, $C_{1-5}$alkylsulphanyl, $C_{1-5}$alkylsulphonyl, aryl, —$CONR^{43}R^{44}$ and —NR$^{45}$COR$^{46}$ (wherein R$^{43}$, R$^{44}$, R$^{45}$ and R$^{46}$, which may be the same or different, each represents hydrogen, C$_{1-4}$alkyl or C$_{1-3}$alkoxyC$_{2-3}$alkyl));

7) C$_{2-6}$alkenylR$^{36}$ (wherein R$^{36}$ is as defined hereinbefore);
8) C$_{2-6}$alkynylR$^{36}$ (wherein R$^{36}$ is as defined hereinbefore);
9) X$^7$R$^{47}$ (wherein X$^7$ is —SO$_2$—, —O— or —CONR$^{48}$R$^{49}$— (wherein R$^{48}$ and R$^{49}$, which may be the same or different, each represents hydrogen, C$_{1-3}$alkyl or C$_{1-3}$alkoxyC$_{2-3}$alkyl) and R$^{47}$ represents C$_{1-5}$alkyl which may be unsubstituted or which may be substituted with one or more groups selected from hydroxy, fluoro and amino) with the provisos that when X$^7$ is —SO$_2$—, X$^1$ is —O—; when X$^7$ is —O—, X$^1$ is carbonyl; or when X$^7$ is —CONR$^{48}$R$^{49}$—, X$^1$ is —O— or NR$^{18}$ (wherein R$^{48}$, R$^{49}$ and R$^{18}$ are as defined hereinbefore);
10) C$_{2-6}$alkenylR$^{37}$ (wherein R$^{37}$ is as defined hereinbefore);
11) C$_{2-6}$alkynylR$^{37}$ (wherein R$^{37}$ is as defined hereinbefore);
12) C$_{2-4}$alkenylX$^8$R$^{37}$ (wherein X$^8$ represents —O—, —S—, —SO—, —SO$_2$—, —NR$^{50}$CO—, —CONR$^{51}$—, —SO$_2$NR$^{52}$—, —NR$^{53}$SO$_2$— or —NR$^{54}$— (wherein R$^{50}$, R$^{51}$, R$^{52}$, R$^{53}$ and R$^{54}$ each independently represents hydrogen, C$_{1-3}$alkyl or C$_{1-3}$alkoxyC$_{2-3}$alkyl) and R$^{37}$ is as defined hereinbefore);
13) C$_{2-6}$alkynylX$^9$R$^{37}$ (wherein X$^9$ represents —O—, —S—, —SO—, —SO$_2$—, —NR$^{55}$CO—, —CONR$^{56}$—, —SO$_2$NR$^{57}$—, —NR$^{58}$SO$_2$— or —NR$^{59}$— (wherein R$^{55}$, R$^{56}$, R$^{57}$, R$^{58}$ and R$^{59}$ each independently represents hydrogen, C$_{1-3}$alkyl or C$_{1-3}$alkoxyC$_{2-3}$alkyl) and R$^{37}$ is as defined hereinbefore);
14) C$_{1-3}$alkylX$^{10}$C$_{1-3}$alkylR$^{37}$ (wherein X$^{10}$ represents —O—, —S—, —SO—, —SO$_2$—, —NR$^{60}$CO—, —CON$^{61}$—, —SO$_2$NR$^{62}$—, —NR$^{63}$SO$_2$— or —NR$^{64}$— (wherein R$^{60}$, R$^{61}$, R$^{62}$, R$^{63}$ and R$^{64}$ each independently represents hydrogen, C$_{1-3}$alkyl or C$_{1-3}$alkoxyC$_{2-3}$alkyl) and R$^{37}$ is as defined hereinbefore);
15) R$^{36}$ (wherein R$^{36}$ is as defined hereinbefore); and
16) C$_{1-3}$alkylX$^{10}$C$_{1-3}$alkylR$^{36}$ (wherein X$^{10}$ and R$^{36}$ are as defined hereinbefore).

In particular R$^1$, R$^2$, R$^3$ and R$^4$ are selected from hydrogen, hydroxy, halogeno, cyano, nitro, trifluoromethyl, C$_{1-3}$alkyl, —NR$^{11}$R$^{12}$— (wherein R$^{11}$ and R$^{12}$ are as defined above), or R$^{13}$X$^1$—(CH$_2$)$_x$— (wherein x is 0 or an integer of from 1-3, X$^1$ represents a direct bond, —O—, —CH$_2$—, —OC(O)—, —C(O)—, —S—, —SO—, —SO$_2$—, —NR$^{14}$C(O)—, —NR$^{14}$C(O)O—, —C(O)NR$^{15}$—, —C(O)ONR$^{15}$—, —SO$_2$NR$^{16}$—, —NR$^{17}$SO$_2$— or —NR$^{18}$— (wherein R$^{14}$, R$^{15}$, R$^{16}$, R$^{17}$ and R$^{18}$ each independently represents hydrogen, C$_{1-3}$alkyl or C$_{1-3}$alkoxyC$_{2-3}$alkyl)), and R$^{13}$ is any one of the following twenty-two groups 1') C$_{1-5}$alkyl which may be unsubstituted or which may be substituted with one or more groups selected from hydroxy, oxiranyl, fluoro, chloro, bromo and amino (including C$_{1-3}$alkyl and trifluoromethyl);
2') —R$^a$X$^2$C(O)R$^{19}$ (wherein X$^2$ represents —O— or —NR$^{20}$— (in which R$^{20}$ represents hydrogen, C$_{1-3}$alkyl or C$_{1-3}$alkoxyC$_{2-3}$alkyl) and R$^{19}$ represents C$_{1-3}$alkyl, —NR$^{21}$R$^{22}$ or —OR$^{23}$ (wherein R$^{21}$, R$^{22}$ and R$^{23}$ which may be the same or different each represents hydrogen, C$_{1-5}$alkyl. hydroxyC$_{1-5}$alkyl or C$_{1-3}$alkoxyC$_{2-3}$alkyl));
3') —R$^b$X$^3$R$^{24}$ (wherein X$^3$ represents —O—, C(O)—S—, —SO—, —SO$_2$—, —OC(O)—, —NR$^{25}$C(O)—, —NR$^{25}$C(O)O—, —C(O)NR$^{26}$—, —C(O)ONR$^{26}$—, —SO$_2$NR$^{27}$—, —NR$^{28}$SO$_2$— or —NR$^{29}$— (wherein R$^{25}$, R$^{26}$, R$^{27}$, R$^{28}$ and R$^{29}$ each independently represents hydrogen, C$_{1-3}$alkyl, hydroxy C$_{1-4}$alkyl or C$_{1-3}$alkoxyC$_{2-3}$alkyl and R$^{24}$ represents hydrogen, C$_{1-6}$alkyl, C$_{2-6}$alkenyl, cyclopropyl, cyclobutyl, cyclopentyl, cyclohexyl, phenyl or a 5-6-membered saturated heterocyclic group with 1-2 heteroatoms, selected independently from O, S and N, which C$_{1-6}$alkyl group may bear 1, 2 or 3 substituents selected from oxo, hydroxy, halogeno, cyclopropyl, amino, C$_{1-4}$alkylamino, C$_{1-4}$alkanoyldi-C$_{1-4}$alkylamino, C$_{1-4}$alkylthio, C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(R$^{b'}$)$_g$D (wherein f is 0 or 1, g is 0 or 1 and D is a C$_{3-6}$cycloalkyl group or a 5-6-membered saturated heterocyclic group with 1-2 heteroatoms, selected independently from O, S and N, which cyclic group may bear one or more substituents selected from C$_{1-4}$alkyl));
4') —R$^c$X$^4$R$^{c'}$X$^5$R$^{30}$ (wherein X$^4$ and X$^5$ which may be the same or different are each —O—, C(O), —S—, —SO—, —SO$_2$—, —NR$^{31}$C(O)—, —NR$^{31}$C(O)O—, —C(O)NR$^{32}$—, —C(O)ONR$^{32}$—, —SO$_2$NR$^{33}$—, —NR$^{34}$SO$_2$— or —NR$^{35}$— (wherein R$^{31}$, R$^{32}$, R$^{33}$, R$^{34}$ and R$^{35}$ each independently represents hydrogen, C$_{1-3}$alkyl or C$_{1-3}$alkoxyC$_{2-3}$alkyl and R$^{30}$ represents hydrogen, C$_{1-3}$alkyl, hydroxyC$_{1-3}$alkyl or C$_{1-3}$alkoxyC$_{2-3}$alkyl);
5') R$^d$R$^{36}$ (wherein R$^{36}$ is a 4-6-membered cycloalkyl or saturated heterocyclic ring (linked via carbon or nitrogen) with 1-2 heteroatoms, selected independently from O, S and N, which cycloalkyl or heterocyclic group may bear 1 or 2 substituents selected from oxo, hydroxy, halogeno, cyano, C$_{1-4}$alkyl, hydroxyC$_{1-4}$alkyl, cyanoC$_{1-4}$alkyl, cyclopropyl, C$_{1-4}$alkylsulphonylC$_{1-4}$alkyl, C$_{1-4}$alkoxycarbonyl, carboxamido, C$_{1-4}$aminoalkyl, C$_{1-4}$alkylamino, di(C$_{1-4}$alkyl)amino, C$_{1-4}$alkylaminoC$_{1-4}$alkyl, C$_{1-4}$alkanoyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy nitro, amino, C$_{1-4}$alkoxy, C$_{1-4}$hydroxyalkoxy, carboxy, trifluoromethyl, cyano, —C(O)NR$^{65}$R$^{66}$, —NR$^{67}$C(O)R$^{68}$ (wherein R$^{65}$, R$^{66}$, R$^{67}$ and R$^{68}$, which may be the same or different, each represents hydrogen, C$_{1-4}$alkyl, hydroxyC$_{1-4}$alkyl or C$_{1-3}$alkoxyC$_{2-3}$alkyl) and a group —(—O—)$_f$(R$^{b'}$)$_g$ringD (wherein f is 0 or 1, g is 0 or 1 and ring D is a cyclic group selected from C$_{3-6}$cycloalkyl, aryl or 5-6-membered saturated or unsaturated heterocyclic group with 1-2 heteroatoms, selected independently from O, S and N, which cyclic group may bear one or more substituents selected from halo and C$_{1-4}$alkyl);
6') R$^e$X$^6$R$^{37}$ (wherein X$^6$ represents a direct bond, —O—, —C(O)—, —S—, —SO—, —SO$_2$—, —NR$^{38}$CO—, —NR$^{38}$C(O)O—, —CONR$^{39}$—, —C(O)ONR$^{39}$—, —SO$_2$NR$^{40}$—, —NR$^{41}$SO$_2$— or NR$^{42}$— (wherein R$^{38}$, R$^{39}$, R$^{40}$, R$^{41}$ and R$^{42}$ each independently represents hydrogen, C$_{1-3}$alkyl or C$_{1-3}$alkoxyC$_{2-3}$alkyl) and R$^{37}$ is a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from hydroxy, nitro, halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, oxo, cyanoC$_{1-4}$alkyl, cyclopropyl, C$_{1-4}$alkylsulphonylC$_{1-4}$alkyl, C$_{1-4}$alkoxycarbonyl, di(C$_{1-4}$alkyl)amino, C$_{1-4}$alkylaminoC$_{1-4}$alkyl, C$_{1-4}$alkanoyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy, carboxy, carboxamido, trifluoromethyl, cyano, —C(O)NR$^{43}$R$^{44}$, —NR$^{45}$C(O)R$^{46}$ (wherein R$^{43}$, R$^{44}$, R$^{45}$ and R$^{46}$, which may be the same or different, each represents hydrogen, $C_{1-4}$alkyl, hydroxy$C_{1-4}$alkyl or $C_{1-3}$alkoxy$C_{2-3}$alkyl) and a group —(—O—)$_f$R$^{b'}$)$_g$ringD (wherein f is 0 or 1, g is 0 or 1 and ring D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl);

7') —R$^f$R$^{36}$ (wherein R$^{36}$ is as defined in (5') hereinbefore);
8') —R$^g$R$^{36}$ (wherein R$^{36}$ is as defined in (5') hereinbefore);
9') X$^7$R$^{47}$ (wherein X$^7$ is —SO$_2$—, —O— or —CONR$^{48}$R$^{49}$— (wherein R$^{48}$ and R$^{49}$, which may be the same or different, each represents hydrogen, $C_{1-3}$alkyl or $C_{1-3}$alkoxy$C_{2-3}$alkyl) and R$^{47}$ represents $C_{1-5}$alkyl which may be unsubstituted or which may be substituted with one or more groups selected from hydroxy, fluoro and amino) with the provisos that when X$^7$ is —SO$_2$—, X$^1$ is —O—, when X$^7$ is —O—, X$^1$ is carbonyl, when X$^7$ is —CONR$^{48}$R$^{49}$—, X$^1$ is —O— or NR$^{18}$ (wherein R$^{48}$, R$^{49}$ and R$^{18}$ are as defined in (6') hereinbefore);
10') —R$^h$R$^{37}$ (wherein R$^{37}$ is as defined in (6') hereinbefore);
11') —R$^j$R$^{37}$ (wherein R$^{37}$ is as defined in (6') hereinbefore);
12') —R$^j$X$^8$R$^{37}$ (wherein X$^8$ represents —O—, —C(O)—, —S—, —SO—, —OC(O)—, —NR$^{50}$C(O)—, —NR$^{50}$C(O)O—, —C(O)NR$^{51}$—, —C(O)ONR$^{51}$—, —SO$_2$NR$^{52}$—, —NR$^{13}$SO$_2$— or —NR$^{54}$— (wherein R$^{50}$, R$^{51}$, R$^{52}$, R$^{53}$ and R$^{54}$ each independently represents hydrogen, $C_{1-3}$alkyl, hydroxy$C_{1-3}$alkyl or $C_{1-3}$alkoxy$C_{2-3}$alkyl) and R$^{37}$ is as defined in (6') hereinbefore);
13') —R$^k$R$^9$R$^{37}$ (wherein X$^9$ represents —O—, C(O), —S—, —SO—, —SO$_2$—, —NR$^{55}$C(O)—, —NR$^{55}$C(O)O—, —C(O)NR$^{56}$—, —C(O)ONR$^{56}$—, —SO$_2$NR$^{57}$—, —NR$^{58}$SO$_2$— or —NR$^{59}$— (wherein R$^{55}$, R$^{56}$, R$^{57}$, R$^{58}$ and R$^{49}$ each independently represents hydrogen, $C_{1-3}$alkyl, hydroxy$C_{1-3}$alkyl or $C_{1-3}$alkoxy$C_{2-3}$alkyl) and R$^{37}$ is as defined in (6') hereinbefore);
14') —R$^m$X$^{10}$R$^{m'}$R$^{37}$ (wherein X$^{10}$ represents —O—, —C(O)—, —S—, —SO—, —SO$_2$—, —NR$^{60}$C(O)—, —NR$^{60}$C(O)O—, —C(O)NR$^{61}$—, —C(O)ONR$^{61}$—, —SO$_2$NR$^{62}$—, —NR$^{63}$SO$_2$— or —NR$^{64}$— (wherein R$^{60}$, R$^{61}$, R$^{62}$, R$^{63}$ and R$^{64}$ each independently represents hydrogen, $C_{1-3}$alkyl, hydroxy$C_{1-3}$alkyl or $C_{1-3}$alkoxy$C_{2-3}$alkyl) and R$^{37}$ is as defined in (6') hereinbefore);
15') R$^{36}$ (where R$^{36}$ is as defined in (5') hereinbefore);
16') —R$^n$X$^{10}$R$^{n'}$R$^{36}$ (wherein X$^{10}$ is as defined in (14') above and R$^{36}$ is as defined in (5') hereinbefore);
17') —R$^p$X$^{10}$—R$^{p'}$R$^{37}$ (wherein X$^{10}$ is as defined in (14') above and R$^{37}$ are as defined in (6') hereinbefore);
18') $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
19') $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
20') —R$_t$X$^{10}$R$^{t'}$R$^{36}$ (wherein X$^{10}$ is as defined in (14') above and R$^{36}$ is as defined in (5') hereinbefore);
21') —R$^u$X$^{10}$R$^{u'}$R$^{36}$ (wherein X$^{10}$ is as defined in (14') above and R$^{36}$ is as defined in (5') hereinbefore); and
22') —R$^v$R$^{69}$(R$^{v'}$)$_{q'}$(X$^{10}$)$_r$R$^{70}$ (wherein X$^{10}$ is as defined in (14') above, q' is 0 or 1, r is 0 or 1, and R$^{69}$ is a $C_{1-3}$alkylene group or a cyclic group selected from cyclopropyl, cyclobutyl, cyclopentylene, cyclohexylene or a 5-6-membered saturated heterocyclic group with 1-2 heteroatoms, selected independently from O, S and N, which $C_{1-3}$alkylene group may bear 1 or 2 substituents selected from oxo, hydroxy, halogeno and $C_{1-4}$alkoxy and which cyclic group may bear 1 or 2 substituents selected from oxo, hydroxy, halogen, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, i($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$(R$^{b'}$)$_g$ringD (wherein f is 0 or 1, g is 0 or 1 and ring D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl); and R$^{70}$ is hydrogen, $C_{1-3}$alkyl, or a cyclic group selected from cyclopropyl, cyclobutyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$(R$^{b'}$)$_g$ringD (wherein f is 0 or 1, g is 0 or 1 and D is a cyclic group selected from $C_{3-6}$cycloalkyl, aryl or 5-6-membered saturated or unsaturated heterocyclic group with 1-2 heteroatoms, selected independently from O, S and N, which cyclic group may bear one or more substituents selected from halo and $C_{1-4}$alkyl);
and wherein R$^a$, R$^b$, R$^{b'}$, R$^c$, R$^{c'}$, R$^d$, R$^e$, R$^i$, R$^m$, R$^{m'}$, R$^n$, R$^{n'}$, R$^{p'}$, R$^{t'}$, R$^{u'}$, R$^v$ and R$^{v'}$ are independently selected from $C_{1-4}$alkylene groups optionally substituted by one or more substituents selected from hydroxy, halogen, amino; and R$^e$ may additionally be a bond; and
R$^f$, R$^h$, R$^j$, R$^p$ and R$^t$ are independently selected from $C_{2-8}$alkenylene groups optionally substituted by one or more substituents selected from hydroxy, halogeno, amino, and R$^t$ may additionally be a bond; and
R$^g$, R$^k$, and R$^u$ are independently selected from by $C_{2-8}$alkynylene groups optionally substituted by one or more substituents selected from hydroxy, halogeno or amino.

In one embodiment, at least one group R$^1$, R$^2$, R$^3$ or R$^4$ is a group R$^{13}$—X$^1$—(CH$_2$)$_x$— (wherein x is 0 or an integer of from 1-3, X$^1$ represents —NR$^{14}$C(O)O—, or C(O)ONR$^{15}$—, (wherein R$^{13}$R$^{14}$ and R$^{15}$ are as defined above). A particular example of such a group for R$^1$, R$^2$, R$^3$ or R$^4$ is a group —NHC(O)OR$^{13}$ where R$^{13}$ is as defined above, and in particular is a group of formula (6') such as benzyl.

In particular, at least one group R$^1$, R$^2$, R$^3$ or R$^4$ is selected from R$^{13}$X$^1$—(CH$_2$)$_x$— (wherein x is 0 or an integer of from 1-3, X$^1$ represents a direct bond, —O—, —CH$_2$—, —OC(O)—, —C(O)—, —S—, —SO—, —SO$_2$—, —NR$^{14}$C(O)—, —NR$^{14}$C(O)O—, —C(O)NR$^{15}$—, —C(O)ONR$^{15}$—, —SO$_2$NR$^{16}$—, —NR$^{17}$SO$_2$— or —NR$^{18}$— (wherein R$^{14}$, R$^{15}$, R$^{16}$, R$^{17}$ and R$^{18}$ each independently represents hydrogen, $C_{1-3}$alkyl or $C_{1-3}$alkoxy$C_{2-3}$alkyl)), and R$^{13}$ is any one of the following twenty-two groups;

1'') $C_{1-5}$alkyl substituted with one or more groups selected from oxiranyl, chloro or bromo;

2") —R$^{a'}$X$^2$C(O)R$^{19}$ (wherein X$^2$ and R$^{19}$ are as defined in (2') above, and R$^{a'}$ is a C$_{1-8}$alkylene groups substituted by one or more substituents selected from hydroxy, halogeno, amino, 3") —R$^b$X$^3$R$^{24}$ (wherein either R$^{24}$ is any of the groups defined in (3') above and X$^3$ is —C(O), —NR$^{25}$C(O)O—, —C(O)ONR$^{26}$— (wherein R$^{25}$ and R$^{26}$ are as defined in (3') above), or X$^3$ is any other groups defined in (3') above and R$^{24}$ represents C$_{1-3}$alkyl, C$_{3-6}$alkyl, C$_{2-6}$alkenyl, cyclopropyl, cyclobutyl, cyclopentyl, cyclohexyl or phenyl, wherein (a) the C$_{3-6}$alkyl group may bear 1, 2 or 3 substituents selected from oxo, hydroxy, halogeno, cyclopropyl, amino, C$_{1-4}$alkylamino, C$_{1-4}$alkanoyldi-C$_{1-4}$alkylamino, C$_{1-4}$alkylthio, C$_{1-4}$alkoxy, (b) the C$_{1-3}$ alkyl group may be similarly substituted to the C$_{3-6}$alkyl provided it includes at least one substituent selected from cyclopropyl, amino, C$_{1-4}$alkylamino, C$_{1-4}$alkanoyldi-C$_{1-4}$alkylamino, C$_{1-4}$alkylthio, C$_{1-4}$alkoxy; (c) the cyclopropyl or cyclobutyl may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(R$^{b'}$)$_g$D (wherein f, g R$^{b'}$ and D are as defined above); (d) the cyclopentyl or cyclohexyl may be similarly substituted provided it includes at least one substituent selected from cyano, C$_{1-4}$cyanoalkyl, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(R$^{b'}$)$_g$D (wherein f, g R$^{b'}$ and D are as defined above), or X$^3$ and R$^{24}$ are any of the groups defined in 3' above and R$^b$ is other than C$_{1-5}$alkylene;

4") —R$^c$R$^4$R$^{c'}$X$^5$R$^{30}$ (wherein R$^c$, R$^{c'}$ and R$^{30}$ are as defined in (4') above and X$^4$ and X$^5$ are as defined above provided at least one of these is selected from C(O), —NR$^{31}$C(O)O—, or —C(O)ONR$^{32}$— (wherein R$^{31}$ and R$^{32}$ are as defined in (4') above), or X$^4$ and X$^5$ are any of the groups defined in (4') above, and either R$^{30}$ is hydroxyC$_{1-3}$alkyl or C$_{1-3}$alkoxyC$_{2-3}$alkyl), or at least one of R$^c$ or R$^{c'}$ is other than an unsubstituted C$_{1-5}$alkylene group;

5") R$^d$R$^{36}$ (wherein R$^d$ is as defined above, and R$^{36}$ is a 4-6-membered cycloalkyl or a saturated heterocyclic ring (linked via carbon or nitrogen including for example from 4 to 7 atoms) with 1-2 heteroatoms, selected independently from O, S and N, which cycloalkyl or heterocyclic group may bear 1 or 2 substituents listed in (5') above, provided that where R$^{36}$ is a 5 or 6 membered heterocyclic ring, either it carries at least one substituent selected from cyano, cyanoC$_{1-4}$alkyl, cyclopropyl, C$_{1-4}$alkylsulphonylC$_{1-4}$alkyl, C$_{1-4}$alkoxycarbonyl, carboxamido, C$_{1-4}$aminoalkyl, C$_{1-4}$alkylamino, di(C$_{1-4}$alkyl)amino, C$_{1-4}$alkylaminoC$_{1-4}$alkyl, C$_{1-4}$alkanoyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy nitro, amino, C$_{1-4}$hydroxyalkoxy, carboxy, trifluoromethyl, —C(O)NR$^{65}$R$^{66}$, —NR$^{67}$C(O)R$^{68}$ (wherein R$^{65}$, R$^{66}$, R$^{67}$ and R$^{68}$, are as defined in (5') above and a group —(—O—)$_f$(R$^{b'}$)$_g$ringD (wherein f, g, R$^{b'}$ and D are as defined above); R$^{36}$ is any of the groups defined in 5' above and R$^d$ is other than C$_{1-5}$alkyl;

6") R$^e$X$^6$R$^{37}$ (wherein R$^e$ and R$^{37}$ are any of the groups defined above, provided that X$^6$ represents —C(O)—, —NR$^{38}$C(O)O—, or —C(O)ONR$^{39}$—, (wherein R$^{38}$ and R$^{39}$ are as defined above) or, X$^6$ is any other group listed in (6') above, provided that either R$^{37}$ is a pyridone group, a phenyl group or a 5-6-membered aromatic heterocyclic group as (linked via carbon or nitrogen) with 1-3 heteroatoms selected from O, N and S, which pyridone, phenyl or aromatic heterocyclic group which is substituted as described in (6') provided it carries at least one substituent selected from nitro, amino, C$_{1-4}$hydroxyalkoxy, oxo, cyanoC$_{1-4}$alkyl, cyclopropyl, C$_{1-4}$alkylsulphonylC$_{1-4}$alkyl, C$_{1-4}$alkoxycarbonyl, di(C$_{1-4}$alkyl)amino, C$_{1-4}$alkylaminoC$_{1-4}$alkyl, C$_{1-4}$alkanoyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy, carboxamido, trifluoromethyl, or a group —(—O—)$_f$(R$^{b'}$)$_g$ringD (wherein f, g, R$^{b'}$ and D are as defined above) or R$^e$ is other than a direct bond or a C$_{1-5}$alkylene group;

7") —R$^f$R$^{36}$ (wherein R$^f$ and R$^{36}$ are as defined in (7') above provided that where R$^f$ is unsubstituted C$_{2-6}$ alkenylene, R$^{36}$ is as defined in (5") hereinbefore);

8") —R$^g$R$^{36}$ (wherein R$^g$ and R$^{36}$ are as defined in (8') above provided that where R$^g$ is unsubstituted C$_{2-6}$ alkynylene, R$^{36}$ is as defined in (5") hereinbefore);

10") —R$^h$R$^{37}$ (wherein R$^h$ and R$^{37}$ are as defined in (10') above provided that where R$^h$ is unsubstituted C$_{2-4}$ alkenylene, R$^{37}$ is R$^{37}$ is a pyridone group, a phenyl group or a 5-6-membered aromatic heterocyclic group as (linked via carbon or nitrogen) with 1-3 heteroatoms selected from O, N and S, which pyridone, phenyl or aromatic heterocyclic group which is substituted as described in (6') provided it carries at least one substituent selected from nitro, ammo, C$_{1-4}$hydroxyalkoxy, oxo, cyanoC$_{1-4}$alkyl, cyclopropyl, C$_{1-4}$alkylsulphonylC$_{1-4}$alkyl, C$_{1-4}$alkoxycarbonyl, di(C$_{1-4}$alkyl)amino, C$_{1-4}$alkylaminoC$_{1-4}$alkyl, C$_{1-4}$alkanoyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy, carboxamido, trifluoromethyl, or a group —(—O—)$_f$(R$^{b'}$)$_g$ringD (wherein f, g, R$^{b'}$ and D are as defined above));

11") —R$^i$R$^{37}$ (wherein R$^i$ and R$^{37}$ are as defined in (11') above provided that where R$^i$ is unsubstituted C$_{2-6}$ alkynylene, R$^{37}$R$^{37}$ is a pyridone group, a phenyl group or a 5-6-membered aromatic heterocyclic group as (linked via carbon or nitrogen) with 1-3 heteroatoms selected from O, N and S, which pyridone, phenyl or aromatic heterocyclic group which is substituted as described in (6') provided it carries at least one substituent selected from nitro, amino, C$_{1-4}$hydroxyalkoxy, oxo, cyanoC$_{1-4}$alkyl, cyclopropyl, C$_{1-4}$alkylsulphonylC$_{1-4}$alkyl, C$_{1-4}$alkoxycarbonyl, di(C$_{1-4}$alkyl)amino, C$_{1-4}$alkylaminoC$_{1-4}$alkyl, C$_{1-4}$alkanoyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy, carboxamido, trifluoromethyl, or a group —(—O—)$_f$R$^{b'}$)$_g$ringD (wherein f, g, R$^{b'}$ and D are as defined above);

12") —R$^j$X$^8$R$^{37}$ (wherein R$^j$ and R$^{37}$ are as defined in (12') above, and X$^8$ is —C(O)—, —NR$^{50}$C(O)O— or —C(O)ONR$^{51}$— (wherein R$^{50}$ and R$^{51}$ are as defined in (12') above, or X$^8$ is any other group listed in (12' above) and either R$^{37}$ is a pyridone group, a phenyl group or a 5-6-membered aromatic heterocyclic group as (linked via carbon or nitrogen) with 1-3 heteroatoms selected from O, N and S, which pyridone, phenyl or aromatic heterocyclic group which is substituted as described in (6') provided it carries at least one substituent selected from nitro, amino, C$_{1-4}$hydroxyalkoxy, oxo, cyanoC$_{1-4}$alkyl, cyclopropyl, C$_{1-4}$alkylsulphonylC$_{1-4}$alkyl, C$_{1-4}$alkoxycarbonyl, di(C$_{1-4}$alkyl)amino, C$_{1-4}$alkylaminoC$_{1-4}$alkyl, C$_{1-4}$alkanoyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy, carboxamido, trifluoromethyl, or a group —(—O—)$_f$(R$^{b'}$)$_g$ringD (wherein f, g, R$^{b'}$ and D are as defined above); or R$^j$ is other than unsubstituted C$_{2-6}$alkenylene;

13") —R$^k$X$^9$R$^{37}$ (wherein R$^k$ and R$^{37}$ are as defined in (13') above, and X$^9$ is —C(O)—, —NR$^{55}$C(O)O— or —C(O)ONR$^{56}$—, (wherein R$^{55}$ and R$^{56}$ are as defined in (13') above, or X$^9$ is any other group listed in (13' above) and either R$^{37}$ is a pyridone group, a phenyl group or a 5-6-membered aromatic heterocyclic group as (linked via carbon or nitrogen) with 1-3 heteroatoms selected from O, N and S, which pyridone, phenyl or aromatic heterocyclic group which is substituted as described in (6') provided it carries at least one substituent selected from nitro, amino, C$_{1-4}$hydroxyalkoxy, oxo, cyanoC$_{1-4}$alkyl, cyclopropyl, C$_{1-4}$alkylsulphonylC$_{1-4}$alkyl, C$_{1-4}$alkoxycarbonyl, di(C$_{1-4}$alkyl)amino, C$_{1-4}$alkylaminoC$_{1-4}$alkyl, C$_{1-4}$alkanoyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy, carboxamido, trifluoromethyl, or a group —(—O—)$_f$(R$^{b'}$)$^g$ringD (wherein f, g, R$^{b'}$ and D are as defined above); or R$^k$ is other than unsubstituted C$_{2-6}$alkynylene 14") —R$^m$X$^{10}$R$^{m'}$R$^{37}$ (wherein R$^m$, R$^{m'}$ and R$^{37}$ are as defined in (14') above, and X$^{10}$ represents —C(O)—, —NR$^{60}$C(O)O— or —C(O)ONR$^{61}$—, (wherein R$^{60}$ and R$^{61}$ are as defined in (14') above, or where X$^{10}$ is any other group listed in (14') above, and either R$^{37}$ is a pyridone group, a phenyl group or a 5-6-membered aromatic heterocyclic group as (linked via carbon or nitrogen) with 1-3 heteroatoms selected from O, N and S, which pyridone, phenyl or aromatic heterocyclic group which is substituted as described in (6') provided it carries at least one substituent selected from nitro, amino, C$_{1-4}$hydroxyalkoxy, oxo, cyanoC$_{1-4}$alkyl, cyclopropyl, C$_{1-4}$alkylsulphonylC$_{1-4}$alkyl, C$_{1-4}$alkoxycarbonyl, di(C$_{1-4}$alkyl)amino, C$_{1-4}$alkylaminoC$_{1-4}$alkyl, C$_{1-4}$alkanoyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy, carboxamido, trifluoromethyl, or a group —(—O—)$_f$(R$^{b'}$)$_g$ringD (wherein f, g, R$^{b'}$ and D are as defined above), or at least one of R$^m$ or R$^{m'}$ is other than unsubstituted C$_{1-3}$alkylene);

15") R$^{36}$ (where R$^{36}$ is as defined in (5") hereinbefore);

16") —R$^n$X$^{10}$R$^{n'}$R$^{36}$ (wherein R$^n$, R$^{n'}$ and R$^{36}$ are as defined in (16') above and X$^{10}$ represents —C(O)—, —NR$^{60}$C(O)O— or —C(O)ONR$^{61}$—, (wherein R$^{60}$ and R$^{61}$ are as defined in (14') above or X$^{10}$ is any of the other groups set out in (14') above and either R$^{36}$ is as defined in (5") hereinbefore) or at least one of R$^n$ or R$^{n'}$ is other than unsubstituted C$_{1-3}$alkyl;

17") —R$^p$X$^{10}$—R$^{p'}$R$^{37}$ (wherein X$^{10}$ is as defined in (14') above and R$^p$, R$^{p'}$ and R$^{37}$ are as defined in (6') hereinbefore);

18") C$_{2-5}$alkenyl which may be unsubstituted or which may be substituted with one or more groups selected from hydroxy, fluoro, amino, C$_{1-4}$alkylamino, N,N-di(C$_{1-4}$alkyl)amino, aminosulphonyl, N—C$_{1-4}$alkylaminosulphonyl and N,N-di(C$_{1-4}$alkyl)aminosulphonyl;

19") C$_{2-5}$alkynyl which may be unsubstituted or which may be substituted with one or more groups selected from hydroxy, fluoro, amino, C$_{1-4}$alkylamino, N,N-di(C$_{1-4}$alkyl)amino, aminosulphonyl, N—C$_{1-4}$alkylaminosulphonyl and N,N-di(C$_{1-4}$alkyl)aminosulphonyl;

20") —R$^t$X$^{10}$R$^{t'}$R$^{36}$ (wherein X$^{10}$ is as defined in (14') above and R$^{36}$ is as defined in (5') hereinbefore);

21") —R$^u$X$^{10}$R$^{u'}$R$^{36}$ (wherein X$^{10}$ is as defined in (14') above and R$^{36}$ is as defined in (5') hereinbefore); and 22") —R$^v$R$^{69}$(R$^{v'}$)$_q$(X$^{10}$)$_r$R$^{70}$ (wherein X$^{10}$ is as defined in (14') above, q' is 0 or 1, r is 0 or 1, and R$^{69}$ is a C$_{1-3}$alkylene group or a cyclic group selected from cyclopropyl, cyclobutyl, cyclopentylene, cyclohexylene or a 5-6-membered saturated heterocyclic group with 1-2 heteroatoms, selected independently from O, S and N, which C$_{1-3}$alkylene group may bear 1 or 2 substituents selected from oxo, hydroxy, halogeno and C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, i(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(R$^{b'}$)$_g$ringD (wherein f is 0 or 1, g is 0 or 1 and ring D is a cyclic group selected from C$_{3-6}$cycloalkyl, aryl or 5-6-membered saturated or unsaturated heterocyclic group with 1-2 heteroatoms, selected independently from O, S and N, which cyclic group may bear one or more substituents selected from halo and C$_{1-4}$alkyl); and R$^{70}$ is hydrogen, C$_{1-3}$alkyl, or a cyclic group selected from cyclopropyl, cyclobutyl, cyclopentyl, cyclohexyl and a 5-6-membered saturated heterocyclic group with 1-2 heteroatoms, selected independently from O, S and N, which C$_{1-3}$alkyl group may bear 1 or 2 substituents selected from oxo, hydroxy, halogeno, C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$^f$(C$_{1-4}$alkyl)$_g$ringD (wherein f is 0 or 1, g is 0 or 1 and D is a cyclic group selected from C$_{3-6}$cycloalkyl, aryl or 5-6-membered saturated or unsaturated heterocyclic group with 1-2 heteroatoms, selected independently from O, S and N, which cyclic group may bear one or more substituents selected from halo and C$_{1-4}$alkyl);

and wherein R$^a$, R$^b$, R$^{b'}$, R$^c$, R$^{c'}$, R$^e$, R$^i$, R$^m$, R$^{m'}$, R$^n$, R$^{n'}$, R$^{p'}$, R$^{t'}$, R$^{u'}$, R$^v$ and R$^{v'}$ are independently selected from C$_{1-8}$alkylene groups optionally substituted by one or more substituents selected from hydroxy, halogeno, amino, R$^f$, R$^h$, R$^j$, R$^p$ and R$^t$ are independently selected from C$_{2-8}$alkenylene groups optionally substituted by one or more substituents selected from hydroxy, halogeno, amino, and R$^t$ may additionally be a bond; and R$^g$, R$^k$ and R$^u$ are independently selected from by C$_{2-8}$alkynylene groups optionally substituted by one or more substituents selected from hydroxy, halogeno, amino, subject to the proviso set out above.

In many cases, it is preferred that where such groups include a bridging group R$^a$, R$^b$, R$^{b'}$, R$^c$, R$^{c'}$, R$^d$, R$^e$, R$^i$, R$^m$, R$^{m'}$, R$^n$, R$^{n'}$, R$^{p'}$, R$^{t'}$, R$^{u'}$, R$^v$, R$^{v'}$, R$^f$, R$^h$, R$^j$, R$^p$, R$^t$, R$^g$, R$^k$, or R$^u$, said bridging group carries a substitutent as defined above, and in particular a hydroxy substitutent, in order to block metabolism.

In particular, at least one of R$^1$, R$^2$, R$^3$ or R$^4$ is a group of formula X$^1$—R$^{13}$ where R$^{13}$ is a group as defined in (3"), (5"), (19") or (22").

When said group is a group of formula 3", particularly suitable groups R$^{24}$ are cyclopropyl or any C$_{1-6}$ alkyl group substituted by cyclopropyl. Suitably in said groups, X$^3$ is a group NR$^{29}$ where R$^{29}$ is as defined in 3' above and in particular is hydrogen.

When said group is a group of formula 5", particularly suitable examples are compounds where $R^{36}$ is a saturated 7-membered heterocyclic ring or $R^{36}$ is a 5 or 6 membered heterocyclic ring such as morpholine, piperidine or tetrahydropyridyl ring, which carries at least one substituent selected from $C_{1-4}$alkanoyl such as acetyl, or —C(O)NR$^{65}$R$^{66}$—, (wherein R$^{65}$ and R$^{66}$ are as defined in (5') above and in particular are hydrogen.

When said group is a group of formula 19", it is preferably an unsubstituted alkynyl group such as prop-2-ynyl.

When said group is a group of formula 22" above, it is suitably a group in which $R^{69}$ is a 5-6-membered saturated heterocyclic group with 1-2 heteroatoms, such as piperidinyl. Suitably $R^{70}$ is hydrogen or $C_{1-3}$alkyl such as methyl. Suitably also, $X^{10}$ is oxygen. $R^v$ and $R^{v'}$ are suitably the same or different and are $C_{1-5}$ alkylene groups in particular $C_{2-3}$alkylene groups.

In one embodiment, $R^1$, $R^2$, $R^3$ or $R^4$ is a member selected from the group consisting of hydrogen, hydroxy, halogeno, cyano, nitro, trifluoromethyl, $C_{1-3}$alkyl, —NR$^{11}$R$^{12}$ (wherein R$^{11}$ and R$^{12}$, which may be the same or different, each represents hydrogen or $C_{1-3}$alkyl), or a group $R^{13}$—$X^1$—(CH$_2$)$_x$ wherein x is 0 to 3, $X^1$ represents —O—, —CH$_2$—, —OCO—, carbonyl, —S—, —SO—, —SO$_2$—, —NR$^{14}$CO—, —CONR$^{15}$—, —SO$_2$NR$^{16}$—, —NR$^{17}$SO$_2$— or —NR$^{18}$— (wherein R$^{14}$, R$^{15}$, R$^{16}$, R$^{17}$ and R$^{18}$ each independently represents hydrogen, $C_{1-3}$alkyl or $C_{1-3}$alkoxyC$_{2-3}$alkyl) and $R^{13}$ is selected from one of the following sixteen groups:

1) $C_{1-5}$alkyl which may be unsubstituted or which may be substituted with one or more groups selected from hydroxy, fluoro and amino;
2) $C_{1-5}$alkylX$^2$COR$^{19}$ (wherein X$^2$ represents —O— or —NR$^{20}$— (wherein R$^{20}$ represents hydrogen, $C_{1-3}$alkyl or $C_{1-3}$alkoxyC$_{2-3}$alkyl) and $R^{19}$ represents —NR$^{21}$R$^{22}$— or —OR$^{23}$— (wherein R$^{21}$, R$^{22}$ and R$^{23}$ which may be the same or different each represents hydrogen, $C_{1-3}$alkyl or $C_{1-3}$alkoxyC$_{2-3}$alkyl));
3) $C_{1-5}$alkylX$^3$R$^{24}$ (wherein X$^3$ represents —O—, —S—, —SO—, —SO$_2$—, —OCO—, —NR$^{25}$CO—, CONR$^{26}$—, —SO$_2$NR$^{27}$—, —NR$^{28}$SO$_2$— or —NR$^{29}$— (wherein R$^{25}$, R$^{26}$, R$^{27}$, R$^{28}$ and R$^{29}$ each independently represents hydrogen, $C_{1-3}$alkyl or $C_{1-3}$alkoxyC$_{2-3}$alkyl) and $R^{24}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);
4) $C_{1-5}$alkylX$^4$C$_{1-5}$alkylX$^5$R$^{30}$ (wherein X$^4$ and X$^5$ which may be the same or different are each —O—, —S—, —SO—, —SO$_2$—, —NR$^{31}$CO—, —CONR$^{32}$—, —SO$_2$NR$^{33}$—, —NR$^{34}$SO$_2$— or —NR$^{35}$— (wherein R$^{31}$, R$^{32}$, R$^{33}$, R$^{34}$ and R$^{35}$ each independently represents hydrogen, $C_{1-3}$alkyl or $C_{1-3}$alkoxyC$_{2-3}$alkyl) and $R^{30}$ represents hydrogen or $C_{1-3}$alkyl);
5) $C_{1-5}$alkylR$^{36}$ (wherein R$^{36}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);
6) (CH$_2$)$_q$X$^6$R$^{37}$ (wherein q is an integer from 0 to 5, X$^6$ represents a direct bond, —O—, —S—, —SO—, —SO$_2$—, —NR$^{38}$CO—, —CONR$^{39}$—, —SO$_2$NR$^{40}$—, —NR$^{41}$SO$_2$— or —NR$^{42}$— (wherein R$^{38}$, R$^{39}$, R$^{40}$, R$^{41}$ and R$^{42}$ each independently represents hydrogen, $C_{1-3}$alkyl or $C_{1-3}$alkoxyC$_{2-3}$alkyl) and $R^{37}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$hydroxyalkoxy, $C_{1-4}$aminoalkyl, $C_{1-4}$alkylamino, carboxy, cyano, —CONR$^{43}$R$^{44}$ and —NR$^{45}$COR$^{46}$ (wherein R$^{43}$, R$^{44}$, R$^{45}$ and R$^{46}$, which may be the same or different, each represents hydrogen, $C_{1-4}$alkyl or $C_{1-3}$alkoxyC$_{2-3}$alkyl));
7) $C_{2-6}$alkenylR$^{36}$ (wherein R$^{36}$ is as defined in (5) above);
8) $C_{2-6}$alkynylR$^{36}$ (wherein R$^{36}$ is as defined in (5) above);
9) $X^7$R$^{47}$ (wherein X$^7$ is —SO$_2$—, —O— or —CONR$^{48}$R$^{49}$— (wherein R$^{48}$ and R$^{49}$, which may be the same or different, each represents hydrogen, $C_{1-3}$alkyl or $C_{1-3}$alkoxyC$_{2-3}$alkyl) and $R^{47}$ represents $C_{1-5}$alkyl which may be unsubstituted or which may be substituted with one or more groups selected from hydroxy, fluoro and amino) with the provisos that when X$^7$ is —SO$_2$—, X$^1$ is —O—, when X$^7$ is —O—, X$^1$ is carbonyl, when X$^7$ is —CONR$^{48}$R$^{49}$—, X$^1$ is —O— or NR$^{18}$ (wherein R$^{48}$, R$^{49}$ and R$^{18}$ are as defined above);
10) $C_{2-6}$alkenylR$^{37}$ (wherein R$^{37}$ is as defined in (6) above);
11) $C_{2-6}$alkynylR$^{37}$ (wherein R$^{37}$ is as defined in (6) above);
12) $C_{2-6}$alkenylR$^{37}$ (wherein X$^8$ represents —O—, —S—, —SO—, —SO$_2$—, —NR$^{50}$CO—, —CONR$^{51}$—, —SO$_2$NR$^{52}$—, —NR$^{53}$SO$_2$— or —NR$^{54}$— (wherein R$^{50}$, R$^{51}$, R$^{52}$, R$^{53}$ and R$^{54}$ each independently represents hydrogen, $C_{1-3}$alkyl or $C_{1-3}$alkoxyC$_{2-3}$alkyl) and $R^{37}$ is as defined in (6) above);
13) $C_{2-6}$alkynylX$^9$R$^{37}$ (wherein X$^9$ represents —O—, —S—, —SO—, —SO$_2$—, —NR$^{55}$CO—, —CONR$^{56}$—, —SO$_2$NR$^{57}$—, —NR$^{58}$SO$_2$— or —NR$^{59}$— (wherein R$^{55}$, R$^{56}$, R$^{57}$, R$^{58}$ and R$^{59}$ each independently represents hydrogen, $C_{1-3}$alkyl or $C_{1-3}$alkoxyC$_{2-3}$alkyl) and $R^{37}$ is as defined in (6) above);
14) $C_{1-3}$alkylX$^{10}$C$_{1-3}$alkylR$^{37}$ (wherein X$^{10}$ represents —O—, —S—, —SO—, —SO$_2$—, —NR$^{60}$CO—, —CONR$^{61}$—, SO$_2$NR$^{62}$—, —NR$^{63}$SO$_2$— or —NR$^{64}$— (wherein R$^{60}$, R$^{61}$, R$^{62}$, R$^{63}$ and R$^{64}$ each independently represents hydrogen, $C_{1-3}$alkyl or $C_{1-3}$alkoxyC$_{2-3}$alkyl) and $R^{37}$ is as defined in (6) above);
15) $R^{36}$ (wherein $R^{36}$ is as defined in (5) above); and
16) $C_{1-3}$alkylX$^{10}$C$_{1-3}$alkylR$^{36}$ (wherein X$^{10}$ and R$^{36}$ are as defined in (5) above).

Suitably, $R^1$ and $R^4$ are hydrogen.

Suitably $R^2$ and $R^3$ are other than hydrogen and in particular are a group of formula —X$^1$—R$^{13}$ as defined above.

Examples of preferred groups for $R^2$ include $C_{1-6}$ alkoxy such as methoxy. The group $R^3$ is suitably selected from hydrogen or $C_{1-6}$alkoxy. In other embodiments however, $R^3$ is selected from (i) a group of formula —X$^1$—R$^x$—(OH)$_{p'}$ where X$^1$ is as defined above, R$^x$ is an alkylene, alkenylene or alkynylene chain, optionally interposed with a heteroatom or a heterocyclic ring and p' is 1 or 2;

(ii) a group of formula R$^{13}$—X$^{20}$—(CH$_2$)$_x$ where R$^{13}$ and x are as defined above and X$^{20}$ is a group —NR$^{14}$C(O)—, —C(O)NR$^{15}$— or —NR$^{18}$— where R$^{14}$, R$^{15}$ and R$^{18}$ are as defined above;

(iii) a group of formula —X$^1$—R$^y$—NR$^{zz}$—R$^{y'}$—S—R$^{y''}$ where X$^1$ is as defined above, R$^y$, R$^{y'}$ and R$^{y''}$ are independently selected from alkyl, alkenyl or alkynyl chains, and $R^{zz}$ is hydrogen or alkyl, or $R^{zz}$ and $R^{y''}$ are joined together to form an optionally substituted nitrogen and sulphur containing ring; or (iv) a group of formula —$X^1$—$R^{x'}$-($C_{4-6}$cycloalkyl) where $X^1$ is as defined above and $R^{x'}$ is an alkylene, alkenylene or alkynylene chain, optionally interposed with a heteroatom.

When $R^3$ is a group of formula —$X^1$—$R^x$—$(OH)_{p'}$, suitable examples of $X^1$ are —O—, —$NR^{14}C(O)$—, —$C(O)NR^{15}$— or —$NR^{18}$— where $R^{14}$, $R^{15}$ and $R^{18}$ are as defined above. In particular $X^1$ is —O—. Particular examples of $R^x$ are $C_{2-6}$alkylene chains which is interposed by at least one heteroatom such as nitrogen, or a heterocyclic ring, in particular, a saturated 5-6 membered heterocyclic ring. The ring suitably contains at least from one to three and preferably one heteroatom which is suitably nitrogen. In particular, the heterocyclic ring is a saturated heterocyclic ring. The hydroxy groups may be attached to the alkylene portion of the group $R^x$ or where present, the heterocyclic ring. In particular, these groups are groups of sub-formula (i)

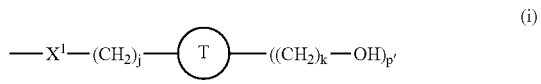

(i)

where $X^1$ and p' is as defined above, T is a 5 or 6 membered nitrogen containing ring, j is 2, 3, 4, or 5, and k is 0, 1, 2 or 3

Where the alkylene chain $R^x$ is interposed with a nitrogen atom, it is suitably in the form or a group —$NR^{85}$— where $R^{85}$ is hydrogen or alkyl, in particular $C_{1-3}$alkyl.

Where $R^3$ is a group of formula $R^{13}$—$X^{20}$—$(CH_2)_x$, x is suitably 0. Preferred groups $R^{13}$ are those set out below in respect of $R^1$, $R^2$ and $R^4$. Suitably $R^{14}$, $R^{15}$ and $R^{18}$ are hydrogen or $C_{1-3}$ alkyl and preferably hydrogen.

Particular examples of groups of formula —$X^1$—$R^y$—$NR^{zz}$—$R^{y'}$—S—$R^{y''}$ for $R^3$ are groups where $X^1$ is —O—, —$NR^{14}C(O)$—, —$C(O)NR^{15}$— or —$NR^{18}$— where $R^{14}$, $R^{15}$ and $R^{18}$ are as defined above. In particular $X^1$ is —O—. Suitably $R^y$ is a $C_{2-6}$alkylene group. Suitably $R^{y'}$ is a $C_{2-3}$alkylene group. Particular examples of $R^{y''}$ are $C_{1-4}$alkyl. Suitably $R^z$ is hydrogen or $C_{1-3}$alkyl and in particular is hydrogen.

In one embodiment however, the group —$NR^{zz}$—$R^{y'}$—S—$R^{y''}$ is a thiomorpholine ring.

Where $R^3$ is a group of formula —$X^1$—$R^{x'}$—($C_{4-6}$cycloalkyl), $X^1$ is suitably —O—, $NR^{14}C(O)$—, —$C(O)NR^{15}$— or —$NR^{18}$— where $R^{14}$, $R^{15}$ and $R^{18}$ are as defined above. In particular $X^1$ is —O—. Particular examples of $R^{x'}$ are $C_{2-5}$alkylene groups which suitably include at least one heterotom in particular a group —$NR^{85}$— where $R^{85}$ is as defined above. Suitably the $C_{4-6}$cycloalkyl group is cyclopentyl.

A further preferred group for $R^2$ or $R^3$ is 3-morpholinopropyloxy.

Suitably at least one of least one of $R^2$ or $R^3$ is a group —$X^1$—$R^3$ where $X^1$ is as defined above and $R^{13}$ is any of the groups defined in any one of the twenty two group (1")-(22") as set out above. Preferably $R^3$ is said group. In this case, the other group $R^2$ and $R^3$ may be any of the groups defined above for $R^1$, $R^2$, $R^3$ or $R^4$. Preferably however said other group is a small group such as hydrogen or $C_{1-4}$ alkoxy such as methoxy.

In one embodiment $R^1$ and $R^4$ are each hydrogen and $R^2$ and $R^3$ are independently selected from $C_{1-4}$ alkoxy or a group of the formula —$(CH_2)_x$—$X^1$—$R^{13}$ wherein x is 0 and $X^1$ is selected from —O—, —$NR^{18}$— or —$NR^{15}C(O)$— (wherein $R^{15}$ and $R^{18}$ each independently represents hydrogen, $C_{1-3}$alkyl or $C_{1-3}$alkoxy$C_{2-3}$alkyl) and $R^{13}$ is selected from one of the following groups:

1) $C_{1-5}$alkyl which may be unsubstituted or which may be substituted with one or more groups selected from hydroxy, oxiranyl, fluoro, chloro, bromo and amino;
2) $R^bX^3R^{24}$ wherein $R^b$, $X^3$ and $R^{24}$ are as defined above;
3) $R^dR^{36}$ wherein $R^d$ and $R^{36}$ are as defined above; and
4) —$R''X^{10}R''^{'}R^{36}$ wherein $R''$, $X^{10}$, $R''^{'}$ and $R^{36}$ are as defined above;

Particularly, $R^1$ and $R^4$ are each hydrogen; $R^2$ is $C_{1-4}$alkoxy and $R^3$ is selected from a group of the formula —$(CH_2)_x$—$X^1$—$R^{13}$ wherein x is 0 and $X^1$ is selected from —O—, —$NR^{18}$— or —$NR^{15}C(O)$— (wherein $R^{15}$ and $R^{18}$ each independently represents hydrogen, $C_{1-3}$alkyl or $C_{1-3}$alkoxy$C_{2-3}$alkyl) and $R^{13}$ is selected from one of the following groups:

1) $C_{1-5}$alkyl substituted with cyano;
2) $R^bX^3R^{24}$ wherein $R^{24}$ is cyclopropyl, cyclobutyl, cyclopentyl or cyclohexyl or a 5-6 membered saturated heterocyclic group, $X^3$ is —$NR^{29}$— (wherein $R^{29}$ is as defined above) and $R^b$ is as defined above;
3) —$R^dR^{36}$ wherein $R^{36}$ is a saturated heterocyclic group with 1 or 2 heteroatoms independently selected from O, S and N which group may bear 1 or 2 substituents as defined above and $R^d$ is as defined above; and
4) —$R''X^{10}R''^{'}R^{36}$ wherein $R^{36}$ is a saturated heterocyclic group with 1 or 2 heteroatoms independently selected from O, S and N which group may bear 1 or 2 substituents as defined above, $X^{10}$ is —CO— and $R''$, and $R''^{'}$ are as defined above; In another embodiment, $R^1$, and $R^4$ are both hydrogen, $R^2$ is methoxy and $R^3$ is independently selected from pyrrolidin-1-ylpropoxy, pyrrolidin-1-ylpropylamino, morpholinopropoxy, piperidinopropoxy, thiomorpholinopropoxy, 1-oxo-thiomorpholinopropoxy, 1,1-dioxo-thiomorpholinopropoxy, cyclopropylaminopropoxy, azetidin-1-ylacetylmethoxy, pyrrolidin-1-ylacetylmethoxy, 4-methylmorpholin-2-ylmethoxy, 2,6-dimethylmorpholinopropoxy, 3,5-dimethylmorpholinopropoxy, 2,6-dimethylpiperidin-1-ylpropoxy, 4-methoxyethylpiperazin-1-ylpropoxy, 4-acetylpiperazin-1-ylpropoxy, 3-methylsulphonylpyrrolidin-1-ylpropoxy, 4-ethylsulphonylpiperazin-1-ylpropoxy, imidazol-1-ylethoxy, 1,1-dioxo-tetrahydrothiophen3-yl(N-methylamino)propoxy, 3-hydroxypiperidin-1-ylpropoxy, N,N-di-(hydroxyethyl)aminopropoxyand hydroxyethoxyethoxy.

In yet a further embodiment, both $R^2$ and $R^3$ are $C_{1-6}$alkoxy and are preferably methoxy.

Preferably, $R^5$ is cyano.

Suitable groups Y include oxygen or —NH— and most preferably are —NH—.

In particular, in the compound of formula (I), (IA) or (IB), n is 0.

Suitably $R^8$ is a divalent phenyl. Preferably X is arranged on $R^8$ is in the para position.

Suitably X is oxygen or —NH— and most preferably oxygen.

Suitably m is 0.

Examples of optional substituents for heterocyclic groups $R^9$ or aryl, carbocyclic or heterocyclic groups $R^{10}$ as well as substituents for alkyl group $R^{110'}$ in $R^8$ include one or more groups selected from hydroxy; halo; nitro; cyano; carboxy; $C_{1-6}$ alkoxy; $C_{1-6}$alkyl; $C_{2-6}$alkenyl; $C_{2-6}$alkynyl; $C_{2-6}$alkenyloxy; $C_{2-6}$alkynyloxy; $C_{3-6}$cylcoalkyl; amino; mono- or di-$C_{1-6}$alkyl amino; heterocyclyl optionally substituted with $C_{1-6}$alkyl or oxo; $C(O)R^{aa}$; $C(O)OR^{aa}$; $S(O)_dR^{aa}$; $NR^{aa}C(O)R^{bb}$; $C(O)NR^{aa}S(O)_dR^{bb}$; $C(O)NR^{aa}R^{bb}$; $NR^{aa}C(O)NR^{bb}R^{cc}$; $NR^{aa}S(O)_dR^{bb}$ or $N(S(O)_dR^{bb})S(O)_dR^{cc}$ where d is 0, 1 or 2 and $R^{aa}$, $R^{bb}$ and $R^{cc}$ are independently selected from hydrogen, $C_{1-6}$alkyl, aryl, $C_{3-6}$cycloalkyl or heterocyclyl, and wherein any alkyl, alkenyl or alkynyl group or moiety contained within the substituent on $R^{10}$ may themselves be optionally substituted with one or more groups selected from hydroxy; cyano; nitro; halo; carboxy; carboalkoxy of 2-7 carbon atoms; $C_{3-6}$cycloalkyl; heterocyclyl optionally substituted with $C_{1-6}$alkyl or oxo; $C(O)R^{dd}$; $C(O)OR^{dd}NR^{dd}R^{ee}$; $S(O)_eR^{dd}$; $NR^{dd}C(O)R^{ee}$; $C(O)NR^{dd}R^{ee}$; $NR^{dd}C(O)NR^{ee}R^{ff}$; or $NR^{dd}S(O)_eR^{ee}$ where e is 0, or 2 and $R^{dd}$, $R^{ee}$ and $R^{ff}$ are independently selected from hydrogen or $C_{1-6}$alkyl optionally substituted with one or more groups selected from hydroxy, cyano; nitro; halo; carboxy, carboalkoxy of 2-7 carbon atoms; $C_{3-6}$ cycloalkyl; heterocyclyl optionally substituted with $C_{1-6}$alkyl or oxo; $C(O)R^{gg}$; $C(O)OR^{gg}$; $NR^{gg}R^{hh}$; $S(O)_eR^{gg}$; $NR^{hh}C(O)R^{gg}$; $C(O)NR^{gg}R^{hh}$; $NR^{gg}C(O)NR^{hh}R^{ii}$; or $NR^{gg}S(O)_eR^{hh}$ where e is as defined above and $R^{gg}$, $R^{hh}$ and $R^{ii}$ are independently selected from hydrogen, $C_{1-6}$alkyl or heterocyclyl.

In some embodiments, the level of substitution on the group $R^{10}$ is complex.

Thus, for example, a substituent may comprise a substituted alkyl chain which is optionally interposed with heteroatoms such as groups of sub-formula (ia)

$$-X^a-R^{70}-(X^b-R^{71})_Q-(X^c)_R-R^{72} \quad \text{(ia)}$$

where $X^a$, $X^b$ and $X^c$ are independently selected from any of the groups listed above for $X^1$, $R^{70}$ and $R^{71}$ are independently selected from $C_{1-6}$alkylene, $C_{2-6}$alkenylene or $C_{2-6}$alkynylene groups any of which may be optionally substituted with hydroxy; cyano; nitro; halo; carboxy; carboalkoxy of 2-7 carbon atoms or $C_{3-6}$cycloalkyl;

$R^{72}$ is hydrogen or an C-alkyl, $C_{2-6}$ alkenyl or $C_{2-6}$alkynyl group any of which may be optionally substituted with hydroxy, cyano, nitro, halo, carboxy, $C_{3-6}$cycloalkyl and in particular cyclopropyl, or an optionally substituted heterocyclic group, in particular a group as defined above for $R^{36}$, and Q and R are independently 0 or 1.

In some embodiments, $R^{10}$ is a heterocyclic ring containing one or 2 oxygen atoms.

Examples of heterocyclic rings $R^{10}$ include 3-7 membered rings, up to two of which may be oxygen atoms. Such groups include:

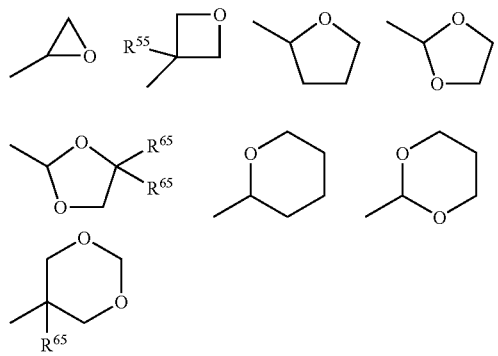

where each $R^{65}$ is independently selected from hydrogen or $C_{1-6}$alkyl and especially methyl.

Other examples of heterocyclic groups $R^{10}$ include pyridyl, thiazolyl, pyrazinyl, pyrimidinyl, oxadiazole.

Particular examples of groups $R^{10}$ include a divalent phenyl, pyridyl or $C_{1-3}$cycloalkyl. Most preferably however, $R^{10}$ is an optionally substituted phenylene. $R^9$ is preferably a group selected from $C_{1-2}$ alkylene, or a divalent $C_{3-4}$ cycloalkyl, pyridyl, pyrrolidinyl or phenyl. Suitable further substituents for $R^9$ and $R^{10}$ include those listed above for pyridyl, pyrimidinyl and phenyl groups $R^8$.

In a preferred embodiment $R^9$ and $R^{10}$ are both phenylene; Y is —NH and X is oxygen; and n, m and p are all 0. A particularly preferred substituent on $R^{10}$ is fluoro.

Preferably $R^6$ is hydrogen,

Suitable examples of variables within sub-formula (i) defined above are as follows:

$X^{12}$ is suitably —O—;

$R^{75}$ is suitably $C_{1-6}$alkylene and preferably the group —$C(R^AR^B)$ where $R^A$ and $R^B$ are each independently selected from $C_{1-3}$ alkyl, $C_{2-3}$ alkenyl, $C_{2-3}$ alkynyl and halo, are most preferably both either $C_1$ alkyl or fluoro $R^{76}$ and $R^{77}$ are suitably the same or different and are preferably independently selected from $C_{1-6}$alkylene and in particular methylene groups and a direct bond. Most preferably $R^{77}$ is a direct bond.

$X^{13}$ is preferably the group —$CONR^{79}$— or —$NR^{78}C(O)$—, most preferably the group —$CONR^{79}$—, where $R^{78}$ and $R^{79}$ are selected from hydrogen or $C_{1-3}$ alkyl and are more preferably hydrogen;

$X^{14}$ is suitably —C(O)—, —$CONR^{79}$—, where $R^{78}$ and $R^{79}$ are selected from hydrogen or $C_{1-3}$ alkyl and are preferably hydrogen, or a direct bond;

s, s' q and p are all preferably 0.

Where Z is a group of sub-formula (i), a particularly preferred group is selected from

—O—$C(CH_3)_2$—$CONR^{79}$—;

—O—$C(F)_2$—;

—O—$C(CH_3)_2$—$CONR^{79}$—$CH_2$—$CONR^{79}$—;

—O—$C(CH_3)_2$—$CONR^{79}$—$CH_2$—$CONR^{79}$—$(CH_2)_2$—$NR^{82}$—;

—O—$C(F)_2$—$CONR^{79}$—;

—O—$C(F)_2$—$CONR^{79}$—$CH_2$—$CONR^{79}$—;

—O—$C(CH_3)_2$—$CONR^{79}$—$CH_2$—$NR^{82}$—;

—O—$C(CH_3)_2$—$CONR^{79}$—$(CH_2)_2$—$SO_2$—;

—O—$C(CH_3)_2$—$CONR^{79}$—$(CH_2)_2$—S—; and

—O—$C(CH_3)_2$—$CONR^{79}$—$(CH_2)_2$—O— where $R^{79}$, $R^{82}$ are preferably as hereinbefore defined and preferably are methyl or hydrogen, most preferably hydrogen. Alternatively Z is preferably a direct bond.

Examples of suitable heterocyclic groups $R^9$ are 5- or 6-membered aromatic or non-aromatic rings which contain up to 4 and preferably up to 3 heteroatoms. A particular example of a non-aromatic group $R^9$ is piperazino or morpholine or piperidine linked via carbon or nitrogen but preferably by nitrogen atoms whilst an example of an aromatic group is oxadiazole.

Where Z is a group of sub-formula (i), $R^9$ may be substituted by a simple $C_{1-6}$alkyl group such as methyl. However, where Z is a direct bond, more complex substituents are required to be present on the ring $R^9$. In such instances, at least one group $X^{17}$, $X^{17}$ or $X^{18}$, and preferably at least $X^{18}$, in the group of sub-formula (ii) is other than a direct bond. Preferably, at least one such group, and most preferably $X^{18}$ is —S—, —S(O)— or —$S(O)_2$—.

Thus a sub-group of compounds of formula (I) are compounds of formula (IC)

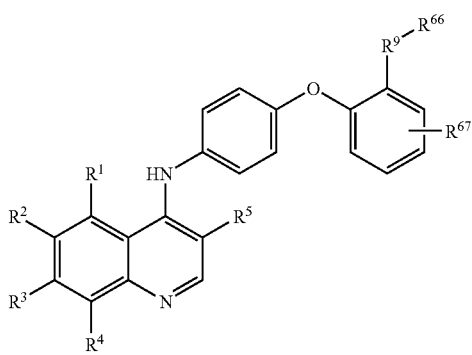

(IC)

where $R^1$, $R^2$, $R^3$, $R^4$, $R^5$ and $R^9$ are as defined above, $R^{66}$ is a group of sub-formula (ii) as defined above where at least $X^{18}$ is other than a direct bond;

and $R^{67}$ is selected from hydrogen, halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, and benzoylamino.

Suitably $R^{66}$ is a $C_{1-6}$ alkylthio$C_{1-6}$alkyl group —CH$_2$SCH$_3$ or a sulphoxide derivative thereof.

Preferably $R^{67}$ is hydrogen.

Alternatively, in another embodiment, the compounds of formula (I) are compounds of formula (ID)

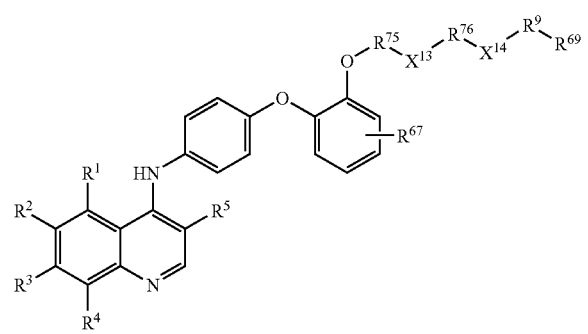

(ID)

where $R^1$, $R^2$, $R^3$, $R^4$, $R^5$ and $R^9$ are as defined above in relation to formula (I), $R^{67}$ is as defined above in relation to formula (IC), $R^{75}$, $R^{76}$, $X^{13}$ and $X^{14}$ are as defined above in relation to sub-formula (i), and $R^{69}$ is a group of sub-formula (ii) as defined above but in particular is $C_{1-6}$alkyl.

Particularly preferred compounds according to the invention are compounds of formula (IE)

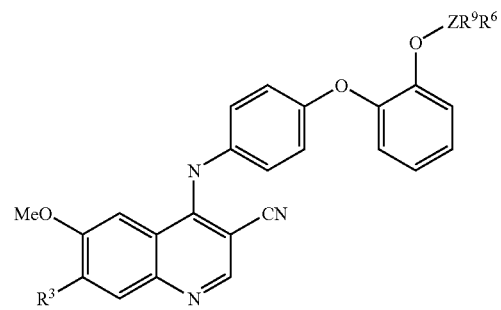

(IE)

or a pharmaceutically acceptable salt, prodrug or solvate thereof; and wherein $R^3$, Z, $R^9$ and $R^6$ are selected from the following groups:

i) $R^3$ is —OCH$_3$, Z is the group —O—C(CH$_3$)$_2$—CONH—CH$_2$—CONH—, the group $R^9$—$R^6$ is —C$_2$H$_5$;

ii) $R^3$ is —OCH$_3$, Z is the group —O—C(CH$_3$)$_2$—CONH—CH$_2$—CONH—, the group $R^9$—$R^6$ is cyclobutyl;

iii) $R^3$ is H, Z is the group —O—C(CH$_3$)$_2$—CONH—OH$_2$—CONH—, the group $R^9$—$R^6$ is CH$_3$;

iv) $R^3$ is H, Z is the group —O—C(CH$_3$)$_2$—CONH—CH$_2$—CONH—, the group $R^9$—$R^6$ is CH$_3$;

v) $R^3$ is —OCH$_3$, Z is the group —O—C(CH$_3$)$_2$—CONH—CH$_2$—CON(CH$_3$)—, the group $R^9$—$R^6$ is —CH$_3$;

vi) $R^3$ is —OCH$_3$, Z is the group —O—C(CH$_3$)$_2$—CONH—CH$_2$—CONH—, the group $R^9$—$R^6$ is cyclopropyl;

vii) $R^3$ is —OCH$_3$, Z is the group —O—C(CH$_3$)$_2$—CONH—CH$_2$—CONH—CH$_2$, the group $R^9$—$R^6$ is cyclopropyl;

viii) $R^3$ is —OCH$_3$, Z is the group —O—C(CH$_3$)$_2$—CONH—CH$_2$—CONH—CH$_2$, the group $R^9$—$R^6$ is CH$_3$;

ix) $R^3$ is —NHCH$_3$, Z is the group —O—C(CH$_3$)$_2$—CONH— the group $R^9$—$R^6$ is CH$_3$;

x) $R^3$ is —OCH$_3$, Z is the group —O—C(CH$_3$)$_2$—(CH$_2$)$_2$—, the group $R^9$—$R^6$ is pyridine;

xi) $R^3$ is —NHCH$_3$, Z is the group —O—C(CH$_3$)$_2$—CONH—, the group $R^9$—$R^6$ is cyclopropyl; and xii) $R^3$ is —OCH$_3$, Z is the group —O—C(CH$_3$)$_2$—CONH—CH$_2$—CONH—(CH$_2$)$_2$—N(CH$_3$)—, the group $R^9$—$R^6$ is —CH$_3$; and xiii) $R^3$ is 3-(1-morpholino)propoxy, Z is the group —O—C(CH$_3$)—CONH—, the group $R^9$—$R^6$ is —CH$_2$)$_2$OH A further group of compounds according to the invention

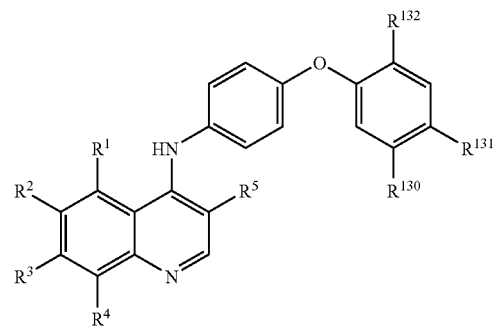

(IF)

wherein are compounds of formula (IF)

R[130] is a group of formula (i) as hereinbefore defined and preferably is selected from —NR[78]C(O)—R[9]—R[6], —NR[82]—R[9]—R[6]; and $C_{1-4}$ alkoxyl; hydrogen or halo, particularly fluoro, where R[78], R[82], R[9] and R[6] are as hereinbefore defined;

R[131] is a hydrogen or halo, particularly fluoro; and

R[132] is a $C_{1-4}$ alkoxy

Particular examples of compounds according to the invention are listed in Tables 1 to 9 below, where * denotes the point of attachment.

TABLE 1

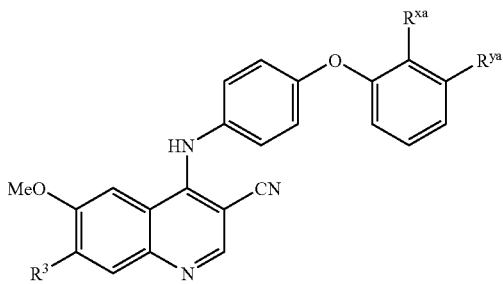

| Compd No | R[3] | R[xa] | R[ya] |
|---|---|---|---|
| 1 | OCH₃ | 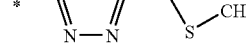 | H |
| 2 | OCH₃ | 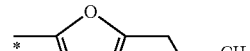 | H |
| 3 | OCH₃ | 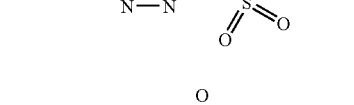 | H |
| 4 | OCH₃ | OCH₂CH(OH)CH₂(N-morpholine) | H |
| 5 | OCH₃ | OCH₂CH(OH)CH₂(N-piperidine) | H |
| 6 | OCH₃ | OC(CH₃)₂C(O)NHCH₃ | H |
| 7 | 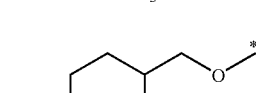 | OC(CH₃)₂C(O)NHCH₃ | H |
| 8 | 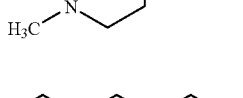 | OC(CH₃)₂C(O)NHCH₃ | H |
| 9 | OCH₃ | OCH₂C(O)N(CH₃)CH₂C(O)—OCH₃ | H |
| 10 | 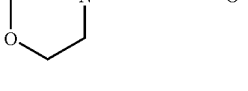 | H | C(O)NH-cyclopropyl |

TABLE 2
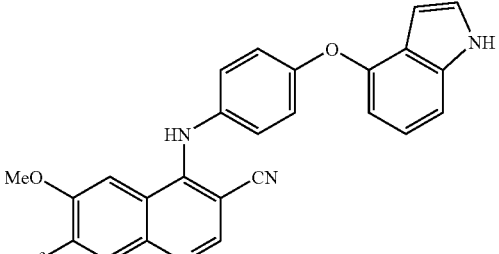
| Compd No | R³ |
|---|---|
| 11 | OCH₃ |
TABLE 3
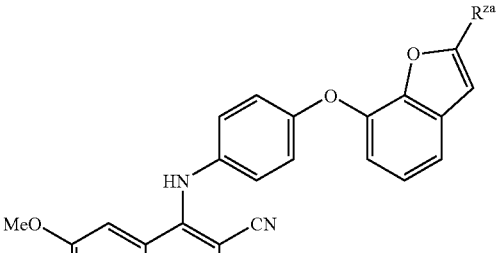
| Compd No | R³ | R^{za} |
|---|---|---|
| 12 | OCH₃ | C(O)-NCH₃ |
TABLE 3-continued
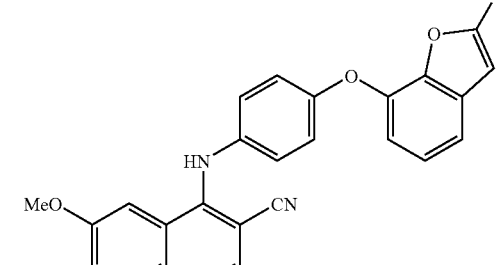
| Compd No | R³ | R^{za} |
|---|---|---|
| 13 | OCH₃ | C(O)—N-cyclopropyl |
TABLE 4
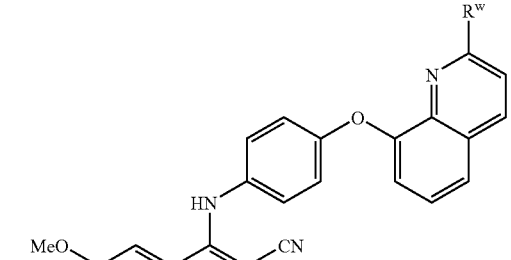
| Compd No. | R³ | R^{w} |
|---|---|---|
| 14 | OCH₃ | C(O)NC(CH₃)₂ |
| 15 | OCH₃ | C(O)—N-cyclopropyl |
TABLE 5
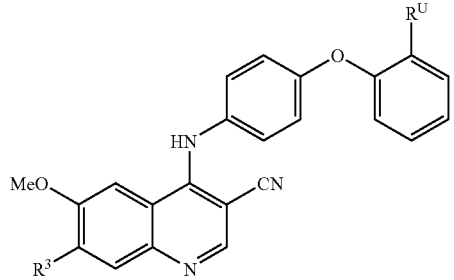
| Compd No | R³ | R^{U} |
|---|---|---|
| 15A | OCH₃ | —OC(CH₃)₂C(O)NH-cyclopropyl |
| 16 | 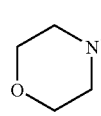 | —OC(CH₃)₂C(O)NH-cyclopropyl |

TABLE 5-continued

| Compd No | R³ | R^U |
|---|---|---|
| 17 | OCH₃ | —OC(CH₃)₂C(O)NH(CH₂)₃—N(morpholine) |
| 18 | OCH₃ | —OC(CH₃)₂C(O)NH(CH₂)₂—N(2-oxoimidazolidin-1-yl) |
| 19 | OCH₃ | —OC(CH₃)₂C(O)NH(CH₂)₂—N(morpholine) |
| 20 | OCH₃ | —OC(CH₃)₂C(O)NH(CH₂)₃—N(imidazol-1-yl) |
| 21 | OCH₃ | —OC(CH₃)₂C(O)NH(CH₂)₃—N(pyrrolidin-1-yl) |
| 22 | OCH₃ | —OC(CH₃)₂C(O)NHCH₂C(O)NH-cyclopropyl |
| 23 | OCH₃ | —OC(CH₃)₂C(O)NHCH₂C(O)N—CH₂-cyclopropyl |
| 24 | OCH₃ | —OC(CH₃)₂C(O)NHCH₂C(O)NHCH₃ |
| 25 | OCH₃ | —OC(CH₃)₂C(O)NH(CH₂)₂N(CH₃)₂ |
| 26 | NCH₃ | —OC(CH₃)₂C(O)NHCH₃ |
| 27 | OCH₃ | —OC(CH₃)₂C(O)NH(CH₂)₂—(pyridin-2-yl) |
| 28 | OCH₃ | —OCH₂C(O)N(CH₃)(CH₂)₂—(pyridin-2-yl) |
| 29 | OCH₃ | —OC(CH₃)₂C(O)NH(CH₂)₂—(pyridin-4-yl) |
| 30 | OCH₃ | —OC(F)₂C(O)NHCH₃ |
| 31 | OCH₃ | —OC(F)₂C(O)NH-cyclopropyl |
| 32 | NCH₃ | —OC(CH₃)₂C(O)NHCH₂C(O)NHCH₃ |
| 33 | NCH₃ | —OC(CH₃)₂C(O)NHCH₂C(O)NH-cyclopropyl |
| 34 | OCH₃ | —OC(CH₃)₂C(O)NH(CH₂)₂—N(pyrrolidin-1-yl) |
| 35 | OCH₃ | —OC(CH₃)₂C(O)—NHCH₂C(O)NH(CH₂)₂N(CH₃)₂ |

TABLE 5-continued

| Compd No | R³ | R^U |
|---|---|---|
| 36 | OCH₃ | —OC(CH₃)₂C(O)NH(CH₂)₂NHC₂H₅ |
| 37 | OCH₃ | —OC(CH₃)₂C(O)NHCH₂C(O)NHC₂H₅ |
| 38 | OCH₃ | —OC(CH₃)₂C(O)NHCH₂C(O)NH-cyclobutyl |
| 39 | H | OC(CH₃)₂C(O)NHCH₃ |
| 40 | H | —OC(CH₃)₂C(O)NHCH₂C(O)NHCH₃ |
| 41 | OCH₃ | —OC(F)₂C(O)NHCH₂C(O)NHCH₃ |
| 42 | OCH₃ | —OC(F)₂C(O)NHCH₂C(O)NH-cyclopropyl |
| 43 | OCH₃ | —OC(CH₃)₂C(O)NHCH₂C(O)NHC(CH₃)₂ |
| 44 | OCH₃ | —OC(CH₃)₂C(O)NH(CH₂)₂SO₂CH₃ |
| 45 | OCH₃ | —OC(CH₃)₂C(O)NH(CH₂)₂SCH₃ |
| 46 | OCH₃ |  |
| 47 | NCH₃ | —OC(CH₃)₂C(O)NHCH₂C(O)NHC₂H₅ |
| 48 | NCH₃ | —OC(CH₃)₂C(O)NH-cyclopropyl |
| 49 | NCH₃ |  |
| 50 | OCH₃ | —OC(CH₃)₂C(O)NH(CH₂)₂OH |
| 51 |  | —OC(CH₃)₂C(O)NH(CH₂)₂OH |
| 52 | OCH₃ | —OC(CH₃)₂C(O)NH₂ |
| 52A | OCH₃ | 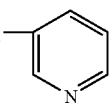 |
| 52B | OCH₃ | 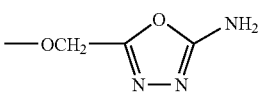 |
| 52C | OCH₃ | —OCH₂  |
| 52D | NHC(O)CH₃ | OCH(CH₃)₂C(O)NHCH₂C(O)NHCH₃ |

TABLE 6

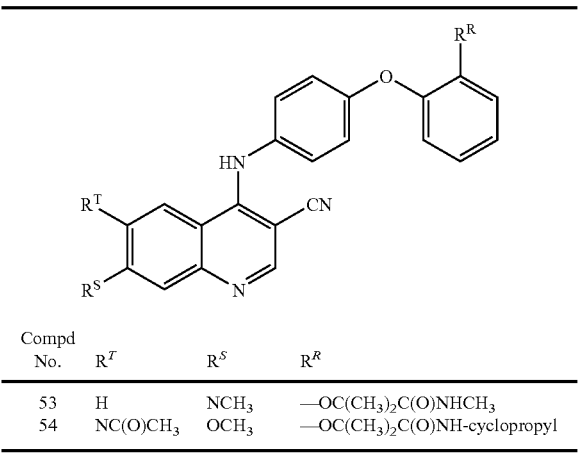

| Compd No. | $R^T$ | $R^S$ | $R^R$ |
|---|---|---|---|
| 53 | H | NCH$_3$ | —OC(CH$_3$)$_2$C(O)NHCH$_3$ |
| 54 | NC(O)CH$_3$ | OCH$_3$ | —OC(CH$_3$)$_2$C(O)NH-cyclopropyl |

TABLE 7

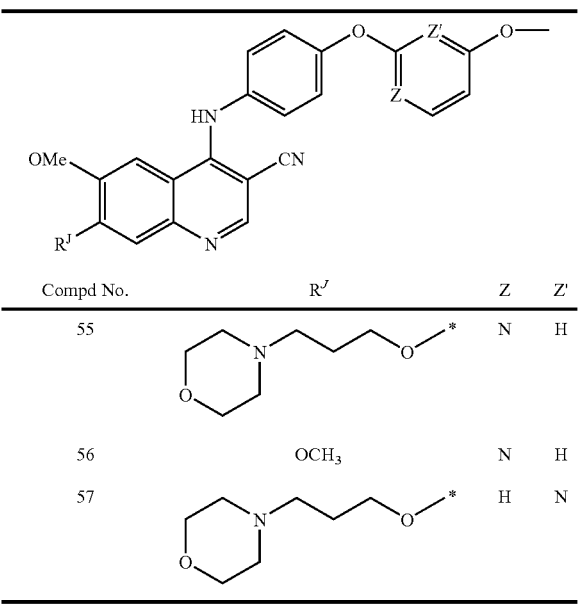

| Compd No. | $R^J$ | Z | Z' |
|---|---|---|---|
| 55 | | N | H |
| 56 | OCH$_3$ | N | H |
| 57 | | H | N |

TABLE 8

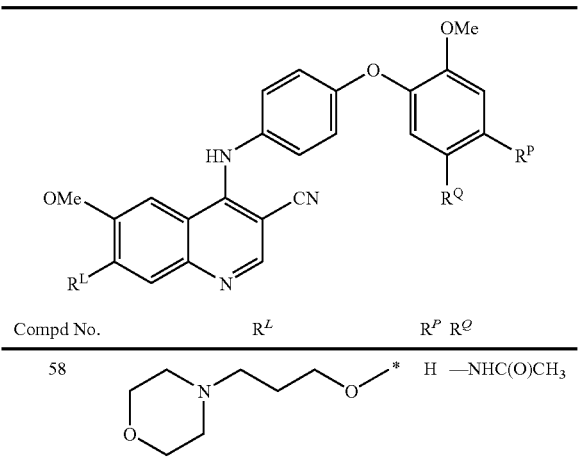

| Compd No. | $R^L$ | $R^P$ | $R^Q$ |
|---|---|---|---|
| 58 | morpholinopropoxy | H | —NHC(O)CH$_3$ |

TABLE 8-continued

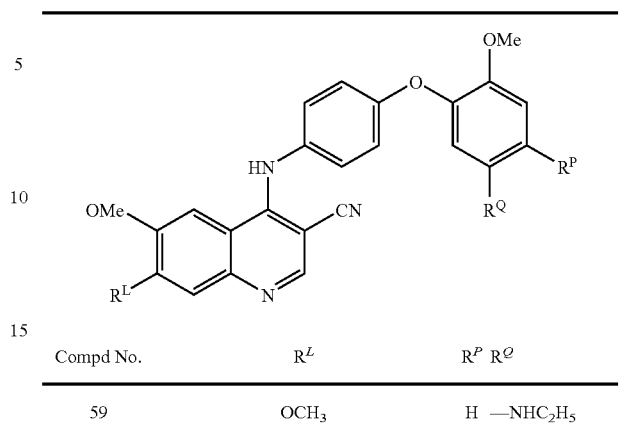

| Compd No. | $R^L$ | $R^P$ | $R^Q$ |
|---|---|---|---|
| 59 | OCH$_3$ | H | —NHC$_2$H$_5$ |
| 60 | morpholinopropoxy | H | —NHC$_2$H$_5$ |
| 61 | morpholinopropoxy | H | OCH$_3$ |
| 62 | piperidinopropoxy | F | H |
| 63 | OCH$_3$ | H | F |
| 64 | morpholinopropoxy | H | F |

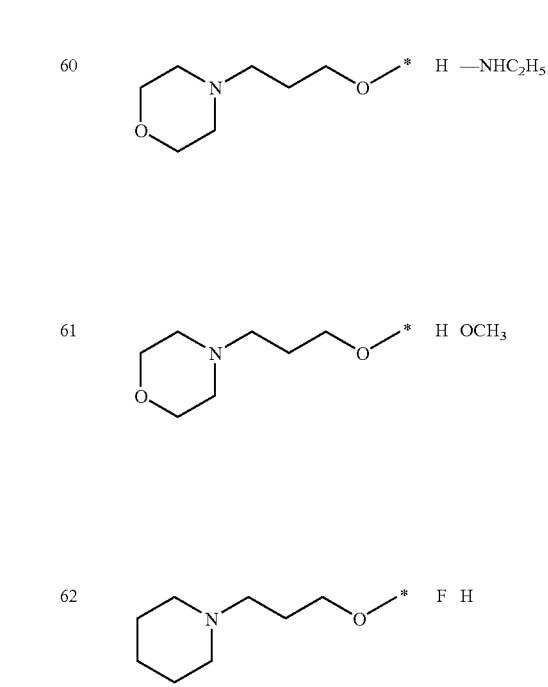
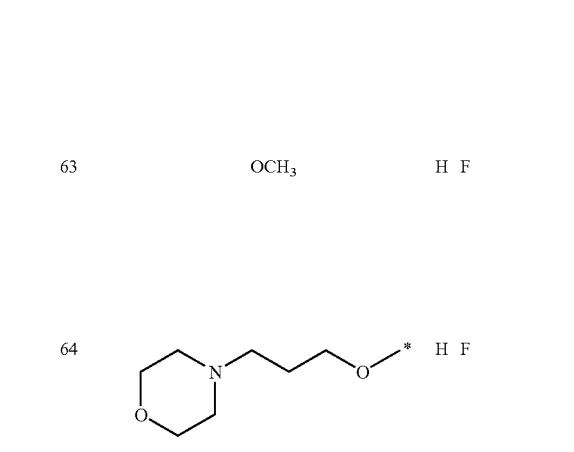

TABLE 9

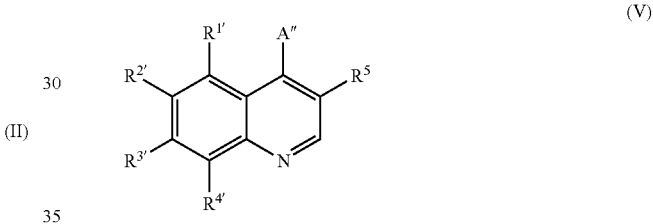

| Compd No. | $R^N$ | $R^M$ | $R^K$ |
|---|---|---|---|
| 65 | OCH₃ | —CO₂Et | —C₂H₅ |
| 66 | 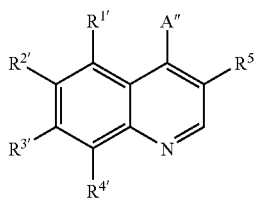 | —CO₂Et | —C₂H₅ |
| 67 | OCH₃ | —C(O)OCH₃ | —C₂H₅ |
| 68 | OCH₃ | —C(O)O(CH₂)₂CH₃ | —C₂H₅ |

Compounds of formula (I) or (IA) are suitably prepared by reacting a compound of formula (II)

(II)

where $R^{1'}$, $R^{2'}$, $R^{3'}$, $R^{4'}$ represent $R^1$, $R^2$, $R^3$ and $R^4$ respectively as defined in relation to formula (I) or a precursor thereof, $R^5$ is as defined in relation to formula (I) and A" is a leaving group, with a compound of formula (III)

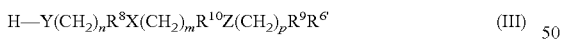

(III)

where Y, n, $R^8$, X, m, $R^{10}$, Z, p and $R^9$ are as defined in relation to formula (I), and $R^{6'}$ is a group $R^6$ as defined in relation to formula (I) or a precursor thereof; or with a compound of formula (IV)

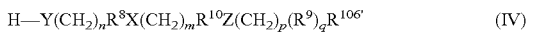

(IV)

where Y, n, $R^8$, X, m, $R^{10}$, Z, p, q and $R^9$ are as defined in relation to formula (IA) and $R^{106'}$ is a group $R^{106}$ as defined in relation to formula (IA) or a precursor thereof; and thereafter if necessary or desired converting precursor groups $R^{1'}$, $R^{2'}$, $R^{3'}$, $R^{4'}$, $R^{6'}$ and $R^{106'}$ to groups of formula $R^1$, $R^2$, $R^3$, $R^4$, $R^6$ and $R^{106}$ respectively, or converting a group $R^1$, $R^2$, $R^3$, $R^4$, $R^6$ and $R^{106}$ to a different such group.

Alternatively compounds of formula (IB) are suitably prepared by reacting a compound of formula (V)

(V)

where $R^{1'}$, $R^{2'}$, $R^{3'}$, $R^{4'}$ represent $R^1$, $R^2$, $R^3$ and $R^4$ respectively as defined in relation to formula (IB) or a precursor thereof, $R^5$ is as defined in relation to formula (IB) and A" is a leaving group, with a compound of formula (VI)

(VI)

where Y, n, $R^6$, X, m, $R^{108}$, $R^{109}$ and $R^{110}$ are as defined in relation to formula (IB), and hereafter if necessary or desired converting precursor groups $R^{1'}$, $R^{2'}$, $R^{3'}$ and $R^{4'}$ to groups of formula $R^1$, $R^2$, $R^3$ and $R^4$ respectively, or converting a group $R^1$, $R^2$, $R^3$ and $R^4$ to a different such group.

Suitable leaving groups for A" include halogen such as bromo or chloro, or a mesylate or tosylate group or a substituted phenoxy group.

The reaction is suitably carried out in an organic solvent such as an alcohol for example propanol or cyclohexanol at elevated temperatures, for example of from 50 to 150° C., for example at about 105° C.

Conversion reactions in which precursor groups $R^{1'}$, $R^{2'}$, $R^{3'}$, $R^{4'}$ are converted to groups of formula $R^1$, $R^2$, $R^3$ and $R^4$ respectively, or groups $R^1$, $R^2$, $R^3$ and $R^4$ are converted to different such group can be carried out using conventional chemistry as outlined hereinafter. Particular precursor groups $R^{1'}$, $R^{2'}$, $R^{3'}$, $R^{4'}$ are groups of formula $R^{13'}—X^1—(CH_2)_x$ wherein x and $X^1$ are as defined herein, and $R^{13'}$ is $C_{1-5}$alkyl which is substituted with halo other than fluoro, and in particular chloro or bromo. The chloro or bromo group may readily be converted into many other groups $R^{13}$ as defined in relation to formula (I).

Similarly conversion reactions involving groups $R^6$ or $R^{106}$ may be effected using conventional chemistry. For example substituent groups on a group $R^{10}$ within the group $R^6$ or $R^{106}$ may be changed, for example by changing acids to esters or amides etc.

Alternatively, compounds of formula (I) or (IA) are prepared by reacting a compound of formula (VII)

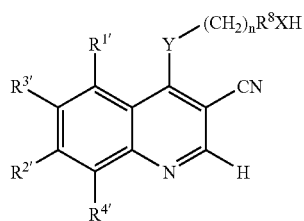
(VII)

where $R^{1'}$, $R^{2'}$, $R^{3'}$, $R^{4'}$ are as defined in relation to formula (ID) $R^8$, X, Y and n are as defined in relation to formula (I) or formula (IA), with a compound of formula (VIII)

$A''\text{-}(CH_2)_m R^{10} Z (CH_2)_p R^9 R^{6'}$ (VIII)

where m, $R^{10}$, Z, p and $R^9$ are as defined in relation to formula (I), $R^{6'}$ is a as defined in relation to formula (III) and A" is a leaving group; or with a compound of formula (IX)

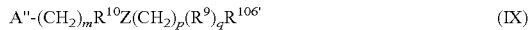
$A''\text{-}(CH_2)_m R^{10} Z (CH_2)_p (R^9)_q R^{106'}$ (IX)

where m, $R^{10}$, Z, p, q, and $R^9$ are as defined in relation to formula (IA) and $R^{106'}$ is a group $R^{106}$ as defined in relation to formula (IA) or a precursor thereof and A" is a leaving group; and thereafter if necessary or desired converting precursor groups $R^{1'}$, $R^{2'}$, $R^{3'}$, $R^{4'}$, $R^{6'}$ and $R^{106'}$ to groups of formula $R^1$, $R^2$, $R^3$, $R^4$ and $R^6$ respectively, or converting a group $R^1$, $R^2$, $R^3$, $R^4$ and $R^6$ and $R^{106}$ to a different such group. Suitable leaving groups for A" include halogen such a bromo or chloro, or a mesylate or tosylate group.

The reaction is suitably carried out in an organic solvent such as DMF at elevated temperatures, for example of from 40 to 120° C., for example at about 80° C. Conversion reactions are conventional and can be derived from literature information.

For example, where Y is NH, compounds of formula (III) are suitably prepared by reduction of a compound of formula (X)

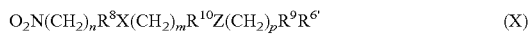
$O_2N(CH_2)_n R^8 X (CH_2)_m R^{10} Z (CH_2)_p R^9 R^{6'}$ (X)

where X, $R^8$, $R^9$, $R^{10}$, Z, $R^{6'}$ m, p and n are as defined above. It may be convenient to convert precursor groups $R^{6'}$ to groups $R^6$ or groups $R^6$ to other such groups at the level of compound of formula (X) or (III) using conventional chemistry. A similar process can be used to make compounds of formula (IV).

Compounds of formula (VI) are also known compounds or they can be prepared from known compounds by conventional methods.

Alternatively, compounds of formula (IB) are prepared by reacting a compound of formula (XI)

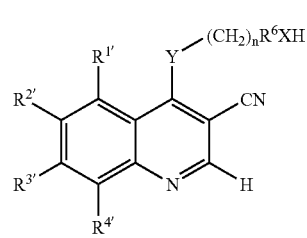
(XI)

where $R^{1'}$, $R^{2'}$, $R^{3'}$, $R^{4'}$ are as defined in relation to formula (IB) $R^6$, X, Y and n are as defined in relation to formula (I), with a compound of formula (XII)

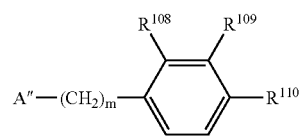
(XII)

where m, $R^{108}$, $R^{109}$ and $R^{110}$ are as defined in relation to formula (IB), and A" is a leaving group; and thereafter if necessary or desired converting precursor groups $R^{1'}$, $R^{2'}$, $R^{3'}$ and $R^{4'}$ to groups of formula $R^1$, $R^2$, $R^3$ and $R^4$ respectively, or converting a group $R^1$, $R^2$, $R^3$ and $R^4$ to a different such group. Suitable leaving groups for A" include halogen such a bromo or chloro, or a mesylate or tosylate group.

The reaction is suitably carried out in an organic solvent such as DMF at elevated temperatures, for example of from 40 to 120° C., for example at about 80° C. Conversion reactions are conventional and can be derived from literature information.

Compounds of formula (II), (V), (VII) and (XI) are either known compounds or they can be prepared from known compounds by conventional methods, for example as described in WO 98/43960 and WO 98/13350.

Compounds of formula (III), (IV), (VI) and (VI) are also known compounds (see for example Rev. Chim. (Bucharest) (1988), 39(6), 477-82 and DD 110651: 74.01.05) or they can be prepared from known compounds using conventional methods.

Compounds of the invention are useful in the inhibition of MEK enzyme activity and can be used in the treatment of proliferative disease. They will suitably be in the form of a pharmaceutical composition, in combination with a pharmaceutically acceptable carrier. Such compositions form a further aspect of the invention.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl 2-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, and esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 301 or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of formula (I), (IA) or (IB) will naturally vary according to the nature and severity of the conditions, the age and sex of the animal or patient and the route of administration, according to well known principles of medicine. As mentioned above, compounds of formula (I), (IA) or (IB) are useful in treating diseases or medical conditions which are due alone or in part to the effects MEK enzymes.

In using a compound of formula (I), (IB) or (IC) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

According to a further aspect of the invention there is provided a compound of the formula (I), (IA) or (IB) or a pharmaceutically-acceptable salt or prodrug or solvate thereof, as defined hereinbefore, for use in a method of treatment of the human or animal body by therapy.

We have found that the compounds of the present invention possess potent anti-tumour activity which it is believed is obtained by way of inhibition the MAPK pathway and, in particular, inhibition of MEK enzyme Accordingly the compounds of the present invention are of value as anti-proliferative agents.

Thus according to an aspect of the invention there is provided the use of a compound of formula (I), (IA) or (IB) or a pharmaceutically-acceptable salt, prodrug or solvate thereof, as defined hereinbefore in the manufacture of a medicament for use as an anti-proliferative agent in the containment and/or treatment of solid tumour disease.

According to a further feature of this aspect of the invention there is provided a method for producing an anti-proliferative effect by the containment and/or treatment of solid tumour disease in a warm-blooded animal, such as man, in need of such treatment which comprises administering to said animal an effective amount of a compound of formula (I), (IA) or (IB) or a pharmaceutically-acceptable salt thereof, prodrug or solvate thereof as defined hereinbefore.

According to a further aspect of the invention there is provided the use of a compound of formula (I), (IA), (IB) or a pharmaceutically-acceptable salt thereof, prodrug or solvate thereof as defined hereinbefore in the manufacture of a medicament for use in the prevention or treatment of solid tumour disease in a warm-blooded animal such as man.

According to a further feature of this aspect of the invention there is provided a method for the prevention or treatment of solid tumour disease in a warm-blooded animal, such as man, in need of such treatment which comprises administering to said animal an effective amount of a compound of formula (I), (A), (IB) or a pharmaceutically-acceptable salt thereof, prodrug or solvate thereof as defined hereinbefore According to a further aspect of the invention there is provided the use of a compound of formula (I), (IA), (IB) or a pharmaceutically-acceptable salt thereof, prodrug or solvate thereof as defined hereinbefore in the manufacture of a medicament for use in the prevention or treatment of those tumours which are sensitive to inhibition of MEK enzymes.

According to a further feature of this aspect of the invention there is provided a method for the prevention or treatment of those tumours which are sensitive to inhibition of MEK enzymes which comprises administering to said animal an effective amount of a compound of formula (I), (IA), (IB) or a pharmaceutically-acceptable salt thereof, prodrug or solvate thereof as defined hereinbefore.

The anti-proliferative treatment defined hereinbefore may be applied as a sole therapy or may involve, in addition to the compounds of the invention, conventional surgery or radiotherapy or chemotherapy. Such chemotherapy may include one or more of the following categories of anti-tumour agents:—

(i) anti-invasion agents (for example metalloproteinase inhibitors like marimastat and inhibitors of urokinase plasminogen activator receptor function);

(ii) other antiproliferative or antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea, or, for example, one of the preferred antimetabolites disclosed in European Patent Application No. 562734 such as (2S)-2-{o-fluoro-p-[N-{2,7-dimethyl-4-oxo-3,4-dihydroquinazolin-6-ylmethyl)-
N-(prop-2-ynyl)amino]benzamido}-4-(tetrazol-5-yl) butyric acid); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, aimsacrine, topotecan and camptothecin);

(iii) cytostatic agents such as antioestrogens (for example tamoxifen, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrazole, vorazole and exemestane) and inhibitors of 5α-reductase such as finasteride;

(iv) inhibitors of growth factor function, for example such inhibitors include growth factor antibodies, growth factor receptor antibodies, tyrosine kinase inhibitors and serine/threonine kinase inhibitors, for example inhibitors of the epidermal growth factor family (for example the EGFR tyrosine kinase inhibitors N-(3-chloro-4-fluorophenyl)-7-methoxy-6-(3-morpholinopropoxy)quinazolin-4-amine (ZD1839), N-(3-ethynylphenyl)-6,7-bis(2-methoxyethoxy)quinazolin-4-amine (CP 358774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family, and (v) antiangiogenic agents such as those which inhibit vascular endothelial growth factor such as the compounds disclosed in International Patent Applications WO 97/22596, WO 97/30035, WO 97/32856 and WO 98/13354 and those that work by other mechanisms (for example linomide, inhibitors of integrin αvβ3 function and angiostatin).

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a compound of formula (I), (IA), (IB) or a pharmaceutically-acceptable salt thereof, prodrug or solvate thereof as defined hereinbefore and an additional anti-tumour agent as defined hereinbefore for the conjoint treatment of cancer.

Although the compounds of the present invention are primarily of value as therapeutic agents for use in warm-blooded animals (including man), they are also useful whenever it is required to inhibit the effects of MEK enzyme. Thus, they are useful as pharmacological standards for use in the development of new biological tests and in the search for new pharmacological agents.

The invention will now be particularly described by way of the following non-limiting example.

EXAMPLES

In the examples the following abbreviations have been used.

| | |
|---|---|
| DMF | N,N-dimethylformamide |
| THF | tetrahydrofuran |
| DMSO | dimethyl acetamide |
| DEAD | diethyl azodicarboxylate |
| Ph$_3$P | triphenylphosphine |
| EDC | ethylene dichloride (1,2-dichloroethane) |
| DCM | dichloromethane (methylenechloride) |
| DMAP | dimethylaminepyridine |
| HOBT | N-hydroxybenzotriazole |
| EDAC | 1-(3-dimethylaminopropyl)-3-ethyl-carbodiimide |
| KHMDS | potassium hexamethyldisilazane (potassium bis(trimethylsilyl)amide) |

Preparation of Key Intermediates a) Chloroquinoline Intermediates—Intermediate A

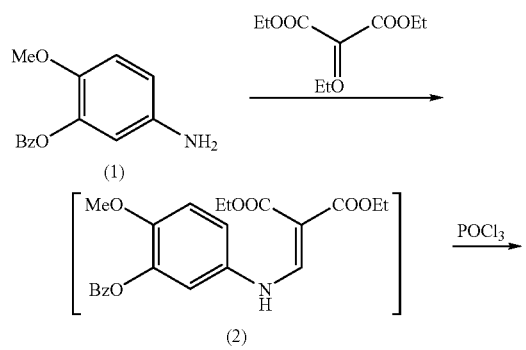

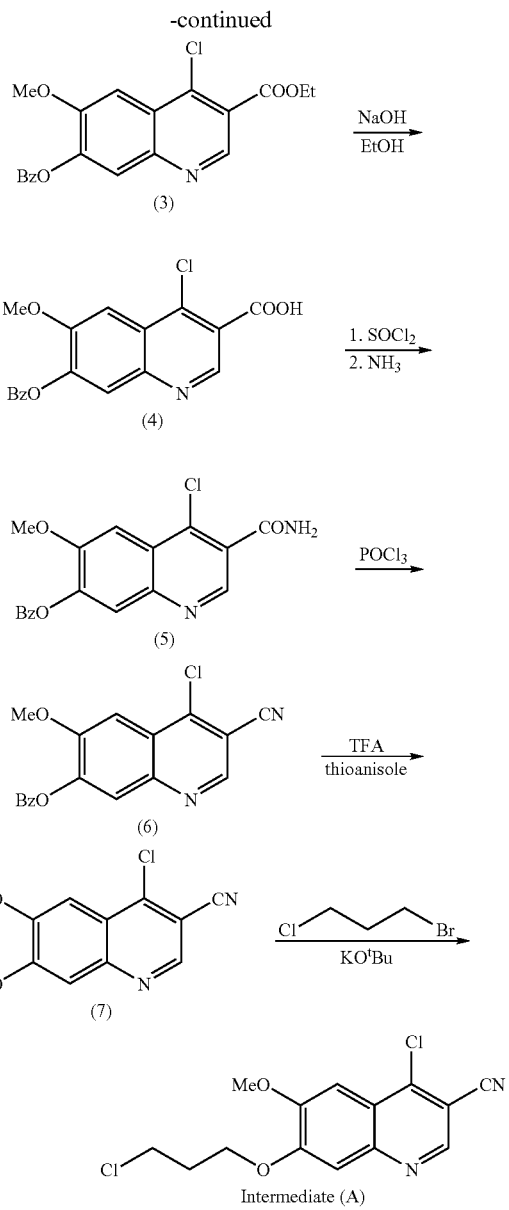

A mixture of (1)(10.36 g., 45.3 mmole) and diethyl-ethoxymethylene malonate (9 mL, 45.3 mmole) was heated at 110° C. for 1 hour and then allowed to cool overnight. The mixture was evaporated and the product (2) used in the next step without further purification.

Mass Spectrum m/e 400 (M$^+$+H).

Preparation of (3)

A mixture of (2)(assumed 45.3 mmole) and phosphoryl chloride (83.3 mL, 906 mmole) was heated at 115° C. for 18 hours. After cooling, the solution was evaporated to remove excess phosphoryl chloride. The residue was treated with ice and aqueous ammonia to hydrolyse the remaining phosphoryl chloride. The solid product was filtered off and dried in a vacuum oven to give a cream coloured solid, 9.0 g (53% yield).

Mass Spectrum W/e 372 (M$^+$+H).

Preparation of (4)

A mixture of (3)(9.0 g, 24.2 mmole) was stirred in ethanol (48.3 mL) for 15 minutes at ambient temperature to give a smooth suspension. Aqueous sodium hydroxide solution (2.0M, 48.3 mL, 96.7 mole) was added and the mixture stirred for 18 hours at ambient temperature. The ethanol was removed by rotary evaporation and the resulting solution was acidified to pH 2 with hydrochloric acid while stirring. The precipitate was filtered off and dried in a vacuum oven to give an orange solid, 7.19 g (86% yield).

Mass Spectrum m/e 344 ($M^+$+H).

Preparation of (5)

A mixture of (4)(7.18 g, 20.9 mmole) and thionyl chloride (90 mL) was refluxed for 2 hours. After cooling the excess thionyl chloride was removed by rotary evaporation and the residue was suspended in acetone (175 mL) and the resulting suspension cooled in an ice-bath. Aqueous ammonia (S.G. 0.880, 20 mL) was added gradually, keeping the temperature below 10° C. The resulting suspension was filtered off, washed with water and air-dried to give a solid, 5.15 g (75% yield).

Mass Spectrum m/e 343 ($M^+$+H).

Preparation of (6)

A mixture of (5)(20.55 g, 60 mmole) and phosphoryl chloride (250 mL) was heated and stirred at 120° C. for 4 hours when the starting material had dissolved. Heating and stirring was continued at 110° C. for 18 hours. After cooling, the solution was evaporated to remove excess phosphoryl chloride. Last traces of phosphoryl chloride were removed by azeotroping with toluene. The residue was treated with ice and aqueous ammonia to remove acidity. The solid product was filtered off and dried in a vacuum oven to give a grey solid, 19.23 g (99% yield).

(This may also be prepared as described in WO 9843960)

Mass Spectrum m/e 325 ($M^+$+H).

Preparation of (7)

A mixture of (6)(19.23 g, 60.0 mmole) and trifluoroacetic acid (300 ml) and thioanisole (35 ml) was refluxed in a nitrogen atmosphere for 3 hours. After cooling the trifluoroacetic acid was removed by rotary evaporation and the oily residue was stirred with ice and water and basified with aqueous ammonia (S.G. 0.880). The resulting suspension was filtered and the solid was washed successively with water, ethyl acetate and diethyl ether and then dried to give a khaki solid, 13.74 g (97% yield).

Mass Spectrum m/e 235 ($M^+$+H).

Preparation of (8)

Potassium tert-butoxide (5.0 g) was added portionwise to a stirred solution of (7)(10 g) in DMA (200 ml) cooled to 5° C. under an atmosphere of nitrogen. The mixture was stirred at ambient temperature for 30 min and then cooled to 5° C. 1-chloro-3-bromopropane (7.4 g) was added followed by tetrabutylammonium iodide (1.57 g) and 18-crown-6 (0.5 g) and the mixture stirred at ambient temperature for 16 hr. The DMA was removed in vacuo and the residue partitioned between ethyl acetate and water. The organic extracts were dried and evaporated to dryness. The product was purified by flash column chromatography on silica eluting with 1-2% methanol in dichloromethane to give (8) as a white solid (6.5 g).

Mass Spectrum m/e 311 ($M^+$+H).

a1) Preparation of Intermediate A1-(4-chloro-6-methoxy-7-[3-(1-morpholino)propoxy]-3-quinolinecarbonitrile)

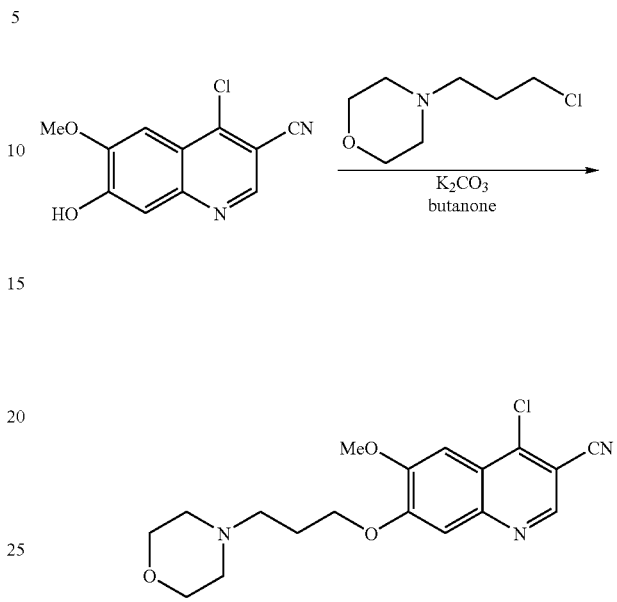

A mixture of 4-chloro-6-methoxy-7-hydroxy-3-quinolinecarbonitrile (2.34 g, 10.0 mmole) and 1-(3-chloropropyl) morpholine (2.45 g, 15.0 mmole) and anhydrous potassium carbonate (2.07 g, 15.0 mmole) suspended in butanone (150 mL) was stirred in a oil-bath at 88° C. for 96 hours. The suspension was filtered hot to remove inorganics and the filtrate was allowed to cool and then evaporated to ca. 100 mL. A solid precipitated on standing for 72 hours. The solid was filtered off and washed with a little acetone and then dried to give a white solid, 0.54 g (15% yield).

Mass Spectrum m/e 362 ($M^+$+H).

b) Preparation of Intermediate B

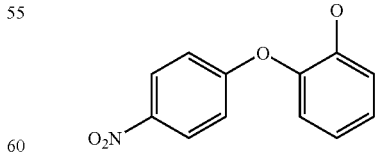

Intermediate B

This was prepared by reacting 2-hydroxyphenol (25 g) with 4-fluoronitrobenzene (32 g) in DMA (250 ml) in the presence of potassium tert-butoxide (26.7 g) at 140-160° C. for 30 min. NMR Spectrum (d-6-DMSO, d values) 6.87 (m, 1H), 6.99 (m, 3H), 7.10 (m, 2H), 8.18 (m, 2H), 9.76 (s, 1H)

c) Preparation of Intermediate C

The compound was prepared as outlined in the following scheme

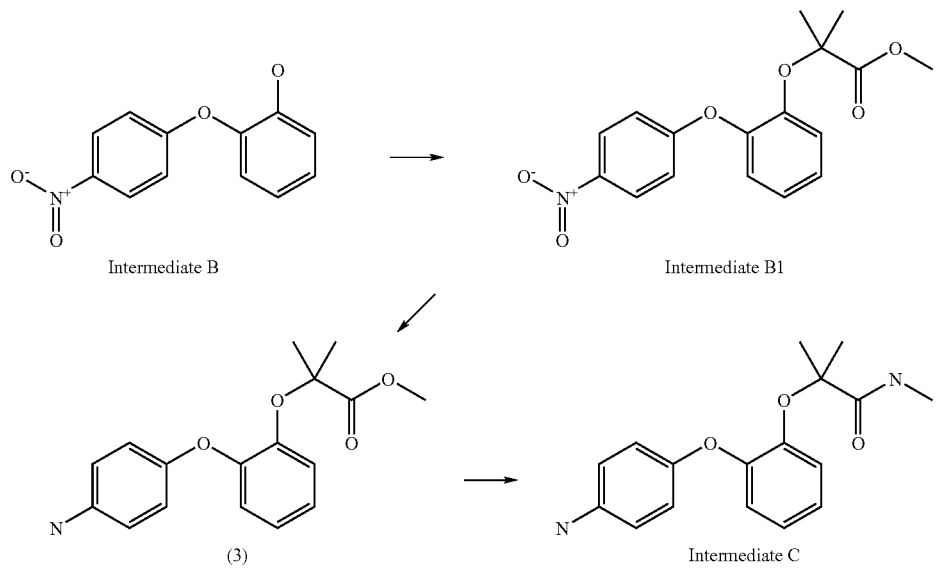

Step 1

Intermediate B was reacted with methyl 2-hydroxyisobutyrate in THF at room temperature for 16 hr using triphenylphosphine/DEAD as the coupling reagent to give intermediate B1 after chromatography.

Mass Spectrum m/e 332.3 (M+H)⁺

Step 2

Intermediate B1 was reduced to the corresponding aniline by reduction, at room temperature in ethyl acetate solution, with hydrogen and catalytic 5% Pd/C to give intermediate 3.

Mass Spectrum m/e 302.38 (M+H)⁺

Step 3

Intermediate 3 was converted to the amide by reaction with methylamine in ethanol for 16 hr at room temperature. The product was purified by chromatography to give intermediate C.

Mass Spectrum m/e 301.36 d) Preparation of Intermediate D

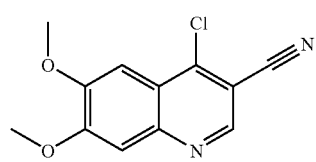

This was prepared as described in WO 9843960, example 34.

e) Preparation of Intermediates E and F

The compounds were prepared as outlined in the following scheme.

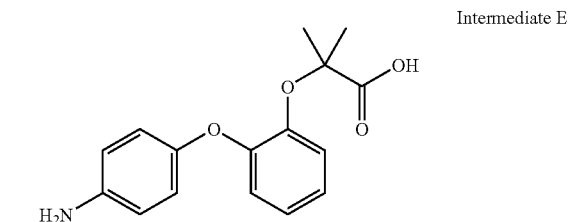
Intermediate E

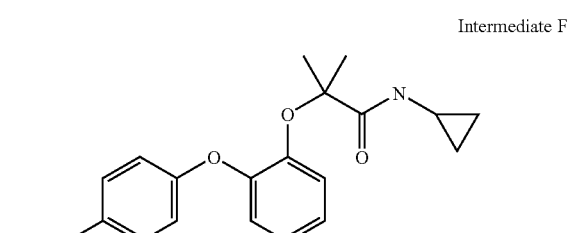
Intermediate F

Step 1

Steps 1 and 2 of the preparation described above to make Intermediate C were followed to prepare intermediate 3.

Step 2

Intermediate 3 was converted to the hydroxide (Intermediate E in the above scheme) by reaction with sodium hydroxide in methanol for 18 hr at room temperature Mass Spectrum m/e 288.3 (M⁺H)

Step 3
Intermediate E was converted to Intermediate F by reaction with cyclopropylamine in the presence of DMAP/EDC/DCM at room temperature for 18 hrs. The product was purified by chromatography Mass Spectrum m/e 327.3 (M+H)+.

Example 1

Preparation of Compound 1 in Table 1

The compound was prepared using the synthesis outlined in the following scheme:

tracted and the combined organic phase washed with water and brine, dried, filtered and concentrated. The residue was purified by column chromatography using 35-40% ethyl acetate in hexane as eluent to yield Intermediate (2).

Mass Spectrum m/e 344 (M++H)

Step 3
Intermediate 2 (93 mg, 0.27 mmol) was suspended in 1:1 ethanol:water (3 ml), $Na_2S_2O_4$ (418 mg, 2.4 mmol) was added and the reaction heated at 100° C. for 15 min. The reaction was cooled, 2M aqueous sodium hydroxide solution was added and the reaction was stirred for 1 hr. The aqueous phase was extracted with ethyl acetate (2×) and the combined

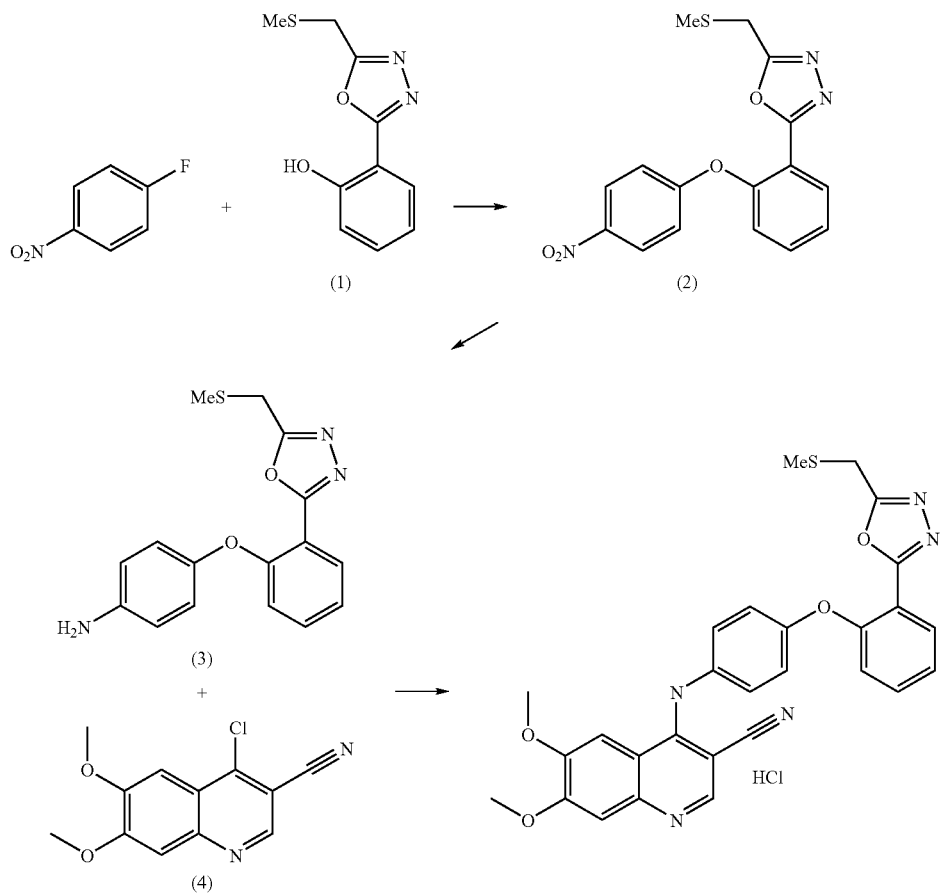

Step 1
Intermediate (1) was prepared by heating salicylic hydrazide (1.52 g, 10 mmol) in $MeSCH_2C(OMe)_3$ (15 ml) at 100° C. for 18 hrs.

Mass Spectrum m/e 223 (M++H)

Step 2
The product of step 1 (1.745 g, 7.9 mmol) was dissolved in DMA (15 ml), potassium tert-butoxide (953 mg, 7.9 mmol) was added and the reaction was stirred at ambient temperature for 10 minutes. Para-fluoronitrobenzene (1.11 g, 7.9 mmol) was added and the reaction was heated to 150° C. for 90 min. The reaction was cooled and concentrated in vacuo. The residue was partitioned between ethyl acetate and 2M aqueous sodium hydroxide solution. The aqueous phase was reexorganic extracts were washed with water and brine, dried, filtered and concentrated to give, Intermediate (3).

Mass Spectrum m/e 314 (M++H)

Step 4
Intermediate (3) from step 3 above (31 mg, 0.1 mmol) was mixed with 4-chloro-3-cyano-6,7-dimethoxy quinoline (4) (23 mg, 0.09 mmol), prepared as described WO 9843960, in 1-propanol (3 ml) and the mixture was stirred and heated at 110° C. for 18 hours. The mixture was cooled to ambient temperature and then filtered. The crystals were washed with a small volume of 1-propanol and then dried to give compound 1.

Mass Spectrum m/e 526 (M++H)

NMR Spectrum (d-6-DMSO, d values) 2.10, (s, 3H), 4.00 (s, 3H), 4.00 (s, 3H), 4.00 (s, 2H), 7.15 (m, 3H), 7.35 (t, 1H), 7.45 (d, 2H), 7.45 (s, 1H), 7.60 (t, 1H), 8.00 (d, 1H), 8.20 (s, 1H), 8.90 (s, 1H), 11.20 (br s, 1H).

Example 2

Preparation of Compound 2 in Table 1

Compound No 1 (56 mg, 0.1 mmol) prepared as described in Example 1 was suspended in acetic acid (2.7 ml). Peracetic acid (39% in acetic acid, 0.05 ml, 0.29 mmol) was added dropwise and the reaction was stirred overnight. A further portion of peracetic acid (0.05 ml) was added and the reaction stirred overnight again. The reaction was concentrated in vacuo and the residue suspended in dichloromethane. Potassium carbonate was added and the mixture stirred for 30 min at ambient temperature. The reaction was filtered and concentrated to a residue which was purified by Bond Elut chromatography eluting with DCM increasing to 1.5% methanol in DCM to give, Compound No. 2.

Mass Spectrum m/e 558 (M⁺+H)

NMR Spectrum (CDCl₃, δ values) 3.10, (s, 3H), 3.80 (s, 3H), 4.00 (s, 3H), 4.60 (s, 2H), 7.00 (d, 2H), 7.10 (d, 1H), 7.10 (s, 1H), 7.10 (br s, 1H), 7.15 (d, 2H), 7.25 (s, 1H), 7.30 (t, 1H), 7.55 (t, 1H), 8.10 (dd, 1H), 8.55 (s, 1H)

Example 3

Preparation of Compound No. 3 in Table 1

The compound was prepared as outlined in the following scheme:

Step 1:

4-nitro-fluorobenzene and 2-(carboxymethoxy)phenol were reacted together in DMA in the presence of potassium butoxide for 2 hours at 150° C. to yield 4-(2-carboxymethoxy)-phenoxy)nitrobenzene.

Mass Spectrum m/e 288 (M−H⁺)⁻

Step 2

A solution of the product of step 1 in DMA was then coupled with methyl glycine using 1-(3-dimethylaminopropyl)-3-ethylcarbodiimide (EDAC), dimethylaminopyridine (DMA) and N-hydroxybenzotriazole (HOBT) to yield the intermediate of formula

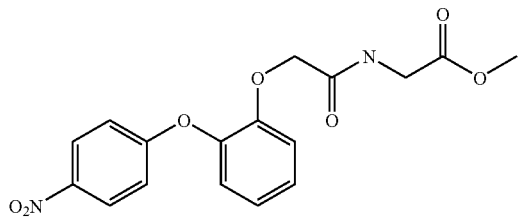

Mass Spectrum m/e 361.17 (M⁺+H).

Step 3

Reduction of the product of step 2 to the corresponding amine (Intermediate 1), was effected by hydrogenation in the presence of a 5% Pd/C catalyst.

Mass Spectrum m/e 331.14 (M⁺+H).

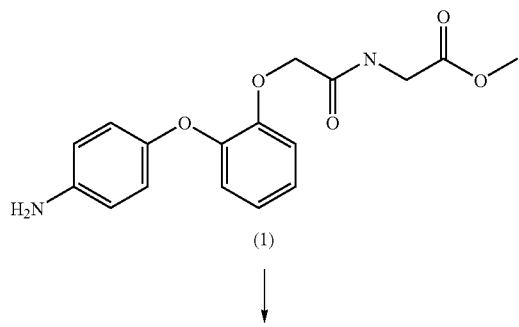

(1)

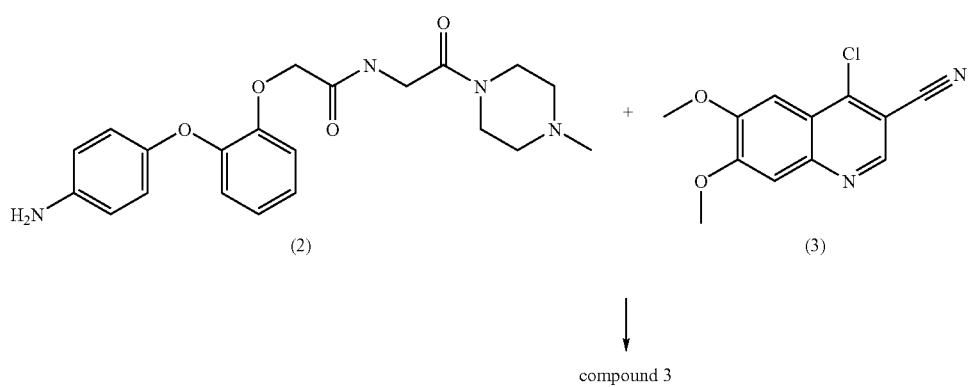

(2)     (3)

compound 3

Step 4

Intermediate (1)(300 mg) was reacted with N-methylpiperazine (1 ml) in methanol (10 ml) for 3 days at reflux. The product was purified by flash column chromatography to yield Intermediate 2 above (240 mg) as a gum.

Mass Spectrum m/e 399.36 (M$^+$+H).

Step 5

Intermediate (2) from step 4 above (230 mg) was mixed with 4-chloro-3-cyano-6,7-dimethoxy quinoline (intermediate 3) (143 mg), prepared as described WO 9843960, in 1-propanol (15 ml) and a solution of 1M hydrogen chloride in ether (0.6 ml) was added. The mixture was stirred and heated at 100° C. for 2 hours. The mixture was cooled to ambient temperature and then filtered. The crystals were washed with a small volume of 1-propanol and then dried to give the final product, Compound No. 3 (332 mg) as a yellow solid.

Mass Spectrum m/e 611.31 (M$^+$+H).

NMR Spectrum (d-6-DMSO, δ values) 2.72 (s, 3H), 2.80-3.60 (m, 6H), 3.92-4.23 (m, 3H), 3.98 (d, 6H), 4.27-4.48 (m, 1H), 4.57 (s, 2H), 6.94-7.1 (m, 4H), 7.14 (d, 2H), 7.40 (d, 2H), 7.48 (s, 1H), 7.85 (t, 1H), 8.21 (s, 1H), 8.89 (s, 1H), 11.02-11.18 (br.s, 1H), 11.18-11.26 (br.s, 1H).

Example 4

Preparation of Compound No 4

The compound was prepared as outlined in the following scheme:

Step 1

Intermediate B, described above (1 g) was reacted with epichlorohydrin (0.41 g) in tetrahydrofuran (50 ml) in the presence of potassium tert-butoxide (7.4 ml of 1M solution in THF) and 18-crown-6 ether for 2 hr at room temperature and 16 hr at reflux to produce intermediate 2 (0.95 g) in the above scheme.

Step 2

The product of step 1 was reacted with morpholine in n-propanol to produce intermediate 3.

Mass Spectrum m/e 375.29 (M$^+$+H).

Step 3

The product of step 2 was reduced with hydrogen and 5% Pd/C to produce intermediate 4.

Mass Spectrum m/e 345.41 (M$^+$+H).

Step 4

Intermediate D was reacted intermediate 4 in n-propanol solution at 100° C. for 2 hr to give the title product.

Mass Spectrum m/e 557.40 (M$^+$+H).

NMR Spectrum (d-6-DMSO, δ values) 2.93-3.66 (m, 6H), 3.7-3.95 (m, 6H), 3.98 (s, 3H), 4.01 (s, 3H), 4.26 (m, 1H),

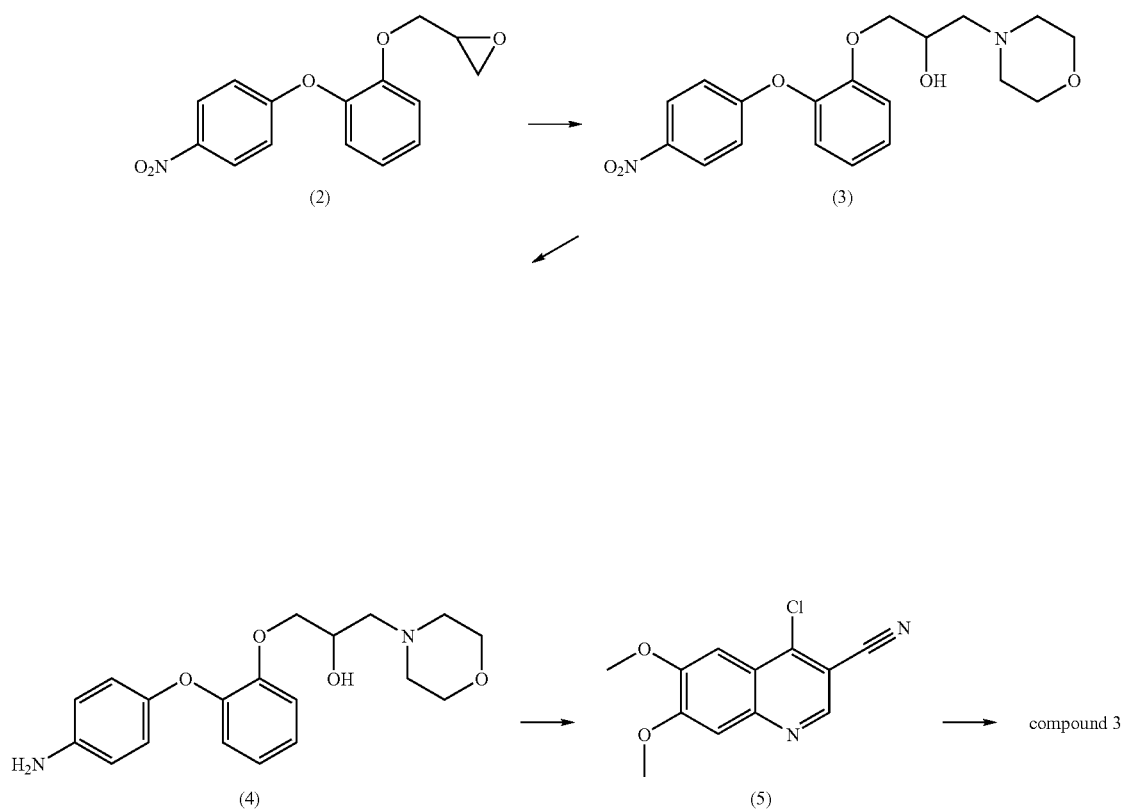

6.95-7.07 (m, 3H), 7.1 (d, 1H), 7.2 (m, 2H), 7.4 (d, 2H), 7.49 (s, 1H), 8.32 (s, 1H), 8.89 (s, 1H).

Example 5

Preparation of Compound No. 5 in Table 1

The title compound was prepared by a method analogous to that described in Example 4 but using piperidine instead of morpholine in step 3.

Mass Spectrum m/e 555.33 (M⁺+H).

NMR Spectrum (d-6-DMSO, d values) 1.27-1.48 (m, 1H), 1.56-1.91 (m, 5H), 2.8-3.05 (m, 4H), 3.25-3.39 (m, 2H), 3.82-3.97 (m, 2H), 3.98 (s, 3H), 4.00 (s, 3H), 4.2 (m, 1H), 6.93-7.08 (m, 3H), 7.11 (d, 1H), 7.2 (m, 2H), 7.40 (d, 2H), 7.50 (s, 1H), 8.37 (s, 1H), 8.89 (s, 1H), 9.71 (br.s, 1H), 11.36-11.44 (br.s, 1H).

Example 6

Preparation of Compound No. 6 in Table 1

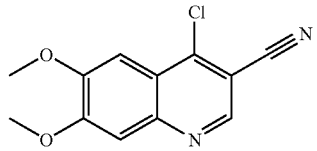

(1)

Intermediate C was reacted with (1) (prepared as described in WO 9843960) in n-propanol solution at 105° C. for 3 hr to give compound 6.

Mass Spectrum m/e 513.32 (M+H)⁺

NMR Spectrum (d-6-DMSO, δ values) 1.33 (s, 6H), 2.61 (d, 3H), 3.99 (s, 6H), 6.99 (d, 3H), 7.04-7.18 (m, 3H), 7.43 (d, 2H), 7.48 (s, 1H), 7.76 (m, 1H), 8.18 (s, 1H), 8.92 (s, 1H), 11.16 (bs, 1H).

Example 7

Preparation of Compound No. 7 in Table 1

The compound was prepared as outlined in the following scheme

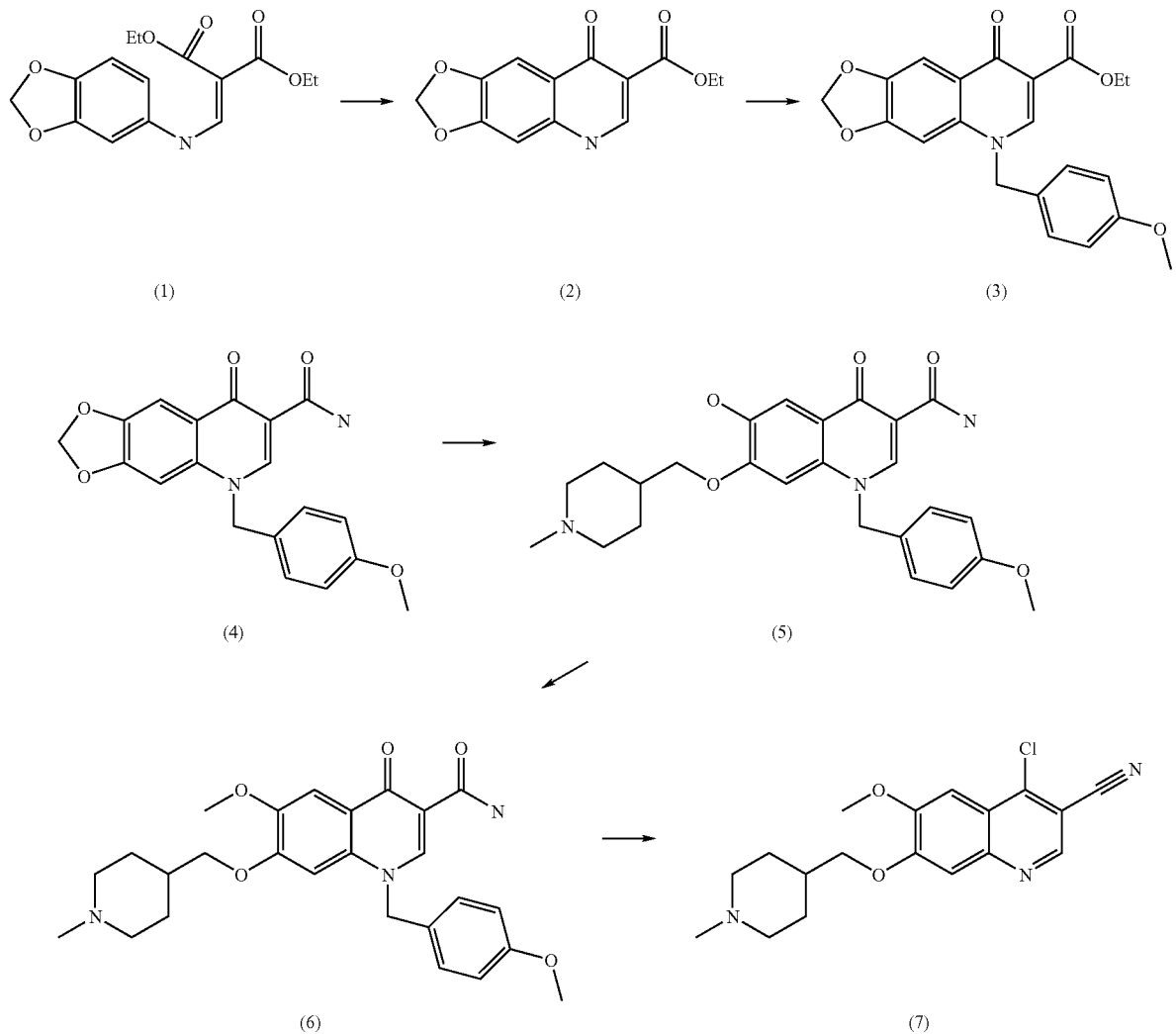

Step 1

Intermediate (1) was prepared by reacting together methylenedioxyaniline (51 g, 0.37 mol) and diethylethoxymethylenemalonate (75.1 ml, 0.37 mol) in ethanol at 80° C. for 1 hour.

NMR Spectrum (d-6-DMSO, δ values) 1.30 (t, 3H), 1.37 (t, 3H), 4.22 (q, 2H), 4.29 (q, 2H), 6.99 (s, 2H), 6.56 (m, 1H), 6.66 (d, 1H), 6.79 (d, 1H), 8.37 (d, 1H), 10.94 (bd, 1H).

Step 2

The product of step 1 was converted to Intermediate (2) above by contact with Dowtherm A for 1 hour at 250-260° C.

NMR Spectrum (d-6-DMSO, d values) 1.24 (t, 3H), 4.17 (q, 2H), 6.13 (s, 2H), 7.03 (s, 1H), 7.43 (s, 1H), 8.49 (s, 1H).

Step 3

Reaction of the product of step (2)(20.3 g,) with 4-methoxybenzylchloride (11.9 ml, 81.6 mmol) in DMA (200 ml) in the presence of potassium carbonate for 3 hours at 100° C. yielded Intermediate 3

Mass Spectrum m/e 382 (M+H)$^+$.

Step 4

The product of step 3 mixed with formamide (91.8 mmol, 3.5 equiv.) in DMA was heated at 60° C. Sodium methoxide (25% in methanol, 3.9 ml, 0.65 equiv.) was added and heating of the mixture continued for 90 mins to yield Intermediate 4 in the above scheme.

Mass Spectrum m/e 353 (M+H)$^+$.

Step 5

The product of step 4 was mixed with N-methyl-4-hydroxymethylpiperidine, potassium (tert)-butoxide and DMA and the mixture heated at 120° C. for 20 mins. Intermediate (5) was obtained after chromatography.

Mass Spectrum m/e 452 (M+H)$^+$.

Step 6

Intermediate (5) was mixed with methanol and PPh$_3$ in DCM and DEAD added, and the mixture allowed to react at room temperature for 18 hr to give intermediate 6.

Mass Spectrum m/e 466 (M+H)$^+$.

Step 7

The product of step 6 was then reacted with POCl$_3$ in MeCN for 18 hours at 110° C. to yield Intermediate 7 in the above scheme.

Mass Spectrum m/e 346, 348 (M+H)$^+$.

Step 8

Intermediate 7 was reacted with intermediate C (prepared as described above) in n-propanol solution at 100° C. for 3 hr to give, after chromatographic purification, compound 7.

Mass Spectrum m/e 610 (M+H)$^+$.

NMR Spectrum (d-6-DMSO+d-4-AcOH, δ values) 1.33 (s, 6H), 1.66 (m, 2H), 1.97 (m, 3H), 2.60 (s, 3H), 2.71 (s, 3H), 2.98 (m, 2H), 3.42 (m, 2H), 3.98 (s, 3H), 4.06 (2H, m), 6.97 (m, 4H), 7.09 (m, 3H), 7.41 (d, 2H), 7.55 (s, 1H), 8.24 (m, 1H), 8.87 (s, 1H).

Example 8

Preparation of Compound No. 8 in Table 1

(1)

Step 1

Intermediates A and C prepared as described above were reacted in n-propanol solution at 105° C. for 3 hr to give intermediate 1.

Mass Spectrum m/e 575.25 (M+H)$^+$

Step 2

Intermediate 1 was reacted with morpholine at room temperature for 72 hr in the presence of sodium iodide to give, after chromatographic purification, compound 8.

Mass Spectrum m/e 626.37 (M+H)$^+$

NMR Spectrum (d-6-DMSO D4 Acetic, δ values) 1.34 (s, 6H), 2.32 (m, 2H), 2.60 (s, 3H), 3.04 m-3.17 (m, 2H), 3.29 (t, 2H), 3.41-3.55 (m, 2H), 3.73-3.86 (m, 2H), 3.90-4.01 (m, 5H), 4.30 (t, 2H), 6.98 (d, 3H), 7.05-7.19 (m, 3H), 7.42 (d, 2H), 7.49 (s, 1H), 8.14 (s, 1H), 8.91 (s, 1H).

Example 9

Preparation of Compound 9 in Table 1

This was prepared as outlined in the following reaction scheme.

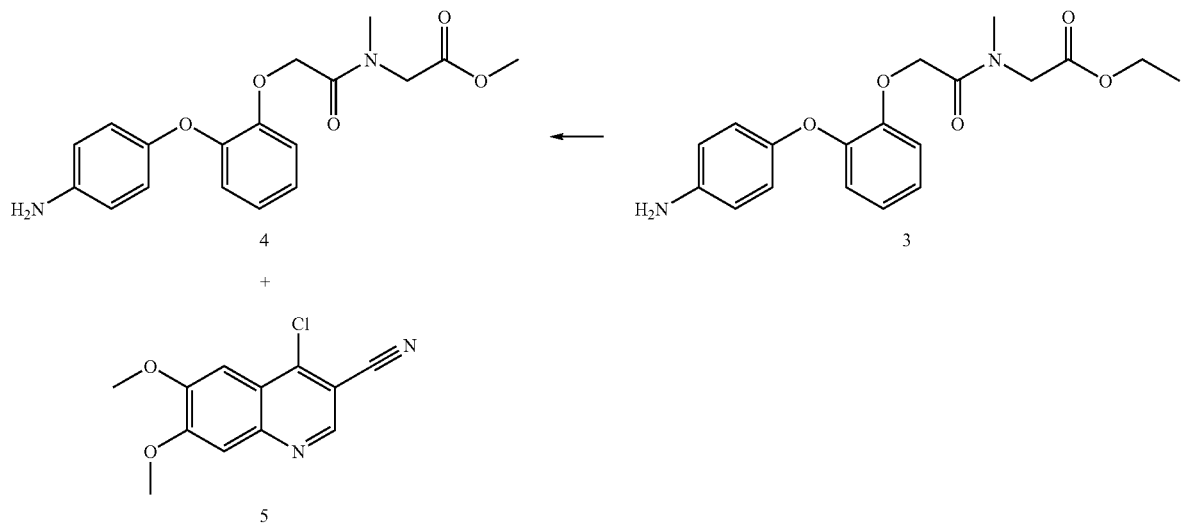

Step 1

4-nitro-fluorobenzene and 2-(carboxymethoxy)phenol were reacted together in DMA in the presence of potassium butoxide for 2 hours at 150° C. to yield 4-(2-carboxymethoxy-phenoxy)nitrobenzene, intermediate 1.

Mass Spectrum m/e 288 (M–H$^+$)$^-$

Step 2

A solution of the product of step 1 in DMA was then coupled with ethyl N-methylglycine using 1-(3-dimethylaminopropyl)-3-ethylcarbodiimide (EDAC), dimethylaminopyridine (DMAP) and N-hydroxybenzotriazole (HOBT) to yield intermediate 2.

Step 3

Reduction of the product of step 2 to the corresponding aniline, intermediate 3, was effected by hydrogenation in the presence of a 5% Pd/C catalyst.

Mass Spectrum m/e 359.38 (M$^+$+H).

Step 4

A methanolic solution of intermediate 3 was refluxed for several hours resulting in the production of intermediate 4.

Mass Spectrum m/e 345.32 (M$^+$+H).

Step 5

Intermediate 5 (prepared as described in WO 9843960) was reacted intermediate 4 in n-propanol solution at 100° C. for 2 hr to give the title product.

Mass Spectrum m/e 557.27 M$^+$+H).

NMR Spectrum (d-6-DMSO, δ values) 2.82&3.01 (2s, 3H), 3.62&3.68 (2s, 3H), 3.97 (2s, 6H), 4.08&4.27 (2s, 2H), 4.76&4.90 (2s, 2H), 6.89-7.06 (m, 5H), 7.06-7.20 (m, 1H), 7.4 (d, 2H), 7.41 (s, 1H), 8.08 (s, 1H), 8.9 (s, 1H), 10.90-11.00 (br.s, 1H).

Example 10

Preparation of Compound 10 in Table 1

The compound was prepared as outlined in the reaction scheme below

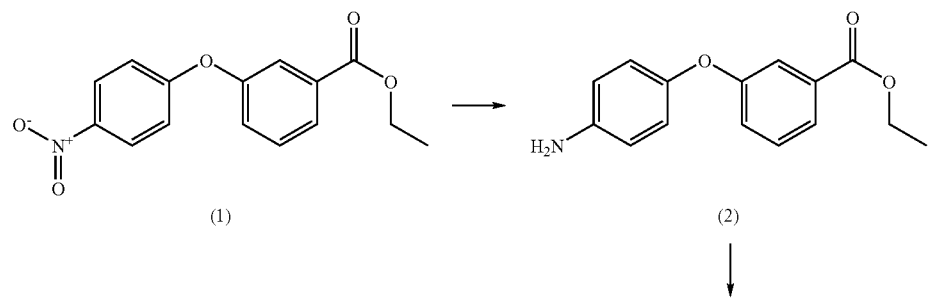

Step 1

4-fluoro-nitrobenzene and ethyl 3-hydroxybenzoate were reacted together in DMA in the presence of potassium butoxide for 2 hours at 150° C. to yield intermediate 1.

Mass Spectrum m/e 283.27 (M–H$^+$)$^-$

Step 2

Intermediate 1 was reduced to the corresponding aniline by reduction, at room temperature in ethyl acetate solution, with hydrogen and catalytic 5% Pd/C to give intermediate 2.

Mass Spectrum m/e 258.22 (M+H)$^+$

Step 3

Intermediate 2 was converted to the carboxylic acid by hydrolysis with 2M aqueous sodium hydroxide solution in ethanol for 16 hr at room temperature to give intermediate 3.

Mass Spectrum m/e 230.12 (M+H)$^+$

Step 4

Intermediate 3 was converted to the amide by condensation with cyclopropylamine using 1-(3-dimethylaminopropyl)-3-ethylcarbodiimide (EDAC) and dimethylaminopyridine (DMAP) in dichloromethane solution to yield, after chromatographic purification, intermediate 4.

Mass Spectrum m/e 269.27 (M+H)$^+$

Step 5

Intermediate 4 was reacted with intermediate A (prepared as described above) in n-propanol solution at 105° C. for 3 hr to give intermediate 5.

Mass Spectrum m/e 543.38 (M+H)$^+$

Step 6

Intermediate 5 was reacted with morpholine in the manner described for Example 8 Step 2 to yield, after chromatographic purification, compound 10.

Mass Spectrum m/e 594.30 (M+H)$^+$

NMR Spectrum (d-6-DMSO D4 Acetic, δ values) 0.73-0.80 (m, 2H), 0.82-0.90 (m, 2H), 2.27-2.37 (m, 2H), 2.76-2.85 (m, 1H), 3.03-3.17 (m, 2H), 3.29 (t, 2H), 3.41-3.54 (m, 2H), 3.72-3.87 (m, 2H), 3.93-4.01 (m, 5H), 4.30 (t, 2H), 7.13-7.19 (m, 3H), 7.42 (d, 1H), 7.45-7.51 (m, 4H), 7.59 (d, 1H), 8.16 (s, 1H), 8.91 (s, 1H).

Example 11

Preparation of Compound No 11 in Table 2

Step 1

4-Fluoro-nitrobenzene and 4-hydroxyindole were reacted together in DMA in the presence of potassium tert-butoxide in the manner described for Example 7 step 1 to give, after chromatographic purification, intermediate 1.

Mass Spectrum m/e 255 (M$^+$+H)

Step 2

Intermediate 1 was reduced to the corresponding aniline by reduction, at room temperature in ethyl acetate solution, with hydrogen and catalytic 5% Pd/C to give intermediate 2.

Mass Spectrum m/e 225 (M$^+$+H)

67

Step 3

Intermediate 2 was reacted with intermediate 3 (as described in WO 9843960) in n-propanol solution at 110° C. for 18 hr to give compound 11.

Mass Spectrum m/e 437 (M$^+$+H)

NMR Spectrum (d-6-DMSO, δ values) 4.00 (s, 6H), 6.20 (t, 1H), 6.60 (d, 1H), 7.00 (d, 1H), 7.05 (d, 2H), 7.25 (m, 2H), 7.40 (d, 2H), 7.50 (s, 1H), 8.20 (s, 1H), 8.90 (s, 1H), 11.20 (br s, 1H), 11.30 (br s, 1H).

Example 12

Preparation of Compound No 12 in Table 3

68

Step 4

Intermediate 3 was reacted with Intermediate D, prepared as described above, in n-propanol solution at 105° C. for 3 hrs to give compound 12.

Mass Spectrum m/e 495.5 (M+H)$^+$.

NMR Spectrum (d-6-DMSO, δ values) 2.89 (d, 3H), 3.99 (s, 6H), 6.99 (d, 1H), 7.21-7.30 (m, 3H), 7.45-7.55 (m, 4H), 7.58 (s, 1H), 8.16 (s, 1H), 8.47 (d, 1H), 8.94 (s, 1H).

Example 13

Preparation of Compound No 13 in Table 3

This was prepared by a similar route to that described for example 12 starting with intermediate 1 of example 12.

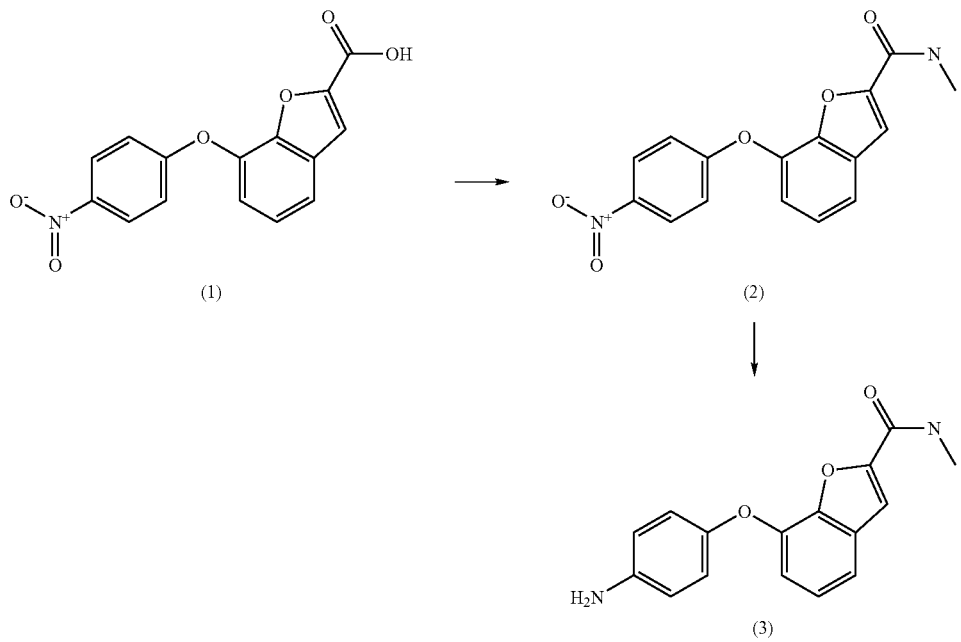

Step 1

4-Fluoro-nitrobenzene was reacted with 2-carboxy-7-hydroxy-benzofuran in DMA in the presence of potassium butoxide at 120° C. for 2 hrs to give intermediate 1.

Mass Spectrum m/e 254.1 (M-CO$_2$H)$^-$.

Step 2

Intermediate 1 was then reacted with methylamine in the presence of DMAP/HCl/EDC/DCM at room temperature for 18 hrs to give intermediate 2.

Mass Spectrum m/e Mass ion not observed (M+H)$^+$.

NMR Spectrum (d-6-DMSO, δ values) 2.74 (d, 3H), 7.17 (d, 2H), 7.27 (d, 1H), 7.37 (t, 1H), 7.59 (s, 1H), 7.69 (d, 1H), 8.22 (d, 2H), 8.54 (d, 1H).

Step 3

Intermediate 2 was reduced to the corresponding aniline by reduction at room temperature in ethyl acetate solution, with hydrogen and catalytic 5% Pd/C for 4 hrs to give intermediate 3.

Mass Spectrum m/e 283.4 (M+H)$^+$.

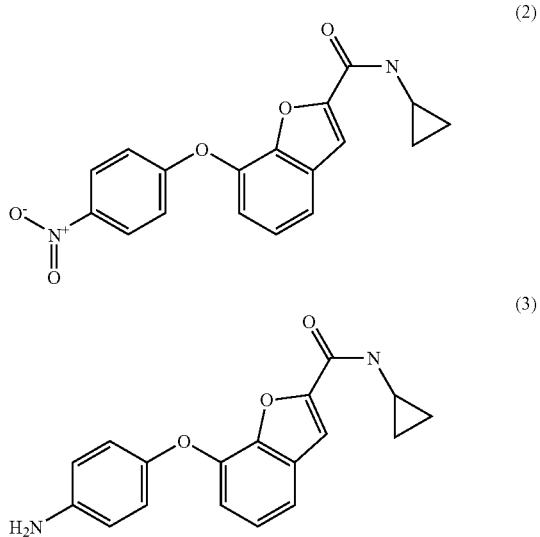

Step 1

Intermediate 1 was reacted with methylamine in the presence of DMAP/HCl/EDC/DCM at room temperature for 18 hrs to give intermediate 2.

Mass Spectrum m/e Mass ion not observed (M+H)+.

NMR Spectrum (d-6-DMSO, δ values) 0.58 (m, 2H), 0.68 (m, 2"), 2.79 (m, 1H), 7.19 (m, 2H), 7.26 (d, 1H), 7.38 (t, 1H), 7.61 (s, 1H), 7.69 (d, 1H), 8.25 (m, 2M), 8.66 (d, 1H).

Step 2

Intermediate 2 was reduced to the corresponding aniline by reduction at room temperature in ethyl acetate solution, with hydrogen and catalytic 5% Pd/C for 4 hrs to give intermediate 3.

Mass Spectrum m/e 309.4 (M+H)+.

Step 4

Intermediate 3 was reacted with Intermediate D, prepared as described above in n-propanol solution at 105° C. for 3 hrs to give compound 13.

Mass Spectrum m/e 521.5 (M+H)+.

NMR Spectrum (d-6-DMSO, δ values) 0.64 (m, 2H), 0.70 (m, 2H), 2.85 (m, 1H), 4.00 (s, 6H), 6.95 (d, 1H), 7.00-7.09 (m, 3H), 7.48-7.55 (m, 4H), 7.60 (s, 1H), 8.16 (s, 1H), 8.64 (d, 1H), 8.92 (s, 1H).

Example 14

Preparation of Compound No 14 in Table 4

Step 1

4-Fluoro-nitrobenzene was reacted with 2-carboxy-8-hydroxy-quinoline in DMA in the presence of potassium tert-butoxide at 120° C. for 2 hrs to give intermediate 1.

Mass Spectrum m/e 311.2 (M+H)+.

Step 2

Intermediate 1 was converted to intermediate 2 by reaction with isopropylamine in the presence of DMAP/EDC/DCM for 18 hrs at room temperature.

Mass Spectrum m/e 352.3 (M+H)+.

Step 3

Intermediate 2 was reduced to the corresponding aniline by reduction at room temperature in ethyl acetate solution, with hydrogen and catalytic 5% Pd/C for 18 hrs.

Mass Spectrum m/e 322.4 (M+H)+.

Step 4

Intermediate 3 was reacted with Intermediate D, prepared as described above, in n-propanol solution at 105° C. for 3 hrs to give compound 14.

Mass Spectrum m/e 534.4 (M+H)+.

NMR Spectrum (d-6-DMSO, δ values) 1.19 (d, 6H), 4.04 (m, 1H), 7.20 (d, 2H), 7.43-7.50 (m, 3H), 7.53 (d, 1H), 7.69 (t, 1H), 7.85 (d, 1H), 7.91 (d, 1H), 8.10-8.17 (m, 2H), 8.60 (d, 1H), 8.91 (s, 1H).

Example 15

Preparation of Compound No 15 in Table 4

This was prepared by a similar route to that described for example 14 starting with intermediate 1 of example 14.

Step 1

Intermediate 1 was converted to intermediate 2 by reaction with cyclopropylamine in the presence of DMAP/EDC/DCM for 18 hrs at room temperature.

Mass Spectrum m/e 350.3 (M+H)⁺.

Step 2

Intermediate 2 was reduced to the corresponding aniline by reduction at room temperature in ethyl acetate solution, with hydrogen and catalytic 5% Pd/C for 3 hrs.

Mass Spectrum m/e 320.3 (M+H)⁺.

Step 3

Intermediate 3 was reacted with Intermediate D, prepared as described above, in n-propanol solution at 105° C. for 3 hrs Mass Spectrum m/e 532.3 (M+H)⁺.

NMR Spectrum (d-6-DMSO, δ values) 0.62 (m, 2H), 0.74 (m, 2H), 2.86 (m, 1H), 3.97 (s, 6H), 7.19 (d, 2H), 7.41-7.50 (m, 4H), 7.66 (t, 1H), 7.87 (d, 1H), 8.06 (d, 1H), 8.11-8.16 (m, 2H), 8.60 (d, 1H), 8.90 (s, 1H).

Example 15A

Preparation of Compound No 15 A in Table 5

This was prepared by reacting Intermediates D and F, described above, in n-propanol solution at 105° C. for 3 hrs.

Mass Spectrum m/e 539.3 (M+H)⁺.

NMR Spectrum (d-6-DMSO, δ values) 0.47 (m, 2H), 0.62 (m, 2H), 1.38 (s, 6H), 2.70 (m, 1H), 4.02 (s, 6H), 6.95-7.22 (m, 6H), 7.47 (s, 1H), 7.50 (s, 2H), 7.94 (d, 1H), 8.17 (s, 1H), 8.94 (s, 1H), 11.07 (bs, 1H).

Example 16

Preparation of Compound No 16 in Table 5

Step 1

This was prepared by reacting Intermediate A with Intermediate F in n-propanol solution at 105° C. for 3.5 hr to form Intermediate 1

Mass Spectrum m/e 601.3 (M+H)⁺

Step 2

Intermediate 1 was then reacted with morpholine in sodium iodide at room temperature for 5 days. The product was purified by chromatography.

Mass Spectrum m/e 652.6 (M+H)⁺

NMR Spectrum (d-6-DMSO d-4-Acetic, δ values) 0.46 (m, 2H), 0.61 (m, 2H), 1.36 (s, 6H), 2.36 (m, 2H), 2.71 (m, 1H), 3.15 (m, 2H), 3.33 (m, 2H), 3.52 (m, 2H), 3.84 (m, 2H), 3.93-4.05 (m, 5H), 4.34 (t, 2H), 6.97-7.22 (m, 6H), 7.47 (d, 2H), 7.53 (s, 1H), 7.91 (d, 1H), 8.19 (s, 1H), 8.94 (s, 1H).

Example 17

Preparation of Compound No 17 in Table 5

Step 1

Intermediate (2), example 43 was reacted with 3-(morpholino)propylamine in the presence of DMAP/EDC/DCM for 18 hrs at room temperature to produce Intermediate 1. The product was purified by chromatography.

Mass Spectrum m/e 444.4 (M+H)⁺.

Step 2

Intermediate 1 was then converted to the corresponding aniline by reduction at room temperature in ethyl acetate solution with hydrogen and catalytic 5% Pd/C.

Mass Spectrum m/e 414.4 (M+H)$^+$.

Step 3

The aniline derivative was then reacted with Intermediate D in n-propanol solution in the presence of 1.0M Ethereal HCl at a temperature of 105° C. for 3 hrs.

Mass Spectrum m/e 626.3 (M+H)$^+$.

NMR Spectrum (d-6-DMSO d-4-Acetic, δ values) 1.34 (s, 6H), 1.85 (m, 2H), 2.98 (m, 4H), 3.16 (m, 2H), 3.31 (m, 2H), 3.76 (m, 2H), 3.88-3.97 (m, 2H), 3.99 (s, 3H), 4.00 (s, 3H), 6.96-7.02 (m, 3H), 7.04-7.20 (m, 3H), 7.40-7.48 (m, 3H), 8.04 (t, 1H), 8.18 (s, 1H), 8.92 (s, 1H).

Example 18

Preparation of Compound No 18 in Table 5

Step 1

This was prepared by an analogous route to that described for example 17 except that 3-(morpholino)propylamine was replaced by 2-(2-oxoimidazolidin-1-yl)ethylamine to produce Intermediate 1, shown above. The product was purified by chromatography.

Mass Spectrum m/e 429.4 (M+H)$^+$.

Step 2

The aniline corresponding to intermediate 1 was prepared as described in example 17.

Mass Spectrum m/e 399.4 (M+H)$^+$.

Step 3

The aniline derivative was converted to compound 18 by reaction with Intermediate D as described in example 17.

Mass Spectrum m/e 611.5 (M+H)$^+$.

NMR Spectrum (d-6-DMSO d-4-Acetic, δ values) 1.31 (s, 6H), 3.07-3.23 (m, 6H), 3.26-3.34 (m, 2H), 3.96 (s, 3H), 3.98 (s, 3H), 6.97-7.18 (m, 6H), 7.40 (4, 2H), 7.45 (s, 1H), 7.84 (t, 1H), 8.08 (s, 1H), 8.94 (s, 1H).

Example 19

Preparation of Compound No 19 in Table 5

Step 1

This was prepared by an analogous route to that described for example 18 except that 3-(morpholino)propylamine was replaced by 3-(morpholino)ethylamine to produce Intermediate 1, shown above. The product was purified by chromatography.

Mass Spectrum m/e 430.4 (M+H)$^+$.

Step 2

The aniline derivative corresponding to intermediate 1 was prepared as described in example 17. Mass Spectrum m/e 400.4 (M+H)$^+$.

Step 3

The aniline derivative of step 2 was converted to compound 19 by reaction with Intermediate D as described in example 17.

Mass Spectrum m/e 612.4 (M+H)$^+$.

NMR Spectrum (d-6-DMSO δ-4-Acetic, δ values) 1.36 (s, 6H), 3.07 (m, 2H), 3.15 (m, 2H), 3.39 (m, 2H), 3.51 (m, 2H), 3.74 (m, 2H), 3.90 (m, 2H), 3.99 (s, 6H), 6.96-7.03 (m, 3H), 7.09-7.19 (m, 3H), 7.42 (s, 2H), 7.46 (s, 1H), 8.16 (s, 1H), 8.20 (t, 1H), 8.92 (s, 1H).

Example 20

Preparation of Compound No 20 in Table 5

Step 1

This was prepared by an analogous route to that described for example 18 except that 3-(morpholino)propylamine was replaced by 3-(imidazol-1-yl)propylamine to produce Intermediate 1, shown above. The product was purified by chromatography.

Mass Spectrum m/e 425.4 (M+H)+.

Step 2

The aniline derivative corresponding to intermediate 1 was prepared as described in example 17. Mass Spectrum m/e 395.4 (M+H)+.

Step 3

The aniline derivative of step 2 was converted to compound 20 by reaction with Intermediate D as described in example 17. The product was purified by chromatography: yes Mass Spectrum m/e 607.5 (M+H)+.

NMR Spectrum (d-6-DMSO d-4-Acetic, δ values) 1.36 (s, 6H), 1.90 (m, 2H), 3.08 (m, 2H), 3.91 (s, 3H), 3.92 (s, 3H), 4.02 (t, 2H), 6.90-7.14 (m, 6H), 7.26-7.30 (m, 3H), 7.35 (s, 1H), 7.50 (s, 1H), 7.78 (s, 1H), 8.03 (t, 1H), 8.36 (s, 1H), 8.50 (s, 1H).

Example 21

Preparation of Compound No 21 in Table 5

Step 1

This was prepared by an analogous route to that described for example 18 except that 3-(morpholino)propylamine was replaced by 3-(pyrrolid-1-y)propylamine) to produce Intermediate 1, shown above. The product was purified by chromatography. Mass Spectrum m/e 428.5 (M+H)+.

Step 2

The aniline derivative corresponding to intermediate 1 was prepared as described in example 17. Mass Spectrum m/e 394.4 (M+H)+.

Step 3

The aniline derivative of step 2 was converted to compound 21 by reaction with Intermediate D as described in example 17. The product was purified by chromatography.

Mass Spectrum m/e 610.2 (M+H)+.

NMR Spectrum (d-6-DMSO d-4-Acetic, δ values) 1.36 (s, 6H), 1.74-1.99 (m, 6H), 2.89 (m, 2H), 3.00 (m, 2H), 3.16 (m, 2H), 3.46 (m, 2H), 3.98 (s, 6H), 6.94-7.01 (m, 3H), 7.04-7.20 (m, 3H), 7.42 (s, 2H), 7.46 (s, 1H), 8.03 (t, 1H), 8.16 (s, 1H), 8.94 (s, 1H).

Example 22

Preparation of Compound No 22 in Table 5

Step 1

Intermediate 3, example 43, was converted to the corresponding aniline derivative (intermediate (1)) above by reduction at room temperature for 18 hrs in ethyl acetate solution with hydrogen and catalytic 5% Pd/C Mass Spectrum m/e 373.4 (M+H)+.

Step 2

Intermediate 1 was then reacted with cyclopropylamine in methanol at room temperature for 18 hrs to give intermediate 2.

Mass Spectrum m/e 384.4 (M+H)+.

Step 3

Intermediate 2 was the reacted with Intermediate D, described above, in n-propanol in n-propanol solution for 3 hr at 105° C. to give compound 22.

Mass Spectrum m/e 5944 (M+H)+.

NMR Spectrum (d-6-DMSO, δ values) 0.39 (m, 2H), 0.42 (m, 2H), 1.36 (s, 6H), 2.63 (m, 1H), 3.69 (d, 2H), 4.01 (s, 6H), 7.05 (d, 2H), 7.10-7.22 (m, 4H), 7.30 (d, 1H), 7.43 (s, 1H), 7.47 (s, 2H), 7.93 (d, 1H), 8.00 (t, 1H), 8.15 (s, 1 μl), 8.94 (s, 1H).

Example 23

Preparation of Compound No 23 in Table 5

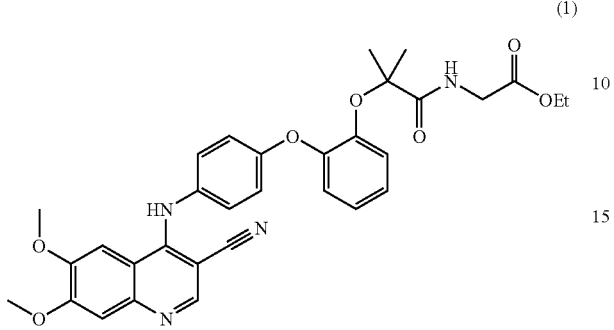

(1)

Step 1

Intermediate 3, example 43, was reacted with Intermediate D, described above, in n-propanol solution for 4 hr at 105° C. to produce intermediate 1 in the above scheme.

Mass Spectrum m/e 585.4 (M+H)⁺.

Step 2

Intermediate 1 was then reacted with cyclopropylamine in ethanol at room temperature for 18 hr to give compound 23.

Mass Spectrum m/e 610.2 (M+H)⁺.

NMR Spectrum (d-6-DMSO, δ values) 0.17 (m, 2H), 0.41 (m, 2H), 0.86 (m, 1H), 1.37 (s, 6H), 2.98 (t, 2H), 3.73 (d, 2H), 4.01 (s, 6H), 7.02-7.08 (d, 2H), 7.10-7.20 (m, 3H), 7.27 (d, 1H), 7.42-7.48 (m, 3H), 7.87 (t, 1H), 8.04 (t, 1H), 8.13 (s, 1H), 8.93 (s, 1H).

Example 24

Preparation of Compound No 24 in Table 5

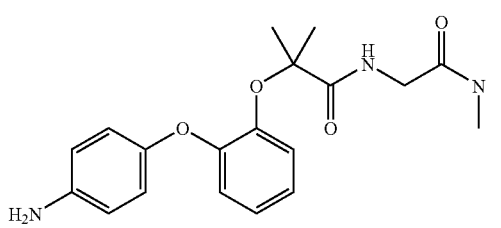

(1)

Intermediate 1, example 22, was reacted with methylamine in ethanol at room temperature for 18 hr to give intermediate (1) in the above scheme.

Mass Spectrum m/e 358.4 (M+H)⁺.

Step 2

Intermediate 2 was reacted with Intermediate D, described above, in n propanol solution in 1.0M Ethereal HCl at 105° C. for 3 hrs.

Mass Spectrum m/e 570.20 (M+H)⁺.

NMR Spectrum (d-6-DMSO, δ values) 1.34 (s, 6H), 2.58 (d, 3H), 3.69 (d, 2H), 3.99 (s, 6H), 7.01 (d, 2H), 7.07-7.17 (m, 3H), 7.24 (d, 1H), 7.41 (s, 1H), 7.46 (d, 2H), 7.71 (d, 1H), 8.00 (t, 1H), 8.15 (s, 1H), 8.92 (s, 1H).

Example 25

Preparation of Compound No 25 in Table 5

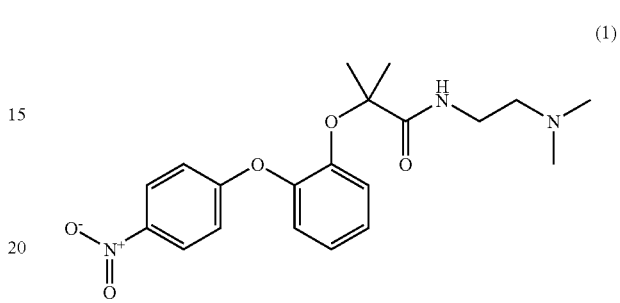

(1)

Step 1

Intermediate 2, example 43, was reacted with oxalyl chloride in DMF/DMC for 16 hr at 0° C. followed by reaction with dimethylaminoethylamine in the presence of triethylamine/DCM at room temperature for 16 hr to give intermediate (1) in the above scheme. The product was purified by chromatography.

Mass Spectrum m/e 388.4 (M+H)⁺.

Step 2

Intermediate (1) was converted to the corresponding aniline by reduction at room temperature for 18 hrs in ethyl acetate solution with hydrogen and catalytic 10% Pd/C.

Mass Spectrum m/e 358.5 (M+H)⁺.

Step 3

The product of step 2 was reacted with Intermediate D, described above, in n-propanol solution in 2.0M Ethereal HCl at 105° C. for 3 hr.

Mass Spectrum m/e 570.5 (M+H)⁺.

NMR Spectrum (d-6-DMSO d-4-Acetic, δ values) 1.36 (s, 6H), 2.72 (m, 6H), 3.10 (m, 2H), 3.47 (m, 2H), 3.98 (s, 3H), 3.99 (s, 3H), 6.92-7.19 (m, 6H), 7.38-7.48 (m, 3H), 8.13 (m, 2H), 8.89 (s, 1H).

Example 26

Preparation of Compound No 26 in Table 5

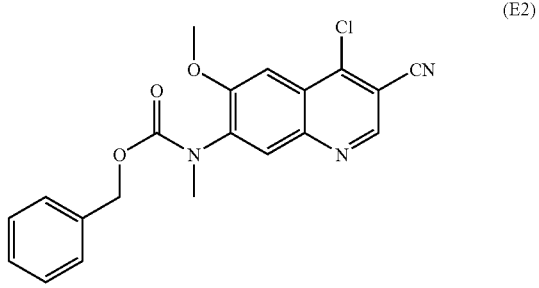

(E2)

-continued

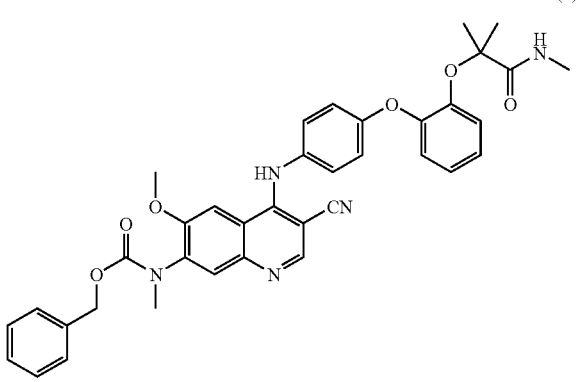

(2)

Intermediate (2) above was reacted with 33% HBr in acetic acid for 2 hrs to give compound 26.

Mass Spectrum m/e 512.3 (M+H)$^+$

NMR Spectrum (d-6-DMSO, $CD_3CO_2D$, δ values) 1.32 (s, 6H), 2.60 (s, 3H), 2.86 (s, 3H), 3.99 (s, 3H), 6.65 (s, 1H), 6.97 (d, 3H), 7.09 (m, 3H), 7.40 (d, 2H), 7.81 (s, 1H), 8.83 (s, 1H)

Intermediate 2 was prepared by reacting intermediate E2 above with Intermediate D, previously described, in iso-propanol at 100° C. for 3.5 hr.

Mass Spectrum m/e 646.1 (M+H)$^+$

Intermediate E2 was prepared as outlined in the following reaction scheme.

Step 1

Intermediate (A2) was prepared by reacting benzylchloroformate with 2-methoxy-5-nitroaniline in pyridine at room temperature for 11 hr.

NMR Spectrum (d-6-DMSO, δ values) 3.93 (s, 3H), 5.18 (s, 2H), 7.21 (d, 1H), 7.37 (m, 5H), 7.98 (m, 1H), 8.69 (m, 1H), 9.10 (s, 1H).

Step 2

Intermediate A2 was reacted in $SnCl_2.2H_2O$ in ethyl acetate at 105° C. for 5 hrs and then with ethoxyethylcyanoacetate in ethanol at 90° C. for 90 mins to give intermediate B(2).

NMR Spectrum (d-6-DMSO, δ values)(~3:1 mixture of isomers) 1.22 (m, 3H), 3.76 (s, 3H), 4.16 (m, 2H), 5.13 (s, 2H), 7.02 (m, 2H), 7.35 (m, 5H), 7.72 (m, 0.25H), 7.80 (m, 0.75H), 8.14 (bs, 0.75H), 8.26 (d, 0.25H), 8.66 (s, 0.25H), 8.71 (s, 0.75H), 10.65 (d, 0.25H), 10.78 (bs, 0.75H).

Step 3

Intermediate (B2) was reacted at 250-260° C. for 4 hrs with Dowtherm A to give Intermediate (C2).

Mass Spectrum m/e 350 (M+H)$^+$.

Step 4

Intermediate (C2) was reacted at 110° C. for 2 hrs with methylcyanide in the presence of $POCl_3$. to give Intermediate (D2). The product was purified by chromatography.

Mass Spectrum m/e 368, 370 (M+H)$^+$.

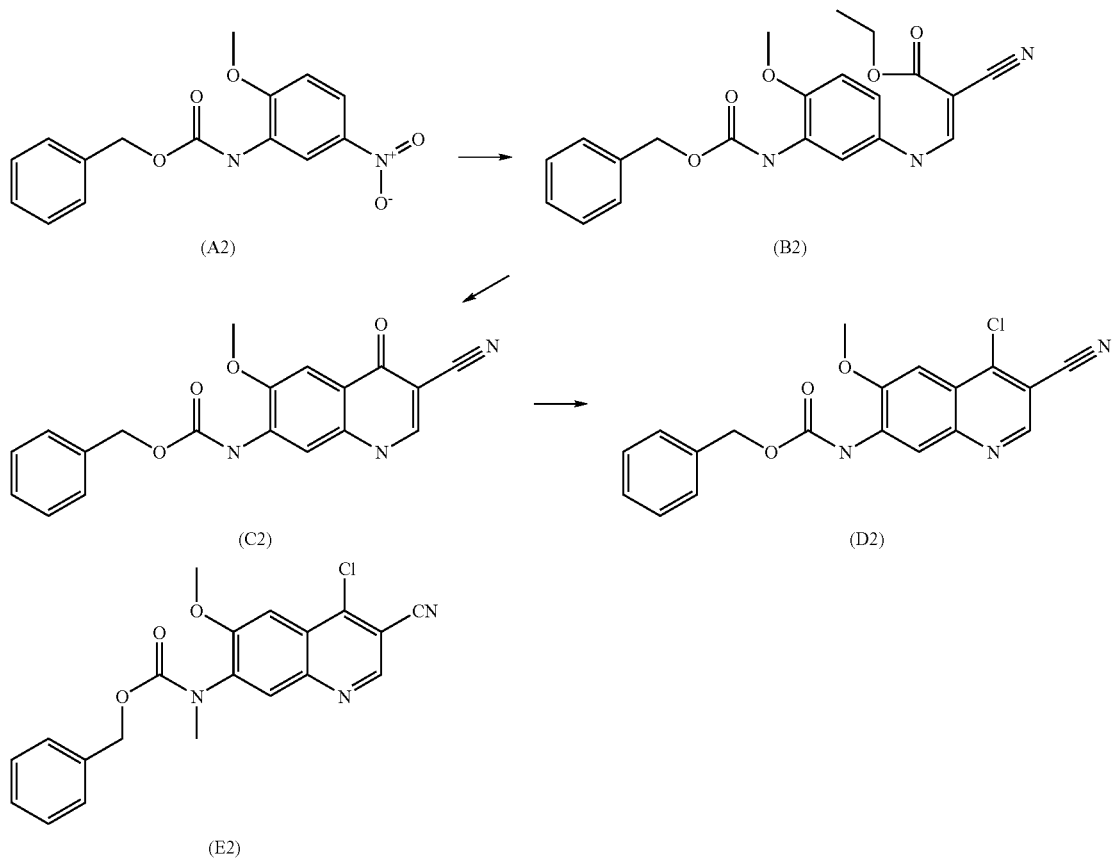

Step 5

Intermediate (D2) was converted to intermediate E2 by reaction with KHMDS/MeI/18-Crown-6/DMA at a temperature within the range 0-25° C. for 3 hrs. The product was purified by chromatography.

Mass Spectrum m/e 382.2 (M+H)+

Example 27

Preparation of Compound No. 27 in Table 5

(1)

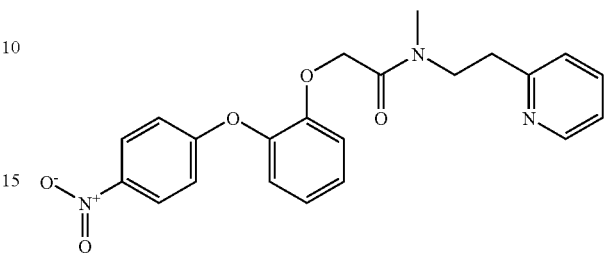

Step 1

Intermediate 2, example 43 was reacted with 2-(pyrid-2-yl)-ethylamine in the presence of DMAP/EDC/DCM at room temperature for 16 hrs. The product was purified by chromatography to produce intermediate (1) in the scheme above.

Mass Spectrum m/e 422.38 (M+H)+.

Step 2

Intermediate (1) was then converted to the corresponding aniline by reduction at room temperature in ethyl acetate solution with hydrogen and catalytic 10% Pd on C at room temperature for 18 hr.

Mass Spectrum m/e 392.5 (M+H)+.

Step 3

The product of step 2 was then reacted with Intermediate D described above in n-propanol solution in the presence of 2.0M Ethereal HCl 105° C. for 3 hr. The product was purified by chromatography.

Mass Spectrum m/e 604.4 (M+H)+.

NMR Spectrum (d-6-DMSO, δ values) 1.26 (s, 6H), 3.14 (m, 2H), 3.57 (m, 2H), 3.98 (s, 3H), 3.99 (s, 3H), 6.88 (d, 1H), 6.96 (d, 2H), 7.05-7.14 (m, 3H), 7.43 (d, 2H), 7.49 (s, 1H), 7.68-7.77 (m, 2H) 8.07 (t, 1H), 8.23 (s, 1H) 8.27 (t, 1H) 8.71 (d, 1H), 8.92 (s, 1H), 11.26 (bs, 1H).

Example 28

Preparation of Compound No. 28 in Table 5

(1)

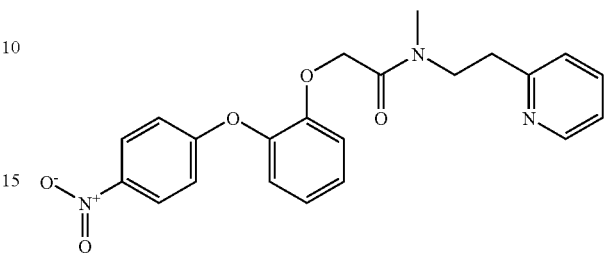

Step 1

Intermediate 2, example 43 was reacted with N-[2-(pyrid-2-yl)ethyl]N-(methyl)amine in the presence of DMAP/EDC/DCM at room temperature for 24 hrs. The product was purified by chromatography to produce intermediate (1) in the scheme above.

Mass Spectrum m/e 408.3 (M+H)+.

Step 2

Intermediate (1) was then converted to the corresponding aniline by the same method as described in example 27.

Mass Spectrum m/e 378.3 (M+H)+.

Step 3

The product of step 2 was then reacted with Intermediate D as described in example 27 except the product was not purified by chromatography.

Mass Spectrum m/e 590.6 (M+H)+.

NMR Spectrum (d-6-DMSO, δ values) 2.83+2.97 (2s, 3H), 3.16+3.24 (2t, 2H), 3.69 (t, 2H), 3.99 (s, 6H), 4.77+4.80 (2s, 2H), 6.80-6.88 (m, 1H), 6.92-7.03 (m, 4H), 7.11 (t, 1H), 7.39 (d, 2H), 7.47 (s, 1H), 7.72-7.82 (m, 2H) 8.20 (d, 1H), 8.30 (t, 1H) 8.70 (d, 1H), 8.94 (s, 1H), 11.24 (bs, 1H).

Example 29

Preparation of Compound No. 29 in Table 5

(1)

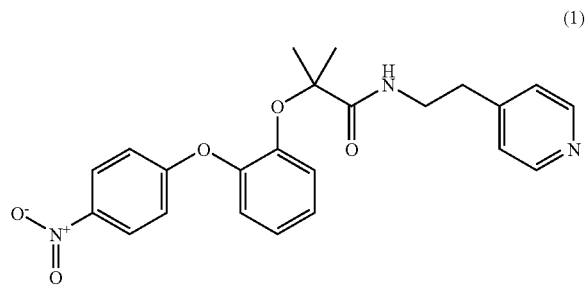

83

Step 1

Intermediate 2, example 43 was reacted with 2-(pyrid-4-yl)-ethylamine in the presence of HOBT/N-Methyl morpholine/EDC/DMA at room temperature for 16 hrs to produce intermediate (1) in the scheme above.

Mass Spectrum m/e 422.32 (M+H)+.

Step 2

Intermediate (1) was then converted to the corresponding aniline by the method described in example 27

Mass Spectrum m/e 392.4 (M+H)+.

Step 3

The product of step 2 was then reacted with Intermediate D described by the method described in example 27. The product was purified by chromatography.

Mass Spectrum m/e 604.0 (M+H)+.

NMR Spectrum (d-6-DMSO, δ values) 1.29 (s, 6H), 3.05 (m, 2H), 3.52 (m, 2H), 3.99 (s, 3H), 4.00 (s, 3H), 6.86 (m, 1H), 6.97 (d, 2H), 7.04-7.11 (m, 3H), 7.43 (d, 2H), 7.51 (s, 1H), 7.80 (d, 2H) 8.07 (t, 1H), 8.27 (s, 1H), 8.74 (d, 2H), 8.93 (s, 1H), 11.30 (bs, 1H).

Example 30

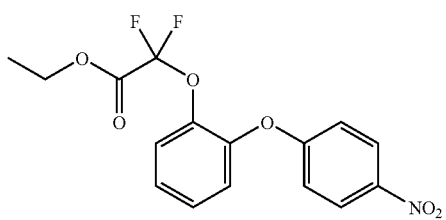

(1)

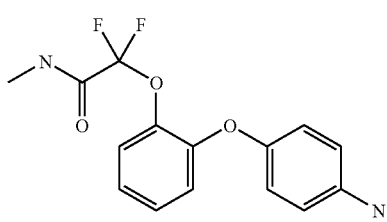

(2)

Step 1

Intermediate B was reacted with ethyl bromodifluoroacetate and potassium-t-butoxide in the presence of DMA at room temperature for 16 hrs to give intermediate (1).

Mass Spectrum m/e 354.12 (M++H).

84

Step 2

Intermediate (1) was then converted to the corresponding aniline by reduction for 2 hrs in ethyl acetate solution with hydrogen and catalytic 10% Pd on C Mass Spectrum m/e 324.2 (M++H).

Step 3

The product of step 2 was then reacted with methylamine in the presence of methanol and ethanol at room temperature for 48 hrs to give intermediate (2) in the above scheme.

Mass Spectrum m/e 308.29 (M++H).

Step 4

Intermediate (2) was then reacted with Intermediate D, prepared as described above, in n-propanol solution at a temperature of 100° C. for 2 hr to give compound 30.

Mass Spectrum m/e 521.07 (M++H).

NMR Spectrum (d-6-DMSO, δ values) 2.67 (m, 3H), 3.98 (s, 6H), 7.02 (d, 1H), 7.12 (d, 2H), 7.2 (t, 1H), 7.28 (t, 1H), 7.4 (d, 1H), 7.46 (d, 2H), 7.5 (s, 1H), 8.13 (s, 1H), 8.84 (br.s, 1H), 8.86 (s, 1H), 11.1 (br.s, 1H).

Example 31

Preparation of Compound 31 in Table 5

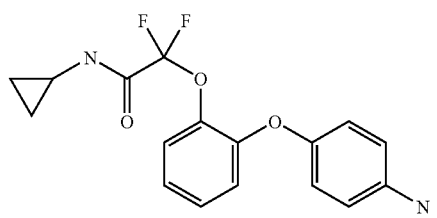

(1)

Step 1

Steps 1-2 of example 30 were followed to give the aniline derivative.

Step 2

The aniline derivative was then reacted with cyclopropylamine in the presence of methanol and ethanol for 48 hrs at room temperature to give intermediate (1) above.

Mass Spectrum m/e 334.3 (M++H).

Step 3

Intermediate (1) was then reacted with Intermediate D, prepared as described above, in n-propanol solution at a temperature of 100° C. for 2 hr to give compound 31.

Mass Spectrum m/e 547.09 (M++H).

NMR Spectrum (d-6-DMSO, δ values) 0.55 (m, 2H), 0.67 (m, 2H), 2.72 (m, 1H), 3.96 (s, 6H), 7.02 (2d, 1H), 7.14 (d, 2H), 7.2 (t, 1H), 7.29 (t, 1H), 7.38 (d, 1H), 7.46 (d, 2H), 7.51 (s, 1H), 8.11 (s, 1H), 8.91 (s, 1H), 9.03 (br.d, 1H), 11.04 (v.br.s, 1H).

Example 32

Preparation of Compound No. 32 in Table 5

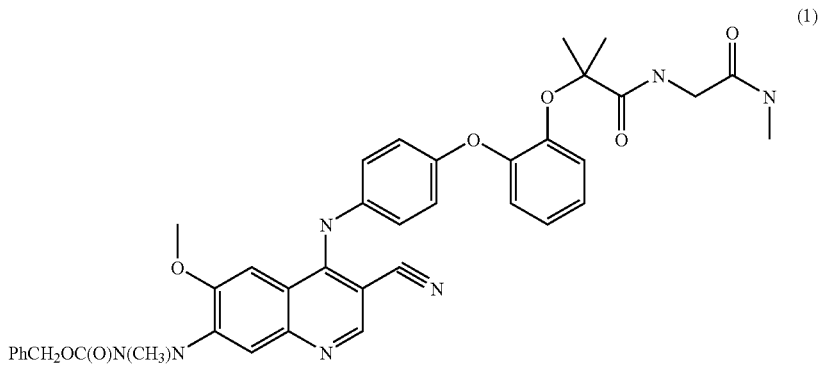

Step 1

Intermediate E2, example 26 was reacted with Intermediate (I), example 24 in n-propanol solution at a temperature 105° C. for 5 hr.

Mass Spectrum m/e 703.3 (M+H)⁺

Step 2

Intermediate (1) above was converted to compound 32 by reaction with thioanisole in 33% HBr at room temperature for 2 hr. The product was purified by chromatography.

Mass Spectrum m/e 569.19 (M+H)⁺

NMR Spectrum (d-6-DMSO+d-4-acetic acid, δ values) 2.56 (s, 6H), 2.84 (s, 3H), 3.68 (s, 3H), 3.95 (s, 3H), 6.68 (s, 1H), 6.95-6.98 (m, 3H), 7.06-7.12 (m, 4H), 7.19-7.22 (d, 1H), 7.29-7.32 (d, 2H), 7.73 (s, 1H), 8.55 (s, 1H)

Example 33

Preparation of Compound 33 in Table 5

Step 1

Intermediate E2, example 26 was reacted with intermediate 2, example 22 in n-propanol solution at a temperature 100° C. for 1.5 hr to give intermediate (1) above.

Mass Spectrum m/e 729.4 (M+H)⁺

Step 2

Intermediate (1) was reacted 33% HBr in acetic acid for 2 hr to give compound 33.

Mass Spectrum m/e 595.2 (M+H)⁺

NMR Spectrum (d-6-DMSO, δ values) 0.04 (m, 2H), 0.27 (m, 2H), 1.00 (s, 6H), 2.53 (s, 3H), 3.31 (d, 2H), 3.66 (s, 3H),

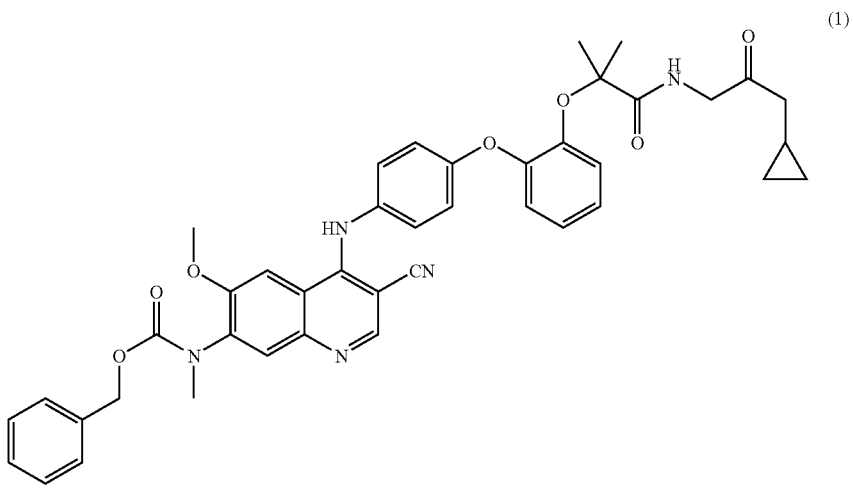

6.32 (s, 1H), 6.67 (d, 2H), 6.80 (m, 5H), 7.07 (d, 2H), 7.48 (s, 1H), 7.55 (m, 1H), 7.64 (m, 1H), 8.50 (s, 1H), 10.23 (s, 1H)

Example 34

Preparation of compound 34 in Table 5

(1)

Step 1

Intermediate 2, example 43 was reacted with 2-(pyrrolidin-1-yl)ethylamine in the presence of HOBT/N-Methyl morpholine/EDC/DMA at room temperature for 16 hr to give intermediate (1) above.

Mass Spectrum m/e 414.4 (M+H)$^+$.

Step 2

Intermediate (1) was reduced to the corresponding aniline by reduction in ethyl acetate solution in the presence of hydrogen and catalytic 10% Pd on C at room temperature for 6 hr.

Mass Spectrum m/e 384.4 (M+H)$^+$.

Step 3

The product of step 2 was reacted with intermediate D, prepared as described above, in n-propanol solution in 1.0M Ethereal HCl at a temperature of 105° C. for 3 hr.

Mass Spectrum m/e 596.3 (M+H)$^+$.

NMR Spectrum (d-6-DMSO d-4-Acetic, δ values) 1.36 (s, 6H), 1.88-2.00 (m, 4H), 2.95 (m, 2H), 3.18 (m, 2H), 3.40-3.58 (m, 4H), 3.98 (s, 3H), 3.99 (s, 3H), 6.96-7.04 (m, 3H), 7.09-7.20 (m, 3H), 7.43 (s, 1H), 7.46 (s, 2H), 8.20 (m, 2H), 8.93 (s, 1H).

Example 35

Preparation of Compound 35 in Table 5

(1)

Step 1

Intermediate (4), example 43 was reacted with N,N-dimethylethylene diamine in the presence of HOBt/EDC/DCM at room temperature for 16 hr to give intermediate (1) above. The product was purified by chromatography.

Mass Spectrum m/e 461.3 (M$^+$+NH4).

Step 2

Intermediate (1) was reduced to the corresponding aniline by reduction in ethyl acetate solution in the presence of hydrogen and catalytic Pd on C at room temperature for 3 hr.

Mass Spectrum m/e 415.4 (M$^+$+H).

Step 3

The product of step 2 was reacted with intermediate D, as described above, in n-propanol solution in Ethereal HCl at a temperature of 105° C. for 2 hr.

Mass Spectrum m/e 625.5 (M$^-$–H).

NMR Spectrum (d-6-DMSO, δ values) 1.33 (s, 6H), 2.75 (s, 6H), 3.10 (t, 2H), 3.42 (t, 2H), 3.75 (s, 2H), 3.96 (s, 6H), 7.00 (d, 2H), 7.05-7.18 (m, 3H), 7.24 (d, 1H), 7.41 (m, 3H), 8.05 (m, 1H), 8.10-8.20 (m, 2H), 8.89 (s, 1H).

Example 36

Preparation of Compound 36 in Table 5

(1)

Step 1

Intermediate (2), example 43 was reacted with 2-(ethylamino)ethylamine in the presence of HOBt/EDC/N-methyl morpholine/DCM at room temperature for 16 hr to give intermediate (1) above. The product was purified by chromatography.

Mass Spectrum m/e 388.4 (M+H)$^+$.

Step 2

Intermediate (1) was reduced to the corresponding aniline by reduction in ethyl acetate solution in the presence of ethanol, hydrogen and catalytic 10% Pd on C at room temperature for 6 hr. Mass Spectrum m/e 358.3 (M+H)$^+$.

Step 3

The product of step 2 was reacted with intermediate D, as described above, in n-propanol solution in 1.0M Ethereal HCl at a temperature of 105° C. for 3 hr.

Mass Spectrum m/e 568.7 (M+H)$^+$.

NMR Spectrum (d-6-DMSO, δ values) 1.15 (t, 3H), 1.37 (s, 6H), 2.93 (m, 4H), 3.40 (q, 2H), 3.98 (s, 3H), 3.99 (s, 3H), 6.95-7.04 (m, 3H), 7.09-7.20 (m, 3H), 7.40 (s, 1H), 7.45 (d, 2H), 8.10 (t, 1H), 8.42 (s, 1H), 8.81 (bs, 1H), 8.90 (s, 1H).

Example 37

Preparation of Compound 37 in Table 5

The aniline derivative of step 2, example 47 was reacted with Intermediate D, prepared as described above, in n-propanol solution at a temperature of 105° C. for 2 hr to give compound 37.

Mass Spectrum m/e 584.2 (M+ +H).

NMR Spectrum (d-6-DMSO, δ values) 0.99 (t, 3H), 1.34 (s, 6H), 3.07 (m, 2H), 3.69 (d, 2H), 3.98 (s, 6H), 7.00 (d, 2H), 7.05-7.18 (m, 3H), 7.22 (d, 1H), 7.40-7.46 (m, 3H), 7.76 (t, 1H), 7.99 (t, 1H), 8.14 (s, 1H), 8.91 (s, 1H)

Example 38

Preparation of Compound 38 in Table 5

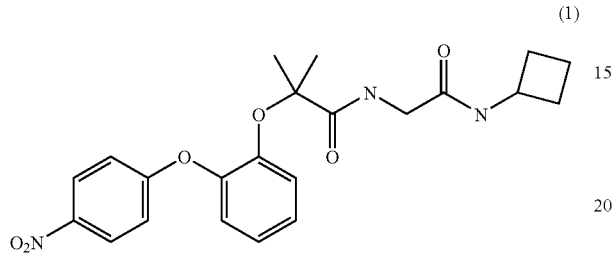
(1)

Step 1

Intermediate (4), example 43 was reacted with cyclobutylamine in the presence of DMAP/EDC/DCM at room temperature for 16 hr to give intermediate (1) above. The product was purified by chromatography.

Mass Spectrum m/e 426 (M− −H).

Step 2

Intermediate (1) was reduced to the corresponding aniline by reduction in ethyl acetate solution in the presence of hydrogen and catalytic Pd on C at room temperature for 3 hr.

Mass Spectrum m/e 398.3 (M+ +H).

Step 3

The product of step 2 was reacted with intermediate D, prepared as described above, in n-propanol solution at a temperature of 100° C. for 2 hr.

Mass Spectrum m/e 610.3 (M+ +H).

NMR Spectrum (d-6-DMSO, δ values) 1.34 (s, 6H), 1.60 (m, 2H), 1.83 (m, 2H), 2.12 (m, 2H), 3.65 (d, 2H), 3.98 (s, 3H), 3.99 (s, 3H), 4.18 (m, 1H), 7.00 (d, 2H), 7.05-7.18 (m, 3H), 7.23 (d, 1H), 7.35-7.43 (m, 3H), 7.94-8.08 (m, 3H), 8.85 (s, 1H)

Example 39

Preparation of Compound 39 in Table 5

Step 1

4-methoxybenzamine was reacted with ethyl(ethoxymethylene)cyanoacetate in ethanol at 95° C. for 2 hr and produced intermediate ethyl 3-(4-methoxyphenylamino)2-cyanoprop-2-enylcarboxylate.

Mass Spectrum m/e 245.17 (M−H)−

Step 2

Intermediate 2 was reacted with Dowtherm at 260° C. to give 3-cyano, 4-oxo, 6-methoxy dihydroquinoline.

Mass Spectrum m/e 199.3 (M−H)−

Step 3

3-cyano, 4-oxo, 6-methoxy dihydroquinoline was reacted with phosphorus oxychloride in acetonitrile at 85° C. for 5 hr to give 3-cyano, 4-chloro, 6-methoxy quinoline 97% purity by HPLC Step 4

3-cyano, 4-chloro, 6-methoxy quinoline was reacted with Intermediate C, prepared as described above, in n-propanol solution at 105° C./3 hr to give compound 39.

Mass Spectrum m/e 483.19 (M+H)+

NMR Spectrum (d-6-DMSO, δ values) 1.33 (s, 6H), 2.62 (d, 3H), 3.97 (s, 3H), 6.98-7.15 (m, 6H), 7.43-7.46 (d, 2H), 7.65-7.70 (m, 1H), 7.78 (m, 1H), 7.97-8.00 (d, 1H), 8.20 (m, 1H), 8.93 (s, 1H), 11.18 (bs, 1H) es Example 40

Preparation of Compound 40 in Table 5

Step 1

3-cyano, 4-chloro, 6-methoxy quinoline, prepared as described in example 39, was reacted with intermediate 1, example 24 in n-propanol solution at a temperature of 105° C. for 2 hr to give compound 40.

Mass Spectrum m/e 540.19 (M+H)+

NMR Spectrum (d-6-DMSO, δ values) 1.35 (s, 6H), 2.58 (d, 3H), 3.70 (d, 2H), 3.97 (s, 3H), 7.01-7.04 (d, 2H), 7.10-7.16 (m, 3H), 7.22-7.25 (d, 2H), 7.42-7.45 (d, 2H), 7.67-7.71 (m, 2H), 7.97-8.03 (m, 2H), 8.19 (m, 1H), 8.92 (s, 1H).

Example 41

Preparation of Compound 41 in Table 5

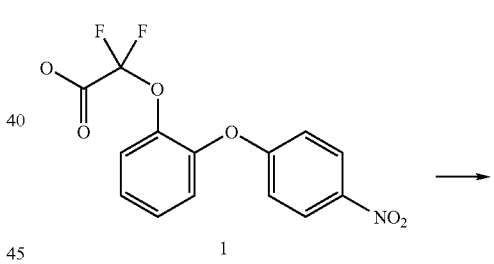
1

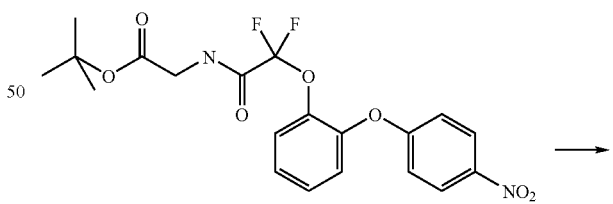
2

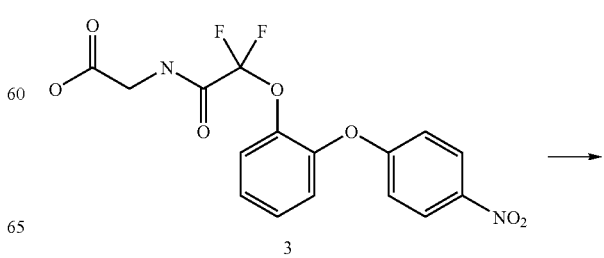
3

-continued

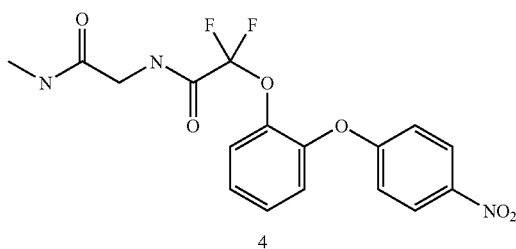

4

Step 1

Intermediate (1), example 30 was reacted with sodium hydroxide in methanol in water for 48 hrs to produce intermediate (1) in the above scheme.

Step 2

Intermediate 1 was reacted with glycine-t-butylester in the presence of HCl/EDC/DMAP/Dichloromethane at room temperature for 16 hrs to give intermediate (2)

Mass Spectrum m/e 411.09 (M$^+$+H).

Step 3

Intermediate (2) was reacted with TFA/Triethylsilane/Dichloromethane at room temperature for 16 hrs to give intermediate (3).

NMR Spectrum (d-6-DMSO, δ values) 3.77 (d, 2H), 7.09 (d, 2H), 7.3-7.46 (m, 3H), 7.5 (d, 1H), 8.22 (d, 2H), 9.25 (t, 1H), 12.55 (v.br.s, 1H).

Step 4

Intermediate (3) was reacted with methylamine in the presence of HCl/EDC/DMAP/Dichloromethane at room temperature for 16 hrs to give intermediate (4)

NMR Spectrum (d-6-DMSO, δ values) 2.56 (d, 3H),), 3.66 (d, 2H), 7.08 (d, 2H), 7.27-7.46 (m, 3H), 7.5 (d, 1H), 7.83 (br.q, 1H), 8.21 (d, 2H), 9.02 (br.t, 1 h).

Step 5

Intermediate (4) was reduced to the corresponding aniline by reduction in ethyl acetate solution in the presence of hydrogen and catalytic 5% Pd on C at room temperature for 2 hrs.

Mass Spectrum m/e 366.18 (M$^+$H).

Step 6

The product of step 5 was reacted with intermediate D, prepared as described above, in n-propanol solution at a temperature of 100° C. for 2 hr.

Mass Spectrum m/e 578.09 (M$^+$+H).

NMR Spectrum (d-6-DMSO, δ values) 2.59 (d, 3H), 3.74 (d, 2H), 3.97 (s, 6H), 7.04 (d, 1H), 7.14 (d, 2H), 7.2 (t, 1H), 7.29 (t, 1H), 7.43 (s, 1H), 7.45 (d, 1H), 7.5 (d, 2H), 7.9 (br.q, 1H), 8.1 (s, 1H), 8.9 (s, 1H), 9.1 (br.t, 1H), 11.0 (v.br.s, 1H).

Example 42

Preparation of Compound 42 in Table 5

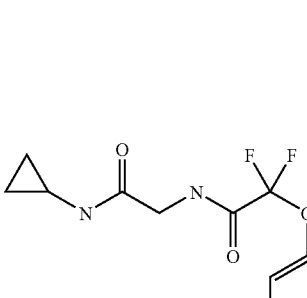

(1)

Step 1

Intermediate (3), example 41 was reacted with cyclopropylamine in the presence of EDC/DMAP/Dichloromethane at room temperature for 16 hrs to give intermediate (1) above.

NMR Spectrum (d-6-DMSO, δ values) 0.43 (m, 2H), 0.65 (d, 2H), 2.48 (m, 1H), 3.66 (d, 2H), 7.08 (d, 2H), 7.27-7.46 (m, 3H), 7.5 (d, 1H), 8.08 (br.d, 1H), 8.21 (d, 2H), 9.04 (br.t, 1 h).

Step 2

Intermediate (1) was reduced to the corresponding aniline by reduction in ethyl acetate solution in the presence of hydrogen and catalytic 5% Pd on C for 2 hrs.

Mass Spectrum m/e 392.16 (M$^+$+H).

Step 3

The product of step 2 was reacted with intermediate D, prepared as described above, in n-propanol solution at a temperature of 100° C. for 2 hr.

Mass Spectrum m/e 604.11 (M$^+$+H).

NMR Spectrum (d-6-DMSO, δ values) 0.42 (m, 2H), 0.64 (m, 2H), 2.64 (m, 1H), 3.74 (d, 2H), 3.97 (s, 6H), 7.04 (d, 1H), 7.14 (d, 2H), 7.2 (t, 1H), 7.29 (t, 1H), 7.43 (d, 1H), 7.45 (s, 1H), 7.5 (d, 2H), 7.9 (br.d, 1H), 8.1 (s, 1H), 8.9 (s, 1H), 9.1 (br.t, 1H), 11.1 (v.br.s, 1H).

Example 43

Preparation of Compound No. 43 in Table 5

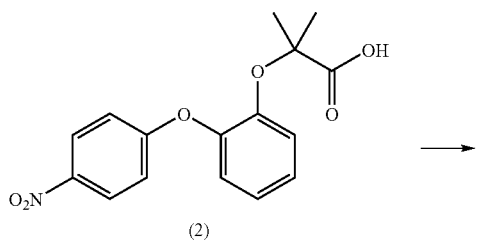

(2)

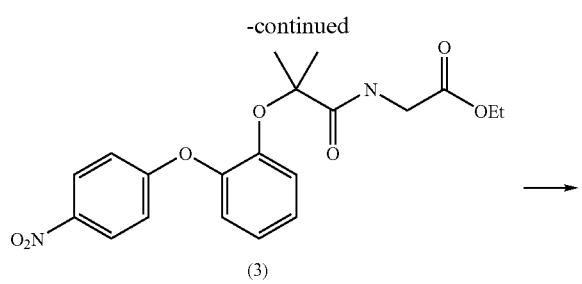

(3)

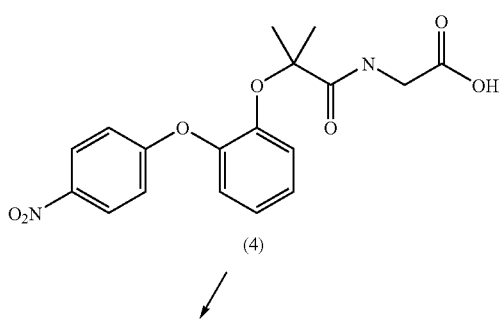

(4)

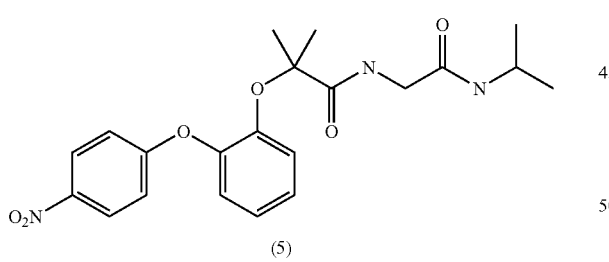

(5)

Step 1

Intermediate B1, described above, was reacted with sodium hydroxide in methanol at room temperature for 16 hrs to form the corresponding hydroxide Mass Spectrum m/e 316.4 (M⁻–H).

Step 2

The product of step 1 was then reacted with glycine ethyl ester in DMAP/EDAC at room temperature for 16 hrs to give Intermediate (3). The product was purified by chromatography.

Mass Spectrum m/e 425.1 (M⁺+Na).

Step 3

Intermediate (3) was converted to the corresponding hydroxide (intermediate 4) by reaction with sodium hydroxide in the presence of methanol at room temperature for 16 hrs.

Mass Spectrum m/e 375.2 (M⁺+H).

Step 5

Intermediate 4 was converted to intermediate 5 reaction with isopropylamine in DMAP/EDAC at room temperature for 16 hr. The product was purified by chromatography.

Mass Spectrum m/e 416.2 (M⁺+H).

Step 6

Intermediate 5 was then converted to the corresponding aniline by reduction at room temperature for 16 hrs in ethyl acetate solution with hydrogen and catalytic 5% Pd/C. Mass Spectrum m/e 386.4 (M⁺+H).

Step 7

Intermediate 6 was reacted with Intermediate D in n-propanol solution for 3 hr at 105° C. to produce the compound no. 43.

Mass Spectrum m/e 598.3 (M⁺+H).

NMR Spectrum (d-6-DMSO, δ values) 1.02 (d, 6H), 1.35 (s, 6H), 3.68 (d, 2H), 3.80 (m, 1H), 3.98 (s, 3H), 3.99 (s, 3H), 7.00 (d, 2H), 7.05-7.19 (m, 3H), 7.22 (d, 1H), 7.42 (d, 2H), 7.54 (s, 1H), 7.67 (d, 1H), 7.98 (t, 1H), 8.23 (s, 1H), 8.94 (s, 1H).

Example 44

Preparation of Example 44 in Table 5

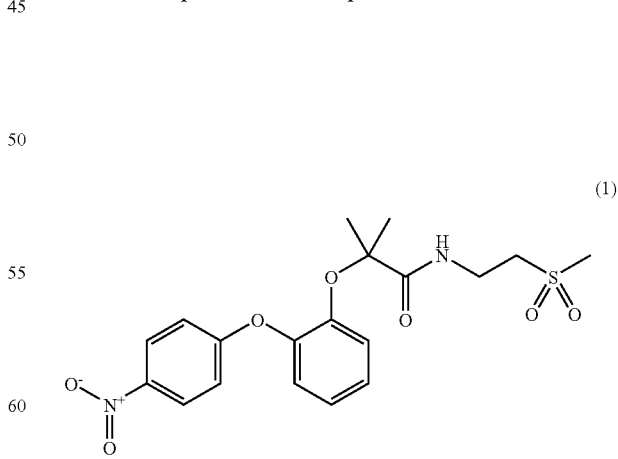

(1)

Step 1

Intermediate (2) example 43 was reacted with 2-(methanesulphonyl)ethylamine in DMAP/EDC/DCM at room temperature for 18 hr to give intermediate (1) above. The product was purified by chromatography.

Mass Spectrum m/e 423.3 (M+H)+.

Step 2

Intermediate 1 was then converted to the corresponding aniline by reduction at room temperature for 16 hrs in ethyl acetate solution with hydrogen and catalytic 5% Pd/C. The product was purified by chromatography.

Mass Spectrum m/e 393.3 (M+H)+.

Step 3

The product of step 2 was then reacted with Intermediate D in n-propanol solution for 3 hr at 105° C. to produce the compound no. 44.

Mass Spectrum m/e 605.3 (M+H)+.

NMR Spectrum (d-6-DMSO, δ values) 1.24 (s, 6H), 2.96 (s, 3H), 3.25 (t, 2H), 3.52 (q, 2H), 3.98 (s, 6H), 6.96-7.18 (m, 6H), 7.39-7.46 (m, 3H), 8.10-8.19 (m, 2H), 8.90 (s, 1H).

Example 45

Preparation of Compound No. 45 in Table 5

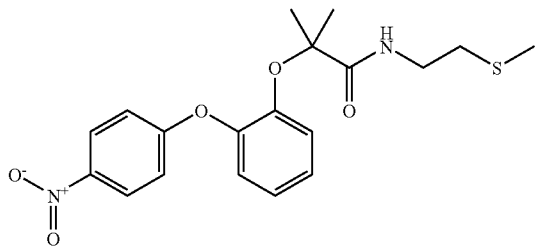

Step 1

Intermediate (2) example 43 was reacted with 2-(methylthio)ethylamine in DMAP/EDC/DCM at room temperature for 18 hr to give intermediate (1) above. The product was purified by chromatography.

Mass Spectrum m/e mass ion not observed (M+H)+.

NMR Spectrum (d-6-DMSO, δ values) 1.24 (s, 6H), 2.00 (s, 3H), 2.46 (t, 2H), 3.21 (q, 2H), 7.00-7.08 (m, 3H), 7.14 (t, 1H), 7.26 (t, 2H), 7.88 (t, 1H), 8.23 (d, 2H).

Step 2

Intermediate 1 was then converted to the corresponding aniline by reduction at room temperature for 16 hrs in ethyl acetate solution with hydrogen and catalytic 5% Pd/C. Mass Spectrum m/e 361.3 (M+H)+.

Step 3

The product of step 2 was then reacted with Intermediate D in n-propanol solution for 3 hr at 105° C. to produce the compound no. 45.

Mass Spectrum m/e 573.3 (M+H)+.

NMR Spectrum (d-6-DMSO, δ values) 1.35 (s, 6H), 2.03 (s, 3H), 2.51 (t, 2H), 3.28 (q, 2H), 3.98 (s, 6H), 6.97-7.18 (m, 6H), 7.38-7.46 (m, 3H), 7.99 (t, 1H), 8.12 (s, 1H), 8.90 (s, 1H).

Example 46

Preparation of Compound No. 46 in Table 5

Step 1

Intermediate 2, example 43 was reacted with 2-(pyrid-3-yl)-ethylamine in the presence of HOBT/N-Methyl morpholine/EDC/DMA at room temperature for 16 hr to produce intermediate (1) in the scheme above.

Mass Spectrum m/e 422.3 (M+H)+.

Step 2

Intermediate (1) was then converted to the corresponding aniline by reduction at room temperature in ethyl acetate solution with hydrogen and catalytic 10% Pd on C at room temperature for 36 hr.

Mass Spectrum m/e 392.3 (M+H)+.

Step 3

The product of step 2 was then reacted with Intermediate D described above in n-propanol solution in the presence of 1.0M Ethereal HCl at 105° C. for 3 hr. The product was purified by chromatography.

Mass Spectrum m/e 604.3 (M+H)+.

NMR Spectrum (d-6-DMSO, δ values) 1.26 (s, 6H), 2.94 (t, 2H), 3.47 (q, 2H), 3.98 (s, 3H), 3.99 (s, 3H), 6.86 (d, 1H), 6.96 (d, 2H), 7.05-7.14 (m, 3H), 7.42 (d, 2H), 7.49 (s, 1H), 7.60 (m, 1H) 8.00 (t, 1H), 8.21-8.27 (m, 2H), 8.67-8.71 (m, 2H), 8.92 (s, 1H), 11.22 (bs, 1H).

Example 47

Preparation of Compound No. 47 in Table 5

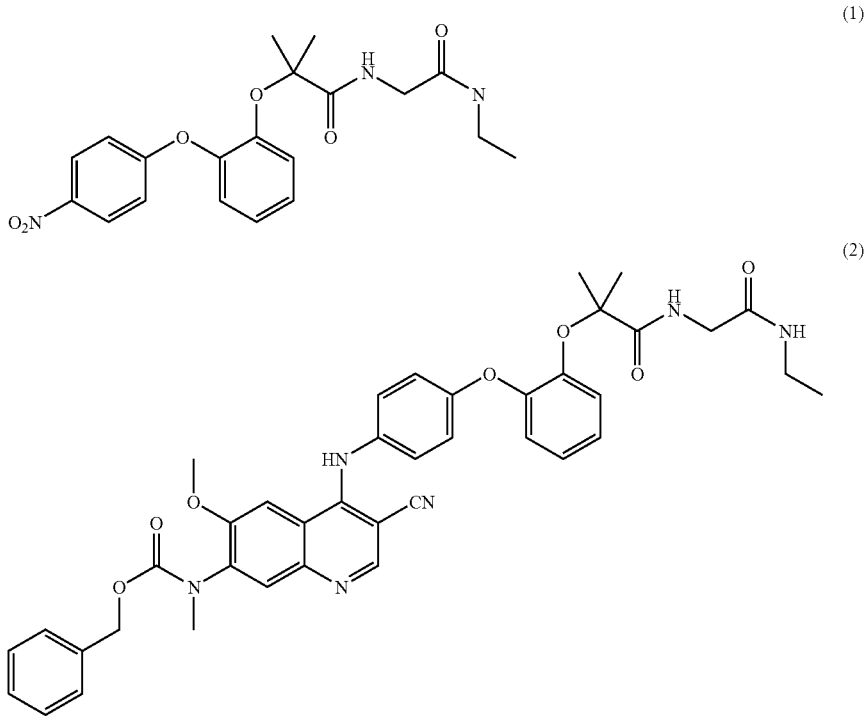

Step 1

Intermediate 4, example 43 with ethylamine hydrochloride/EDC/at room temperature for 16 hr to give intermediate (1) above Mass Spectrum m/e 402.3 (M+H)+

Step 2

Intermediate 1 was then converted to the corresponding aniline by reduction at room temperature for 3 hrs in ethyl acetate solution with hydrogen and catalytic Pd/C.

Mass Spectrum m/e 370.5 (M−H)−

Step 3

The product of step 2 was reacted with Intermediate D, prepared as described above, in n-propanol solution for 2 hr at 100° C. to produce intermediate (2)
Mass Spectrum m/e 717.3 (M+H)+

Step 3

Intermediate (2) was reacted with 33% HBr in acetic acid for 2 hr.
Mass Spectrum m/e 583.2 (M+H)+
NMR Spectrum (d-6-DMSO, CD₃CO₂D, δ values) 0.97 (t, 3H), 1.35 (s, 6H), 2.85 (s, 3H), 3.07 (q, 2H), 3.68 (m, 2H), 4.00 (s, 3H), 6.67 (s, 1H), 7.00 (d, 2H), 7.10 (m, 3H), 7.22 (d, 1"), 7.38 (d, 2H), 7.83 (s, 1H), 7.96 (m, 1H), 8.81 (s, 1H)1

Example 48

Preparation of Compound 48 in Table 5

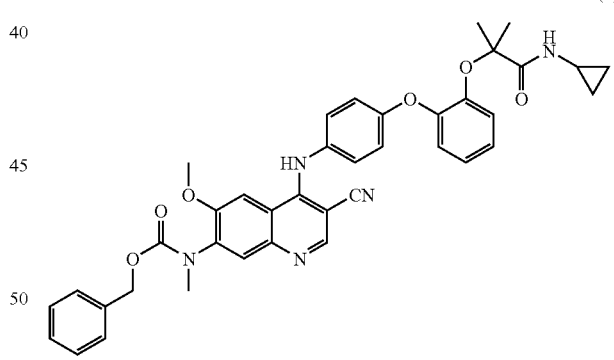

Step 1

Intermediate E2, example 26 was reacted with Intermediate F in n-propanol at 100° C. for 2 hr to give intermediate (1) above
Mass Spectrum m/e 672.3 (M+H)+

Step 2

Intermediate (1) was reacted in 33% HBr in acetic acid for 2 hrs to give compound 48. The compound was purified by chromatography.
Mass Spectrum m/e 538.3 (M+H)+
NMR Spectrum (d-6-DMSO, δ values) 0.05 (m, 2H), 0.20 (m, 2H), 0.93 (s, 6H), 2.30 (m, 1H), 2.47 (q, 3H), 3.61 (s, 3H), 6.31 (s, 1H), 6.57 (m, 3H), 6.66 (m, 1H), 6.77 (m, 1H), 7.00 (d, 2H), 7.48 (m, 2H), 7.48 (m, 2H), 8.40 (s, 1H), 10.25 (s, 1H)

Example 49

Preparation of Compound No. 49 in Table 5

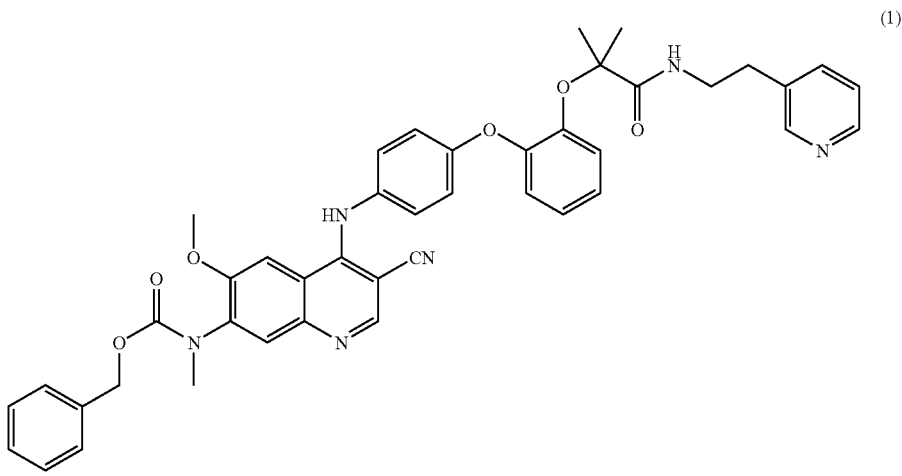

Step 1
The aniline derivative of step 2 of example 46 was reacted with Intermediate 2, example 26 in n-propanol at 100° C. for 105 min to give intermediate (1) above
Mass Spectrum m/e 737.7 (M+H)$^+$

Step 2
Intermediate (1) was then reacted in 33% HBr in acetic acid for 2 hrs to give compound 49.
Mass Spectrum m/e 603.3 (M+H)$^+$
NMR Spectrum (d-6-DMSO, CD$_3$CO$_2$D, δ values) 1.25 (s, 6H), 2.85 (s, 3H), 2.92 (t, 2H), 3.46 (m, 2H), 4.00 (s, 3H), 6.70 (s, 1H), 6.83 (d, 1H), 6.95 (d, 2H), 7.07 (m, 3H), 7.39 (m, 3H), 7.76 (m, 1H), 7.91 (m, 1H), 8.02 (m, 1H), 8.19 (m, 1H), 8.67 (m, 2H), 8.80 (s, 1H)

Example 50

Preparation of Compound No. 50 in Table 5

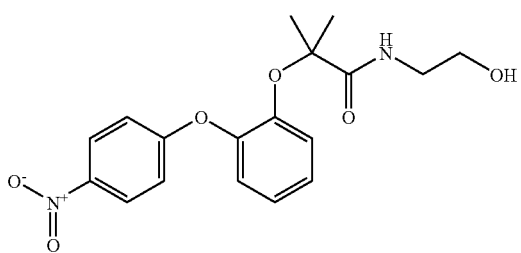

Step 1
Intermediate 2, example 43 was reacted with 2-(hydroxy)ethylamine in the presence of DMAP/EDC/DMA at room temperature for 18 hrs to produce intermediate (1) in the scheme above.
Mass Spectrum m/e 361.3 (M+H)$^+$.

Step 2
Intermediate (1) was then converted to the corresponding aniline by reduction at room temperature in ethyl acetate solution with hydrogen and catalytic 5% Pd on C at room temperature for 18 hr.
Mass Spectrum m/e 333.1 (M+H)$^+$.

Step 3
The product of step 2 was then reacted with Intermediate D, prepared as described above, in n-propanol solution at 105° C. for 3 hr to give compound 50.
Mass Spectrum m/e 543.3 (M+H)$^+$.
NMR Spectrum (d-6-DMSO d-4-Acetic, δ values) 1.34 (s, 6H), 3.16 (q, 2H), 3.39 (t, 2H), 3.99 (s, 6H), 6.97-7.18 (m, 6H), 7.41 (s, 1H), 7.44 (s, 2H), 7.76 (t, 1H), 8.15 (s, 1H), 8.90 (s, 1H).

Example 51

Preparation of Compound 51 in Table 5

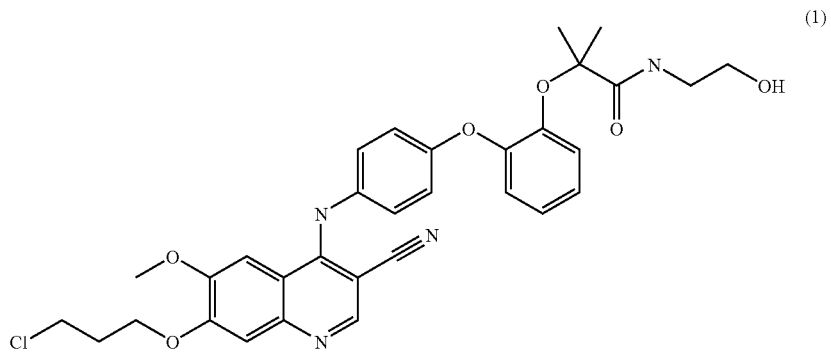

Step 1

Intermediate (1), example 50 was reacted with Intermediate (A) in n-propanol solution at 105° C. for 3.5 hr to give intermediate (1) above.

Mass Spectrum m/e 605.3 (M+H)⁺

Step 2

Intermediate (1) was reacted with n-morpholine in sodium iodide at room temperature for 3 days to give compound 51. The product was purified by chromatography Mass Spectrum m/e 656.3 (M+H)⁺

NMR Spectrum (d-6-DMSO d-4-Acetic, δ values) 1.34 (s, 6H), 2.31 (m, 2H), 3.10 (m, 2H), 3.17 (t, 2H), 3.29 (t, 2H), 3.38 (t, 2H), 3.48 (m, 2H), 3.80 (m, 2H), 3.95 (m, 2H), 3.99 (s, 3H), 4.30 (t, 2H), 6.97-7.17 (m, 6H), 7.41 (d, 2H), 7.46 (s, 1H), 7.71 (t, 1H), 8.12 (s, 1H), 8.90 (s, 1H).

Example 52

Preparation of compound 52 in Table 5

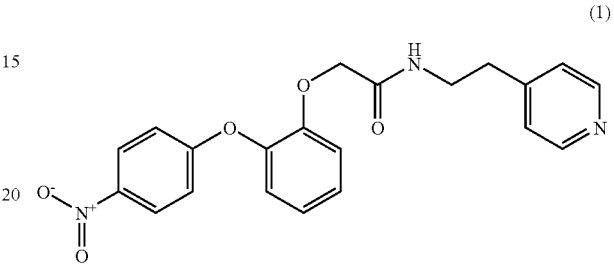

Step 1

Intermediate B1, prepared as described above, was reacted with formamide in the presence of 5% NaOMe in MeOH/DMA at 100° C. for 1 hr to give intermediate (1). The product was purified by chromatography.

Mass Spectrum m/e 315 (M–H)⁻.

Step 2

Intermediate (1) was then converted to the corresponding aniline by reduction at room temperature in ethyl acetate solution with hydrogen and catalytic 5% Pd on C at room temperature for 3 hr.

Mass Spectrum m/e 287.2 (M+H)⁺.

Step 3

The product of step 2 was then reacted with Intermediate D, prepared as described above, in n-propanol solution at 105° C. for 3 hr to give compound 52.

Mass Spectrum m/e 499.2 (M+H)⁺.

NMR Spectrum (d-6-DMSO, δ values) 1.34 (s, 6H), 3.98 (s, 6H), 6.97-7.19 (m, 6H), 7.25 (d, 2H), 7.39-7.46 (m, 3H), 8.12 (s, 1H), 8.90 (s, 1H), 11.02 (bs, 1H).

Example 52A

Preparation of compound 52A in Table 5

Step 1

4-(fluoro)nitrobenzene was reacted with 2-(2-hydroxyphenoxy)acetic acid in the presence of potassium t-butoxide/DMA at 150° C. for 2 hrs to give 2-[(2-(4-nitrophenoxy)phenoxy] acetic acid. The product was purified by chromatography.

Mass Spectrum m/e 288 (M–H⁺)⁻

Step 2

The product of step 1 was reacted with 2-(pyrid-4-yl)-ethylamine in the presence of N-methyl morpholine/HOBT/EDC/DCM at room temperature for 16 hrs to produce intermediate (1) above.

Mass Spectrum m/e 394.3 (M+H)⁺.

Step 3

Intermediate (1) was then converted to the corresponding aniline by reduction at room temperature in ethyl acetate solution with hydrogen and catalytic 10% Pd on C at room temperature for 18 hr.

Mass Spectrum 364.3 (M+H)⁺.

Step 4

The product of step 3 was then reacted with Intermediate D, prepared as described above, in n-propanol solution in the presence of 1.0M Ethereal HCl 105° C. for 3 hr to give compound 52A.

Mass Spectrum m/e 576.3 (M+H)⁺.

NMR Spectrum (d-6-DMSO, δ values) 3.01 (t, 2H), 3.50 (q, 2H), 3.98 (s, 3H), 3.99 (s, 3H), 4.44 (s, 2H), 6.95-7.05 (m, 4H), 7.13 (m, 1H), 7.41 (d, 2H), 7.50 (s, 1H), 7.83 (d, 2H), 7.90 (t, 1H) 8.24 (s, 1H), 8.74 (d, 2H), 8.92 (s, 1H).

103

Example 52B

Preparation of Compound No. 52B in Table 5

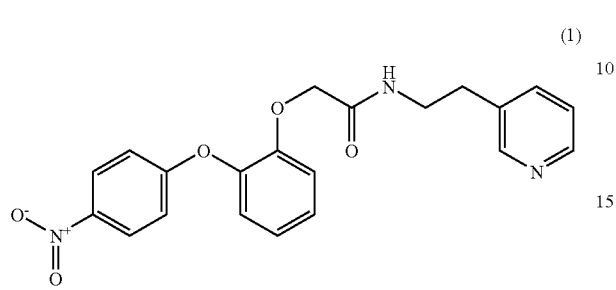

(1)

Step 1

2[(2-(4-nitrophenoxy)phenoxy] acetic acid from example 52A was reacted with 2-(pyrid-3-yl)-ethylamine in the presence of N-methyl morpholine/HOBT/EDC/DCM at room temperature for 3 days produce intermediate (1) above.

Mass Spectrum m/e 394.3 (M+H)$^+$.

Step 2

Intermediate (1) was then converted to the corresponding aniline by reduction at room temperature in ethyl acetate solution with hydrogen and catalytic 10% Pd on C at room temperature for 16 hr.

Mass Spectrum 364.3 (M+H)$^+$.

Step 3

The product of step 2 was then reacted with Intermediate D, prepared as described above in n-propanol solution in the presence of 2.0M Ethereal HCl 105° C. for 3 hr to give compound 52B.

Mass Spectrum m/e 576.3 (M+H)$^+$.

NMR Spectrum (d-6-DMSO, δ values) 2.92 (t, 2H), 3.46 (q, 2H), 3.98 (s, 6H), 4.44 (s, 2H), 6.95-7.06 (m, 4H), 7.15 (t, 1H), 7.41 (d, 2H), 7.48 (s, 1H), 7.78-7.89 (m, 2H) 8.20 (s, 1H), 8.26 (d, 1H), 8.70 (d, 1H), 8.74 (s, 1H), 8.91 (s, 1H).

Example 52C

Preparation of Compound 52C in Table 5

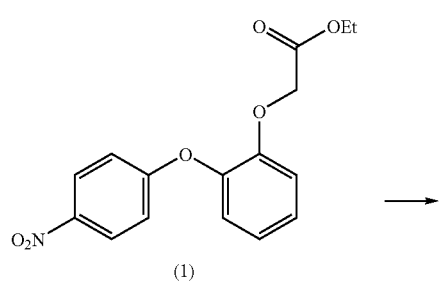

(1)

104

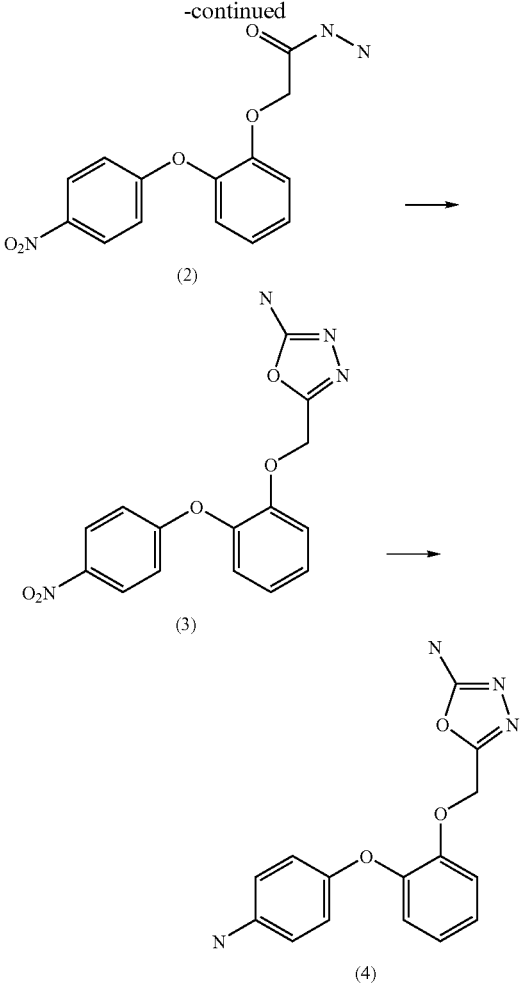

Step 1

Intermediate B, prepared as described above, was reacted with ethyl bromoacetate in the presence of K$_2$CO$_3$ and acetone and refluxed for 18 hr to give intermediate (1) in the above scheme. The product was purified by chromatography.

Mass Spectrum m/e 316 (M−H)

Step 2

Intermediate (1) was then reacted with hydrazine hydrate in ethanol and refluxed for 6.5 hr to give intermediate (2). The product was purified by chromatography.

Mass Spectrum m/e 304 (M$^+$+H)

Step 3

Intermediate (2) was reacted with cyanogen bromide in the presence of dioxane and NaHCO$_3$ or 5.5 hr to give intermediate (3).

Mass Spectrum m/e 329 (M$^+$+H)

Step 4

Intermediate (3) was then converted to the corresponding aniline by reduction at room temperature in ethyl acetate solution with hydrogen and catalytic % Pd on C at room temperature for 18 hr. The product was purified by chromatography.

Mass Spectrum m/e 299 (M$^+$+H)

Step 5

The product of step 4 was then reacted with Intermediate D, prepared as described above in n-propanol solution at 110° C. for 18 hr to give compound 52C.

Mass Spectrum m/e 511 (M⁺+H)

NMR Spectrum (d-6-DMSO, δ values) 4.0 (s, 6H), 5.15 (s, 2H), 7.0 (d, 2H), 7.0 (s, 2H), 7.15 (m, 3H), 7.3 (d, 1H), 7.4 (d, 2H), 7.45 (s, 1H), 8.2 (s, 1H), 8.9 (s, 1H), 11.2 (br s, 1H)

Example 52D

Preparation of Compound 52D in Table 5

Step 1

Intermediate D2, example 26 was reacted with KHMDS/Ac₂O/18-Crown-6/THF ar room temperature for 150 min to give intermediate (1) above.

Mass Spectrum m/e 410.2 (M+H)⁺

Step 2

Intermediate (1) was reacted with 33% HBr in acetic acid for 2 hr to give intermediate (2) above.

Mass Spectrum m/e 322.1 (M+H)⁺

Step 3

Intermediate (2) was reacted with intermediate (1), example 24 in n-propanol solution at 100° C. for 2 hr to give compound 52D.

Mass Spectrum m/e 597.5 (M+H)⁺

NMR Spectrum (d-6-DMSO, δ values) 1.34 (s, 6H), 2.24 (s, 3H), 2.58 (d, 3H), 3.68 (d, 2H), 4.05 (s, 3H), 7.04 (d, 2H), 7.10 (m, 3H), 7.22 (d, 1H), 7.43 (d, 2H), 7.69 (m, 1H), 8.01 (t, 1H), 8.08 (s, 1H), 8.90 (d, 2H), 9.84 (s, 1H), 10.81 (bs, 1H)

Example 53

Preparation of Compound 53 in Table 6

This compound was prepared as outlined in the following reaction scheme.

Step 1

Intermediate (1) was prepared by reacting nitroaniline with benzyl chloroformate pyridine in the presence of pyridine at room temperature for 20 hr.

Mass Spectrum m/e 271.4 (M−H)⁻

Step 2

Intermediate (1) was reacted with Fe/glacial acetic acid/ethanol/water at 100° C. for 1.75 hr to give intermediate (2). The product was purified by chromatography.

Mass Spectrum m/e 243.3 (M+H)⁺

Step 3

Intermediate (2) was reacted in KHMDS/MeI/18-crown-6 ether/THF at a temperature within the range 0° C.-25° C. for 1.5 hr to give intermediate (3). The product was purified by chromatography.

Mass Spectrum m/e 257.3 (M+H)+.

Step 4

Intermediate (3) was reacted with ethyl(ethoxymethylene)cyanoacetate in the presence of ethanol at 95° C. for 4 hr to give intermediate (4).

Mass Spectrum m/e 380.3 (M+H)+

Step 5

Intermediate (4) was reacted with Dowtherm at 260° C. for 4 hr to give intermediate (5). Mass Spectrum m/e 334.2 (M+H)+

Step 6

Intermediate (5) was converted to intermediate (6) by reaction with POCl$_3$ in acetonitrile conditions at 85° C. for 1.5 hr.

Mass Spectrum m/e 352.2 (M+H)+

Step 7

Intermediate 6 was reacted with Intermediate C, prepared as described above, in n-propanol solution at 105° C. for 2 hr.

Mass Spectrum m/e 616.4 (M+H)+

Step 8

Intermediate (8) was reacted in 33% HBr in glacial acetic acid/thioanisole at room temperature for 2 hr to give compound 53.

Mass Spectrum m/e 482.6 (M+H)+

NMR Spectrum (d-6-DMSO, δ values) 1.32 (s, 6H), 2.60 (m, 3H), 2.83 (s, 3H), 6.34 (s, 1H), 6.95-6.99 (m, 3H), 7.07-7.16 (m, 4H), 7.22-7.31 (m, 1H), 7.37-7.40 (d, 2H), 8.29-8.32 (d, 1H), 8.86 (s, 1H).

Example 54

Preparation of Compound No. 54 in Table 6

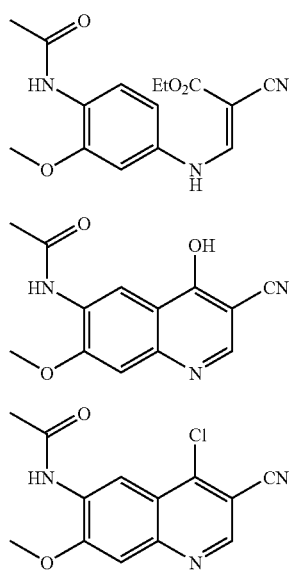

Example 55

Preparation of Compound No. 55 in Table 7

2-(phenoxy(4-amino))4-methoxypyridine, example 56, was reacted with Intermediate A1, prepared as described above, in n-propanol solution at 100° C. for 2 hrs to give compound 55.

Mass Spectrum m/e 542.3 (M+H)+

NMR Spectrum (d-6-DMSO, CD$_3$CO$_2$D, δ values) 2.30 (m, 2H), 3.12 (m, 2H), 3.30 (m, 2H), 3.50 (m, 2H), 3.78 (m, 5H), 3.98 (m, 5H), 4.30 (t, 2H), 6.52 (d, 1H), 6.77 (m, 1H), 7.23 (d, 2H), 7.45 (m, 3H), 8.00 (d, 1H), 8.09 (m, 1H), 8.89 (bs, 1H)

Example 56

Preparation of Compound No. 56 in Table 7

Step 1

4-Aminophenol was reacted with 4-methoxy-2-chloropyridine in the presence of KO$^t$Bu/8-Crown-6/DMA at 150° C. for 5 hrs to give 2-(4-aminophenoxy)-4-methoxypyridine. The product was purified by chromatography.

Mass Spectrum m/e 217.3 (M+H)+

Step 2

2-(4-aminophenoxy)-4-methoxypyridine was reacted with Intermediate D, prepared as described above, in n-propanol solution at a temperature within the range 100-110° C. for 330 min to give compound 56.

Mass Spectrum m/e 429.2 (M+H)+

Step 1 (col. 108)

Acetamide, N-(4-amino-2-methoxyphenyl) was reacted with ethyl (ethoxymethylene)cyanoacetate in ethanol and refluxed for 2 hr to give intermediate (1).

Mass Spectrum m/e 302.2 (M–H)–

Step 2

Intermediate (1) was reacted with Dowtherm A at 261° C. for 210 min to give intermediate (2).

Mass Spectrum m/e 256.1 (M–H)–

Step 3

Intermediate (2) was reacted with methyl cyanide in POCl$_3$ for 4 hr at 100° C. to give intermediate (3).

Mass Spectrum m/e 275.7 (M+H)+

Step 4

Intermediate (3) was reacted with Intermediate (F), prepared as described above, in n-n-propanol solution at 100° C. for 2 hr to give compound 54. The product was purified by chromatography.

Mass Spectrum m/e 566.0 (M+H)+

NMR Spectrum (d-6-DMSO, δ values) 0.04 (m, 2H), 0.20 (m, 2H), 0.93 (s, 6H), 1.78 (s, 3H), 2.28 (m, 1H), 3.65 (s, 3H), 6.57 (s, 3H), 6.68 (m, 3H), 6.99 (m, 2H), 7.15 (s, 1H), 7.48 (s, 1H), 8.55 (s, 1H), 8.69 (s, 1H), 9.34 (s, 1H), 10.64 (bs, 1H)

NMR Spectrum (d-6-DMSO, CD₃CO₂D, δ values) 3.81 (s, 3H), 3.96 (d, 6H), 6.53 (d, 1H), 6.75 (m, 1H), 7.23 (d, 2H), 7.39 (s, 1H), 7.45 (d, 2H), 8.03 (m, 2H), 8.92 (bs, 1H)

Example 57

Preparation of Compound No. 57 in Table 7

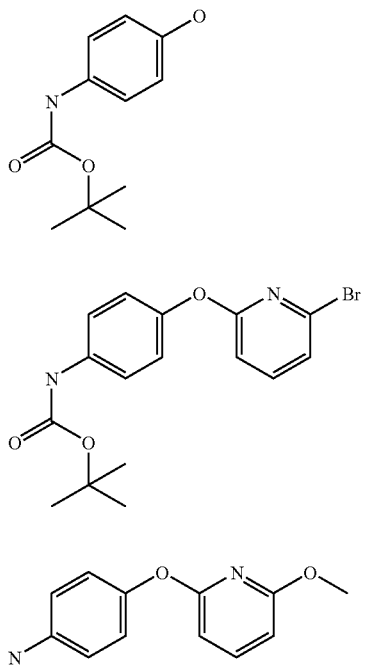

Step 1

4-hydroxyaniline was reacted with Boc₂O in the presence of 1M Na₂CO₃ and THF to give intermediate (1) in the above scheme.

Mass Spectrum m/e 208 (M−H)⁻.

Step 2

Intermediate (1) was reacted with 2,6-dibromopyridine in the presence of potassium-t-butoxide and DMA to give intermediate (2).

Step 3

Intermediate (2) was reacted with potassium methoxide in the presence of DMA at 100° C. for 1 hr to give intermediate (3).

Mass Spectrum m/e 217.2 (M⁺+H).

Step 4

Intermediate (3) was reacted with Intermediate A1, prepared as described above, in n-proanol solution in the presence of 1M ethereal HCl at 100° C. for 4 hr to give compound 57. The product was purified by chromatography.

Mass Spectrum m/e 542.25 (M⁺+H).

NMR Spectrum (d-6-DMSO, δ values) 2.2-2.43 (m, 2H), 3.09 (m, 2H), 3.28 (m, 2H), 3.48 (m, 2H), 3.7 (s, 3H), 3.8 (m, 2H), 3.95 (m, 2H), 4.0 (s, 3H), 4.3 (t, 2H), 6.52 (2d, 2H), 7.28 (d, 2H), 7.49 (d, 2H), 7.52 (s, 1H), 7.73 (t, 1H), 8.2 (s, 1H), 8.89 (s, 1H), 11.1 (v.br.s, 2H).

Example 58

Preparation of Compound No. 58 in Table 8

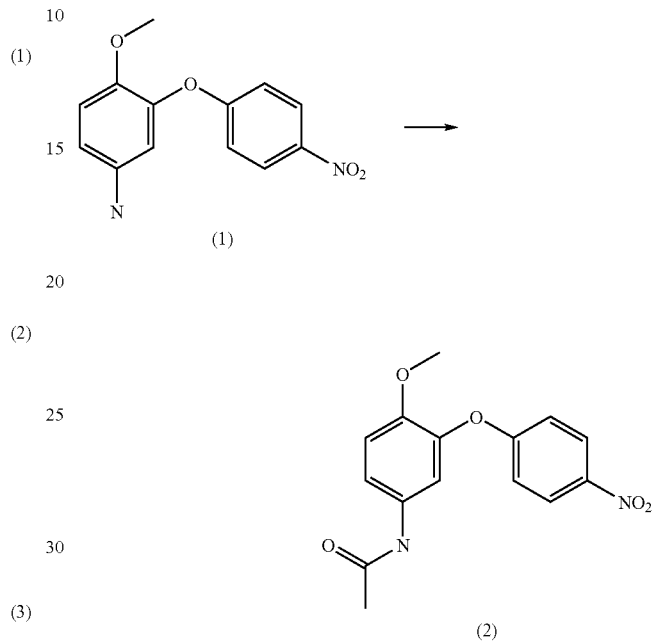

Step 1

5-Amino-2-methoxyphenol was reacted with 4-fluoronitrobenzene in potassium-t-butoxide and DMA at 150° C. for 5 min to give intermediate (1).

Mass Spectrum m/e 261.22 (M⁺+H).

Step 2

Intermediate 1 was reacted with pyridine in the presence of acetic anhydride for 48 hr to give intermediate (2).

Mass Spectrum m/e 303.25 (M⁺+H).

Step 3

Intermediate (2) was converted to the corresponding aniline derivative by reduction with hydrogen in the presence of catalytic 5% Pd on C.

Step 4

The product of step 3 was reacted with Intermediate A1, prepared as described above, in n-propanol solution in the presence of 1M ethereal HCl at 100° C. for 2 hr. The product was purified by chromatography (5-10% methanol/dichloromethane)

Mass Spectrum m/e 598.25 (M⁺+H).

NMR Spectrum (d-6-DMSO, δ values) 1.99 (s, 3H), 2.31 (m, 2H), 3.1 (m, 2H), 3.2-3.6 (m, 4H), 3.68 (s, 3H), 3.8 (t, 2H), 3.95 (m, 2H), 3.98 (s, 3H), 4.29 (t, 2H), 6.94 (d, 2H), 7.1 (d, 1H), 7.34 (m, 1H), 7.4 (d, 2H), 7.49 (d, 1H), 7.54 (s, 1H), 8.19 (s, 1H), 8.91 (s, 1H), 9.94 (s, 1H), 11.15 (v.br.s, 2H).

Example 59

Preparation of Compound No. 59 in Table 8

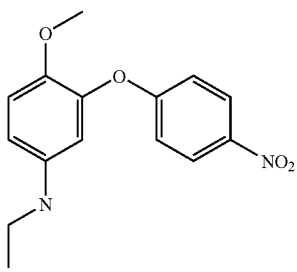

(1)

Step 1

Intermediate (2), example 58 was reacted with borane-THF to give intermediate (1) above.

Mass Spectrum m/e 289.18 (M⁺+H).

Step 2

Intermediate (1) was converted to the corresponding aniline by reduction with hydrogen in the presence of catalytic 5% Pd on C.

Step 3

The product of step 2 was reacted with Intermediate D, prepared as described above, in n-propanol solution at 100° C. for 2 hr to give compound 59.

Mass Spectrum m/e 471.24 (M⁺+H).

NMR Spectrum (d-6-DMSO, δ values) 1.15 (t, 3H), 3.12 (q, 2H), 3.7 (s, 3H), 3.96 (s, 6H), 6.88 (d, 1H), 6.99 (d, 3H), 7.16 (d, 1H), 7.4 (d, 2H), 7.43 (s, 1H), 8.09 (s, 1H), 8.8 (s, 1H), 10.83 (v.br.s, 1H).

Example 60

Preparation of Compound No. 60 in Table 8

The aniline derivative of step 2 of example 59 was reacted with Intermediate A1, prepared as described above, in n-propanol solution in the presence of 1M ethereal HCl at 100° C. for 2 hr to give compound 60.

Mass Spectrum m/e 584.26 (M⁺+H).

NMR Spectrum (d-6-DMSO, δ values) 1.18 (t, 3H), 2.32 (m, 2H), 3.0-3.68 (m, 8H), 3.73 (s, 3H), 3.82 (t, 2H), 3.95 (m, 2H), 3.99 (s, 3H), 4.29 (t, 2H), 7.0 (d, 2H), 7.09 (m, 1H), 7.22 (m, 2H), 7.4 (d, 2H); 7.53 (s, 1H), 8.23 (s, 1H), 8.87 (s, 1H), 11.16 (v.br.s, 2H).

Example 61

Preparation of Compound No. 61 in Table 8

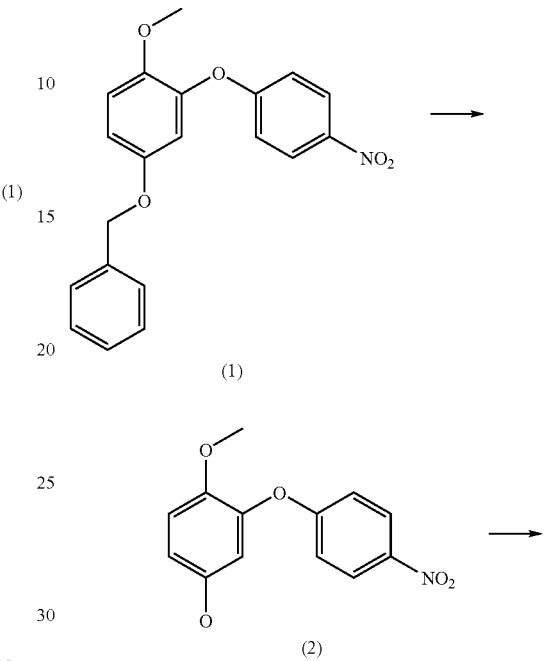

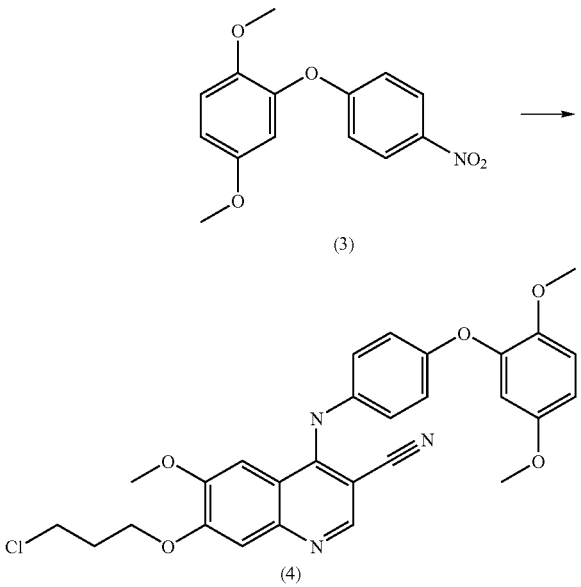

Step 1

4-Benzyloxy-2-methoxyphenol was reacted with 4-fluoronitrobenzene in the presence of potassium-t-butoxide and DMA to give intermediate (1).

Mass Spectrum m/e 299.99 (M⁺+H).

Step 2

Intermediate (1) was reacted with thioanisole in THF to give intermediate (2).

Step 3

Intermediate (2) was reacted with methyl iodide in potassium carbonate to give intermediate (3).

Step 4

Intermediate (3) was converted to the corresponding aniline derivative by reduction with hydrogen in the presence of catalytic 5% Pd on C.

Step 5

The aniline derivative of step 4 was reacted with Intermediate A, prepared as described above, in n-propanol solution at 100° C. for 2 hr to give intermediate (4).

Step 6

Intermediate (4) was reacted with morpholine in sodium iodide to give compound 61. the product was purified by chromatography (10-20% Methanol/dichloromethane)

Mass Spectrum m/e 571.27 (M$^+$+H).

NMR Spectrum (d-6-DMSO, δ values) 2.33 (m, 2H), 3.08 (m, 2H), 3.28 (m, 2H), 3.48 (m, 2H), 3.64 (s, 3H), 3.67 (s, 3H), 3.81 (t, 2H), 3.95 (m, 2H), 3.98 (s, 3H), 4.29 (t, 2H), 6.62 (d, 1H), 6.73 (2d, 1H), 7.0 (d, 2H), 7.08 (d, 1H), 7.4 (d, 2H), 7.52 (s, 1H), 8.08 (s, 1H), 8.9 (s, 1H), 11.13 (v.br.s, 2H).

Example 62

Preparation of Compound No. 62 in Table 8

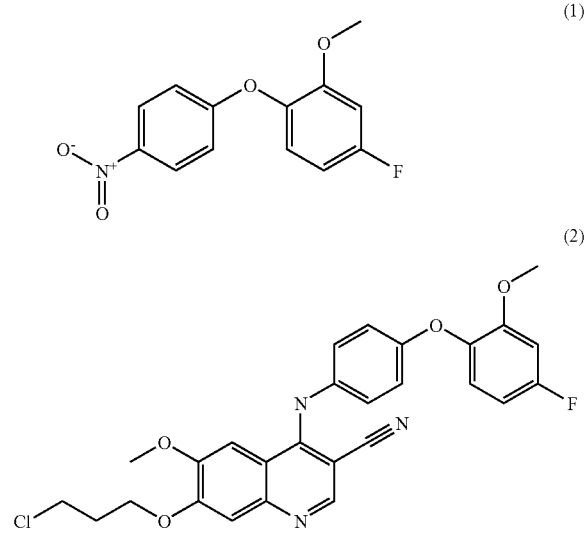

Step 1

4-Fluoro-2-methoxyphenol was reacted with KOtBu/DMA at room temperature for 20 min and then with 4-fluoronitrobenzene at 150° C. for 2 hr to give intermediate (1).

NMR Spectrum (d-6-DMSO, δ values) 3.73 (s, 3H), 6.86 (m, 1H), 6.98 (d, 2H), 7.16 (dd, 1H), 7.25 (dd, 1H), 8.19 (d, 2H).

Step 2

Intermediate (1) was converted to the corresponding aniline derivative by reduction with hydrogen in the presence of catalytic 5% Pd on C at room temperature.

NMR Spectrum (d-6-DMSO, δ values) 3.75 (s, 3H), 4.79 (s, 2H), 6.51 (d, 2H), 6.57-6.70 (m, 3H), 6.79 (m, 1H), 6.99 (dd, 1H).

Step 3

The product of step 2 was then reacted with Intermediate A in n-propanol solution at 105° C. for 3 hr to give intermediate (2)

Mass Spectrum m/e 508.24 (M$^+$+H).

Step 4

Intermediate (2) was then reacted with piperidine in the presence of NaI at room temperature for 18 hr to give compound 62. The product was purified by chromatography.

Mass Spectrum m/e 557.4 (M+H)$^+$

NMR Spectrum (d-6-DMSO D4 Acetic, δ values) 1.64-1.89 (m, 6H), 2.30 (m, 2H), 2.91 (m, 2H), 3.20 (m, 2H), 3.48 (m, 2H), 3.72 (s, 3H), 3.97 (s, 3H), 4.28 (m, 2H), 6.74-6.82 (m, 1H), 6.91-6.98 (m, 2H), 7.05-7.14 (m, 2H), 7.39 (d, 2H), 7.50 (s, 1H), 8.15 (s, 1H), 8.94 (s, 1H).

Example 63

Preparation of Compound No. 63 in Table 8

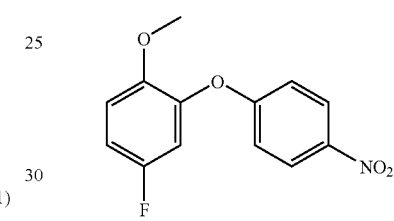

Step 1

Intermediate (1), example 58 was reacted with tetrafluoroboric acid and sodium nitrite in in H$_2$O and was then heated to give intermediate (1) above.

Mass Spectrum m/e 264.17 (M$^+$+H).

Step 2

Intermediate (1) was converted to the corresponding aniline derivative by reduction with hydrogen in the presence of catalytic 5% Pd on C.

Step 3

The product of step 2 was then reacted with Intermediate D, prepared as described above, in n-propanol solution at 100° C. for 2 hr to give compound 63.

Mass Spectrum m/e 446.13 (M$^+$+H).

NMR Spectrum (d-6-DMSO, δ values) 3.74 (s, 3H), 3.97 (s, 6H), 6.88 (m, 1H), 7.0 (m, 1H), 7.07 (d, 2H), 7.15 (m, 1H), 7.45 (d, 2H), 7.47 (s, 1H), 8.14 (s, 1H), 8.9 (s, 1H), 11.12 (br.s, 1H).

Example 64

Preparation of Compound 64 in Table 8

The aniline derivative of step 2, example 63 was reacted with Intermediate A1, prepared as described above in n-propanol solution in the presence of 1M ethereal HCl at 100° C. for 2 hr to give compound 64. The product was purified by chromatography (5-10% Methanol/Dichloromethane).

Mass Spectrum m/e 559.18 (M$^+$+H).

NMR Spectrum (d-6-DMSO, δ values) 2.33 (m, 2H), 3.1 (m, 2H), 3.29 (m, 2H), 3.48 (m, 2H), 3.73 (s, 3H), 3.8 (t, 2H), 3.95 (m, 2H), 3.99 (s, 3H), 4.29 (t, 2H), 6.88 (m, 1H), 7.0 (m, 1H), 7.06 (d, 2H), 7.16 (m, 1H), 7.43 (d, 2H), 7.52 (s, 1H), 8.17 (s, 1H), 8.89 (s, 1H), 11.1 (v.br.s, 2H).

Example 65

Preparation of Compound 65 in Table 9

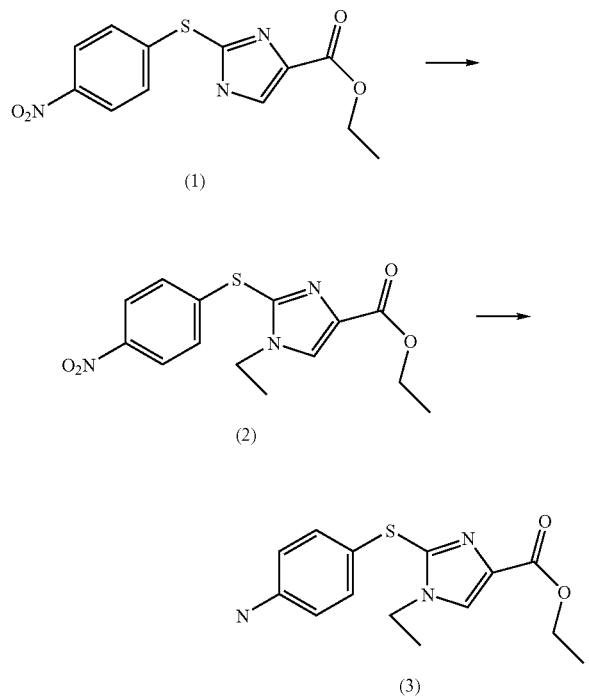

Step 1
4-Fluoro nitrobenzene and 4-ethoxy carbonylimidazole-2-thiol were reacted in the presence of Potassium t-butoxide and DMA to give intermediate (1). The product was purified by chromatography.

Mass Spectrum m/e 294 (M$^+$+H)

Step 2
Intermediate (1) was reacted with methyl cyanide in the presence of NaH and EtI to give intermediate (2). The product was purified by chromatography.

Mass Spectrum m/e 322 (M$^+$+H)

Step 3
Intermediate (2) was reacted with SnCl$_2$ in the presence of HCl and EtOH to give the corresponding aniline derivative.

Mass Spectrum m/e 292 (M$^+$+H)

Step 4
The aniline product of step 3 was reacted with Intermediate D, prepared as described above, in 1-propanol solution at 110° C. for 5 hr to give compound 65.

Mass Spectrum m/e 504 (M$^+$+H)

NMR Spectrum (d-6-DMSO, δ values) 1.25 (m, 6H), 3.95 (s, 6H), 4.05 (q, 2H), 4.2 (q, 2H), 7.2 (d, 2H), 7.4 (d, 2H), 7.5 (s, 1H), 8.15 (s, 1H), 8.25 (s, 1H), 8.9 (s, 1H), 11.25 (br s, 1H)

Example 66

Preparation of Compound No. 66 in Table 9

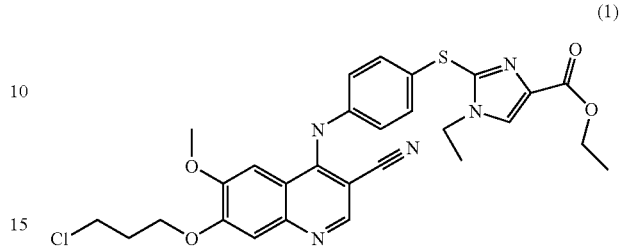

Step 1
The aniline derivative from step 3, example 65 was reacted with Intermediate (A) prepared as described above, in no-propanol solution at 110° C. for 5 hr. to give intermediate (1)

Mass Spectrum m/e 566 (M$^+$+H)

Step 2
Intermediate (1) was reacted with morpholine in the presence of NaI at 50° C. for 18 hr to give compound 66. The product was purified by chromatography.

Mass Spectrum m/e 617 (M$^+$+H)

NMR Spectrum (d-6-DMSO, δ values) 1.25 (t, 3H), 1.3 (t, 3H), 2.3 (m, 2H), 3.1 (m, 2H), 3.25 (m, 2H), 3.45 (m, 2H), 3.8 (t, 2H), 3.95 (m, 2H), 4.0 (s, 3H), 4.05 (m, 2H), 4.2 (q, 2H), 4.3 (q, 2H), 7.2 (d, 2H), 7.4 (d, 2H), 7.5 (s, 1H), 8.2 (s, 1H), 8.9 (s, 1H), 11.3 (br s, 2H)

Example 67

Preparation of Compound No. 67 in Table 9

Step 1
Intermediate (1), example 68 was reacted with oxalyl chloride in the presence of DMF and MeOH to give intermediate (1) above. The product was purified by chromatography.

Mass Spectrum m/e 308 (M$^+$+H)

Step 2
Intermediate (1) was reacted with SnCl$_2$ in the presence of HCl and EtOH to give the corresponding aniline derivative.

Mass Spectrum m/e 278 (M$^+$+H)

Step 3
The product of step 2 was reacted with Intermediate D in 1-propanol at 110° C. for 5 hrs to give compound 69.

Mass Spectrum m/e 490 (M$^+$+H)

NMR Spectrum (d-6-DMSO, δ values) 1.2 (t, 3H), 3.75 (s, 3H), 3.95 (s, 6H), 4.05 (q, 2H), 7.2 (d, 2H), 7.4 (d, 2H), 7.5 (s, 1H), 8.15 (s, 1H), 8.25 (s, 1H), 8.9 (s, 1H), 11.25 (br s, 1H)

Example 68

Preparation of Compound No. 68 in Table 9

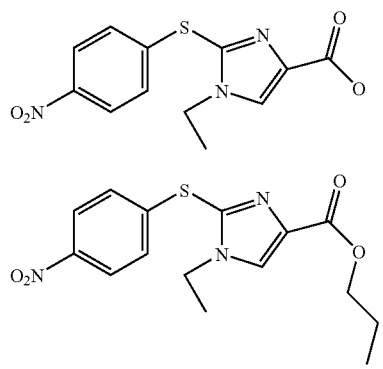

Step 1

Intermediate 2, example 65 was reacted with NaOH in ethanol to give intermediate (1).
Mass Spectrum m/e 294 (M⁺+H)

Step 2

Intermediate (1) was reacted with oxalyl chloride in the DMF and n-propanol to give intermediate (2). The product was purified by chromatography.
Mass Spectrum m/e 336 (M⁺+H)

Step 3

Intermediate (2) was reacted with $SnCl_2$ in the presence of HCl and EtOH to give the corresponding aniline derivative.
Mass Spectrum m/e 306 (M⁺+H)

Step 4

The product of step 3 was reacted with Intermediate D in 1-propanol at 110° C. for 5 hrs to give compound 68. The product was purified by chromatography.
Mass Spectrum m/e 518 (M⁺+H)
NMR Spectrum (d-6-DMSO, δ values) 0.95 (t, 3H), 1.25 (t, 3H), 1.7 (sextet, 2H), 3.95 (s, 6H), 4.05 (q, 2H), 4.1 (t, 2H), 7.2 (d, 2H), 7.4 (d, 2H), 7.5 (s, 1H), 8.2 (s, 1H), 8.25 (s, 1H), 8.95 (s, 1H), 11.35 (br, 1H)

Assay for Inhibitors of the MAP Kinase Pathway

To evaluate inhibitors of the MAPK pathway a coupled assay was carried out which measures phosphorylation of serine/threonine residues present in the substrate in the presence or absence of inhibitor. Recombinant glutathione S-transferase fusion protein containing human p45MEK1 (GST-MEK) was activated by c-raf (Sf9 insect cell lysate from triple baculoviral infection with c-raf/ras/lck) and used for the assay. Active GST-MEK was first used to activate a recombinant glutathione S-transferase fusion protein containing p44MAP kinase (GST-MAPK) in the presence of ATP and $Mg^{2+}$ for 60 min at room temperature in the presence or absence of potential inhibitors. The activated GST-MAPK was then incubated with myelin basic protein (MBP) as substrate for 10 min at room temperature in the presence of ATP, $Mg^{2+}$ and $^{33}P$-ATP. The reaction was stopped by addition of 20% v/v phosphoric acid. Incorporation of $^{33}P$ into the myelin basic protein was determined by capture of the substrate on a filter mat, washing and counting using scintillation methods. The extent of inhibition was determined by comparison with untreated controls.

The final assay solution contained 10 mM Tris, pH 7.5, 0.05 mM EGTA, 8.33 µM [γ₃₃P]ATP, 8.33 mM $Mg(OAc)_2$, 0.5 mM sodium orthovanadate, 0.05% w/v BSA, 6.5 ng GST-MEK, 1 µg GST-MAPK and 16.5 µg MBP in a reaction volume of 60 µl.

Compounds tested of the present invention had $IC_{50}$ results typically less than 0.5 µM. For example, Compound No 3 gave an $IC_{50}$ of 0.0038 µM.

In Vitro MAP Kinase Assay

To determine whether compounds were inhibiting GST-MEK or GST-MAPK, a direct assay of MAPK activity was employed. GST-MAPK was activated by a constitutively active GST-MEK fusion protein containing two point mutations (S217E, S221E) and used for the assay in the presence and absence of potential inhibitors. The activated GST-MAPK was incubated with substrate (MBP) for 60 min at room temperature in the presence of ATP, $Mg^{2+}$ and $^{33}P$-ATP. The reaction was stopped by addition of 20% v/v phosphoric acid. Incorporation of $^{33}P$ into the myelin basic protein was determined by capture of the substrate on a filter mat, washing and counting using scintillation methods.

The final assay solution contained 12 mM Tris, pH 7.5, 0.06 mM EGTA, 30 µM [γ³³P]ATP, 1 mM $Mg(OAc)_2$, 0.6 mM sodium orthovanadate, 0.06% w/v BSA, 28 ng GST-MAPK and 16.5 µg MBP in a reaction volume of 60 µl.

Compounds of the invention showed activity in this screen.

Cell Proliferation Assays

Cells were seeded into multi-well plates at 20 000-40 000 cells/ml in growth medium containing 5% FCS and incubated overnight at 37° C. The compounds were prepared in fresh medium at an appropriate concentration and added to the wells containing the cells. These were then incubated for a further 72 hours. Cells were then either removed from the wells by incubating with trypsin/EDTA and counted using a Coulter counter, or treated with XTT/PMS in PBSA and optical densities read at 450 nm. Compounds tested of the present invention had $IC_{50}$ results typically less than 30 µM. For example, Compound No 3 gave an IC50 of 1.0 µM in HT29 human colon tumour cells.

The invention claimed is:
1. A compound of formula (IE)

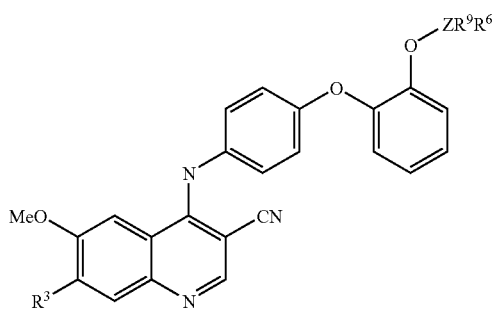

or a pharmaceutically acceptable salt, prodrug or solvate thereof and wherein $R^3$, Z, $R^9$ and $R^6$ are selected from the following groups:

i) $R^3$ is —$OCH_3$, Z is the group —O—$C(CH_3)_2$—CONH—$CH_2$—CONH—, the group $R^9$—$R^6$ is —$C_2H_5$;

ii) $R^3$ is —$OCH_3$, Z is the group —O—$C(CH_3)_2$—CONH—$CH_2$—CONH—, the group $R^9$—$R^6$ is cyclobutyl;

iii) $R^3$ is H, Z is the group —O—$C(CH_3)_2$—CONH, the group $R^9$—$R^6$ is $CH_3$;

iv) $R^3$ is H, Z is the group —O—$C(CH_3)_2$—CONH—$CH_2$—CONH—, the group $R^9$—$R^6$ is $CH_3$;

v) $R^3$ is —$OCH_3$, Z is the group —O—$C(CH_3)_2$—CONH—$CH_2$—CON($CH_3$)—, the group $R^9$—$R^6$ is —$CH_3$;

vi) $R^3$ is —$OCH_3$, Z is the group —O—$C(CH_3)_2$—CONH—$CH_2$—CONH—, the group $R^9$—$R^6$ is cyclopropyl;

vii) $R^3$ is —$OCH_3$, Z is the group —O—$C(CH_3)_2$—CONH—$CH_2$—CONH—$CH_2$, the group $R^9$—$R^6$ is cyclopropyl;

viii) $R^3$ is —$OCH_3$, Z is the group —O—$C(CH_3)_2$—CONH—$CH_2$—CONH—$CH_2$, the group $R^9$—$R^6$ is $CH_3$;

ix) $R^3$ is —$NHCH_3$, Z is the group —O—$C(CH_3)_2$—CONH—; the group $R^9$—$R^6$ is $CH_3$;

x) $R^3$ is —$OCH_3$, Z is the group —O—$C(CH_3)_2$—$(CH_2)_2$—, the group $R^9$—$R^6$ is pyridine;

xi) $R^3$ is —$NHCH_3$, Z is the group —O—$C(CH_3)_2$—CONH—, the group $R^9$—$R^6$ is cyclopropyl;

xii) $R^3$ is —$OCH_3$, Z is the group —O—$C(CH_3)_2$—CONH—$CH_2$—CONH—$(CH_2)_2$—$N(CH_3)$—, the group $R^9$—$R^6$ is —$CH_3$; and xiii) $R^3$ is 3-(1-morpholino)propoxy, Z is the group —O—$C(CH_3)$—CONH—, the group $R^9$—$R^6$ is —$(CH_2)_2OH$.

2. A pharmaceutical composition which comprises a compound of formula (IE) or a pharmaceutically acceptable salt, pro-drug or solvate as defined in claim 1 in association with a pharmaceutically-acceptable diluent or carrier.

* * * * *